US 11,788,056 B2

(12) United States Patent
Curtiss, III et al.

(10) Patent No.: US 11,788,056 B2
(45) Date of Patent: *Oct. 17, 2023

(54) INDUCTION OF PROTECTIVE IMMUNITY AGAINST ANTIGENS

(71) Applicant: University of Florida Research Foundation, Incorporated, Gainesville, FL (US)

(72) Inventors: Roy Curtiss, III, Gainesville, FL (US); Shifeng Wang, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 224 days.

This patent is subject to a terminal disclaimer.

(21) Appl. No.: 17/213,619

(22) Filed: Mar. 26, 2021

(65) Prior Publication Data

US 2021/0284955 A1    Sep. 16, 2021

Related U.S. Application Data

(63) Continuation of application No. 16/480,253, filed as application No. PCT/US2018/014860 on Jan. 23, 2018, now Pat. No. 10,988,729.

(60) Provisional application No. 62/541,293, filed on Aug. 4, 2017, provisional application No. 62/449,228, filed on Jan. 23, 2017.

(51) Int. Cl.
| | |
|---|---|
| *C12N 1/36* | (2006.01) |
| *A61P 31/04* | (2006.01) |
| *A61K 39/112* | (2006.01) |
| *A61K 39/08* | (2006.01) |
| *C12N 15/74* | (2006.01) |
| *A61K 39/00* | (2006.01) |

(52) U.S. Cl.
CPC ............ *C12N 1/36* (2013.01); *A61K 39/0275* (2013.01); *A61K 39/08* (2013.01); *A61P 31/04* (2018.01); *C12N 15/74* (2013.01); *A61K 2039/522* (2013.01); *A61K 2039/523* (2013.01); *A61K 2039/542* (2013.01)

(58) Field of Classification Search
CPC .......... C12N 1/36; C12N 15/74; A61P 31/04; A61K 39/0275; A61K 2039/522; A61K 2039/523
See application file for complete search history.

(56) References Cited

U.S. PATENT DOCUMENTS

| 8,465,755 B2 | 6/2013 | Curtiss, III et al. | |
| 9,040,059 B2 | 5/2015 | Curtiss, III et al. | |
| 9,050,285 B2 | 6/2015 | Curtiss, III et al. | |
| 10,988,729 B2 * | 4/2021 | Curtiss, III | A61P 37/04 |
| 2011/0256181 A1 | 10/2011 | Curtiss, III et al. | |
| 2011/0287052 A1 | 11/2011 | Curtiss, III et al. | |
| 2013/0337013 A1 | 12/2013 | Mellata | |
| 2016/0074440 A1 | 3/2016 | Brugere et al. | |
| 2019/0185520 A1 | 6/2019 | Curtiss, III | |
| 2020/0368339 A1 | 11/2020 | Curtiss, III et al. | |

FOREIGN PATENT DOCUMENTS

| EP | 1874344 A1 | 1/2008 |
| WO | 2006/113772 A1 | 10/2006 |
| WO | 2009/046449 A1 | 4/2009 |
| WO | 2009/046451 A1 | 4/2009 |
| WO | 2010/045620 A1 | 4/2010 |
| WO | 2011/150421 A2 | 12/2011 |
| WO | 2015/118541 A1 | 8/2015 |

OTHER PUBLICATIONS

Czeczulin et al., Cloning, nucleotide sequencing, and expression of the Clostridium perfringens enterotoxin gene in *Escherichia coli*. Infect Immun. Aug. 1993;61(8):3429-39.

Dwivedi et al., Comparative analysis of extractable proteins from Clostridium perfringens type A and type C strains showing varying degree of virulence. Anaerobe. Oct. 2015;35(Pt B):77-91.

Kulkarni et al., Oral immunization of broiler chickens against necrotic enteritis with an attenuated *Salmonella* vaccine vector expressing Clostridium perfringens antigens. Vaccine. Aug. 5, 2008;26(33):4194-203.

Zekarias et al., Recombinant attenuated *Salmonella enterica* serovar typhimurium expressing the carboxy-terminal domain of alpha toxin from Clostridium perfringens induces protective responses against necrotic enteritis in chickens. Clin Vaccine Immunol. May 2008;15(5):805-16.

Extended European Search Report for Application No. EP18841409. 8, dated May 10, 2021, 11 pages.

U.S. Appl. No. 16/480,253, filed Jul. 23, 2019, U.S. Pat. No. 10,988,729, Issued.

U.S. Appl. No. 17/213,619, filed Feb. 3, 2020, 2020-0368339, Published.

Coleman et al., Cloning and characterization of a conjugated bile acid hydrolase gene from Clostridium perfringens. Appl Environ Microbiol. Jul. 1995;61(7):2514-20.

Curtiss et al., New technologies in using recombinant attenuated *Salmonella* vaccine vectors. Crit Rev Immunol. 2010;30(3):255-270.

Jiang et al., Protection Against Necrotic Enteritis in Broiler Chickens by Regulated Delayed Lysis *Salmonella* Vaccines. Avian Dis. 2015;59(4):475-485.

Kong et al., Effect of deletion of genes involved in lipopolysaccharide core and O-antigen synthesis on virulence and immunogenicity of *Salmonella enterica* serovar typhimurium. Infect Immun. Oct. 2011;79(10):4227-39.

(Continued)

*Primary Examiner* — Mary Maille Lyons
(74) *Attorney, Agent, or Firm* — McCarter & English, LLP; Marcie B. Clarke

(57) ABSTRACT

Described herein are compositions and methods for making and using recombinant bacteria that are capable of regulated attenuation and/or regulated expression of one or more antigens of interest.

16 Claims, 16 Drawing Sheets

Specification includes a Sequence Listing.

(56) References Cited

OTHER PUBLICATIONS

Kong et al., Turning self-destructing *Salmonella* into a universal DNA vaccine delivery platform. Proc Natl Acad Sci U S A. Nov. 20, 2012;109(47):19414-9. Including supplementary information.
International Preliminary Report on Patentability for Application No. PCT/US2018/014860, dated Aug. 1, 2019, 7 pages.
International Preliminary Report on Patentability for Application No. PCT/US2018/045231, dated Feb. 13, 2020, 6 pages.
International Search Report and Written Opinion for Application No. PCT/US2018/014860, dated Apr. 17, 2018, 9 pages.
International Search Report and Written Opinion for Application No. PCT/US2018/045231, dated Nov. 5, 2018, 8 pages.

* cited by examiner

Fig. 3C

| Galactose Concentration (%) | χ4094 galE496 | | χ4700 Δ(galE-uvrB)-1005 | | χ9792 Δ(galE-ybhC)-851 | |
|---|---|---|---|---|---|---|
| | LB | NB | LB | NB | LB | NB |
| 0 | 1.069 | 1.452 | 1.070 | 1.506 | 1.538 | 1.141 |
| 0.0001 | 1.049 | 1.447 | 1.068 | 1.509 | 1.518 | 1.165 |
| 0.001 | 1.088 | 1.469 | 1.078 | 1.551 | 1.561 | 1.177 |
| 0.01 | 0.153 | 0.330 | 0.959 | 1.391 | 1.396 | 1.074 |
| 0.1 | 0.152 | 0.295 | 0.874 | 1.340 | 1.393 | 1.029 |
| 0.2 | 0.142 | 0.241 | 0.847 | 1.308 | 1.330 | 0.999 |

- Values shown are $OD_{600}$.   LB: LB broth   NB: Nutrient Broth
- Cultures were grown in medias with different galactose concentrations overnight

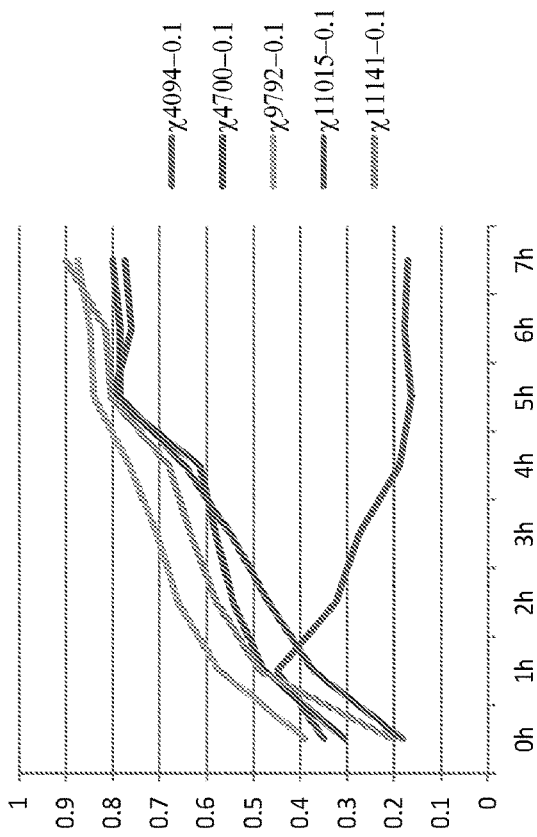
Fig. 4F
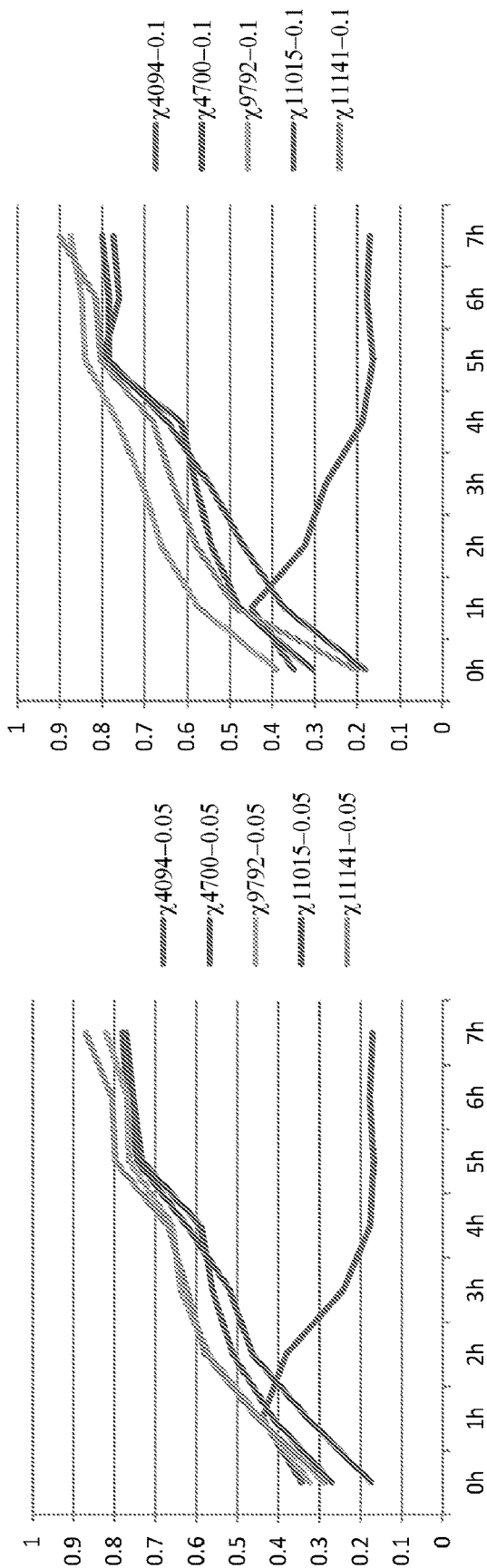
Fig. 4E
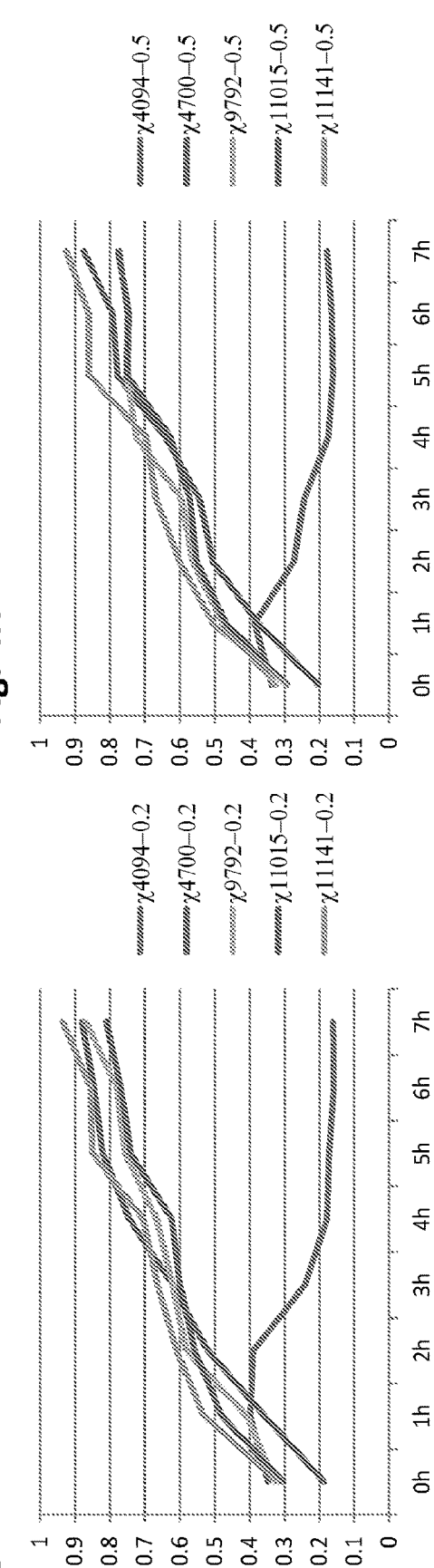
Fig. 4H
Fig. 4G

χ4094: *galE496*
χ4700: Δ*(galE-uvrB)-1005*
χ9792: Δ*(galE-ybhC)-851*
* The colonization of Δ*(galE-ybhC)-851* is between *galE496* and Δ*(galE-uvrB)-1005*

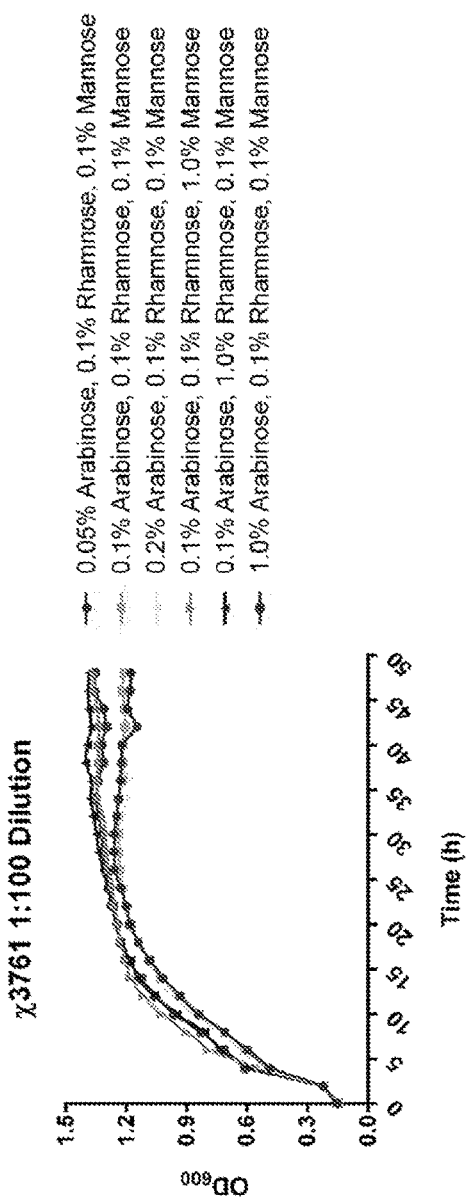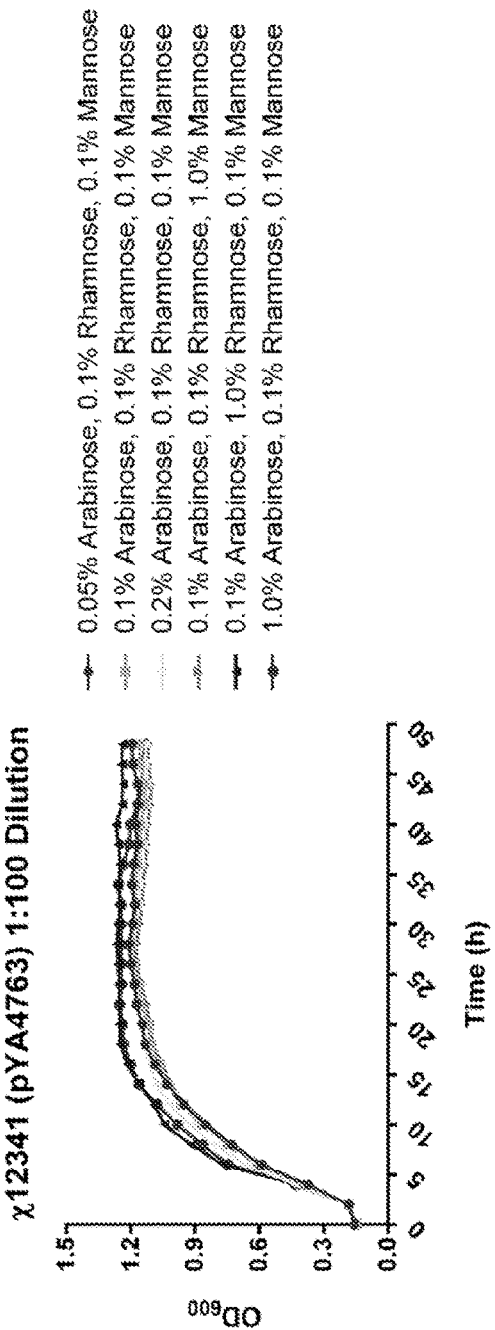
Fig. 6A
Fig. 6B

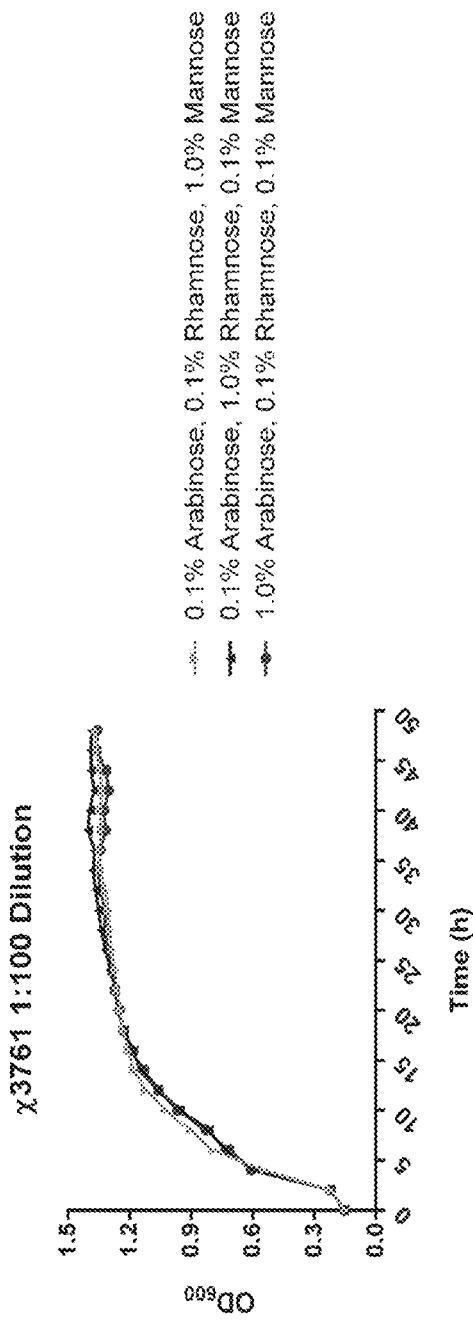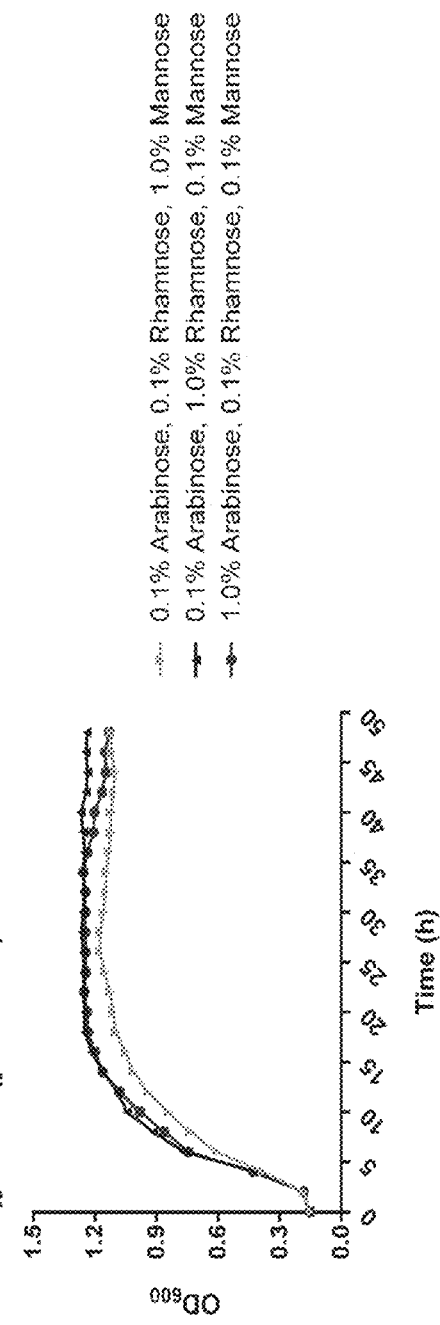
Fig. 6G
Fig. 6H

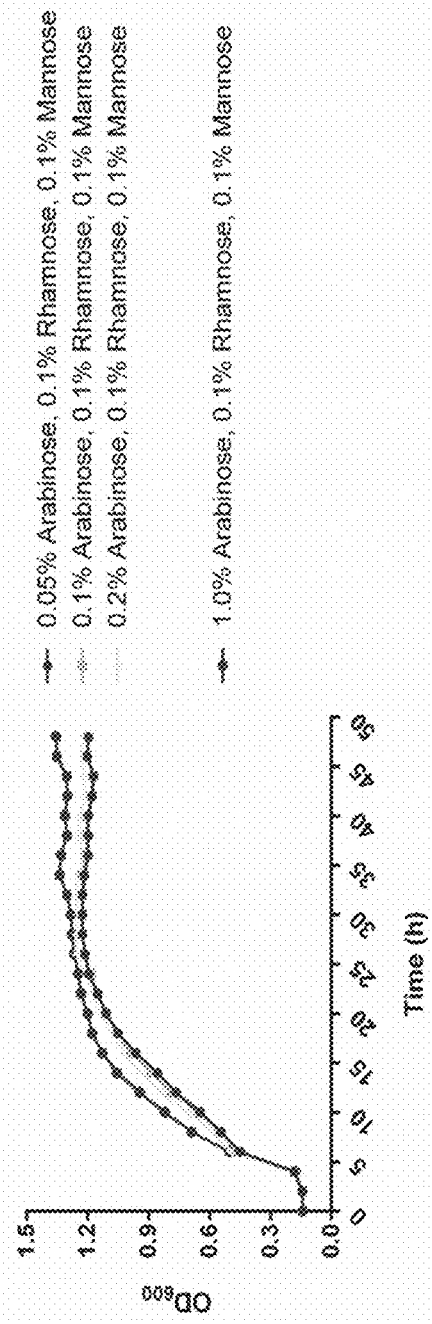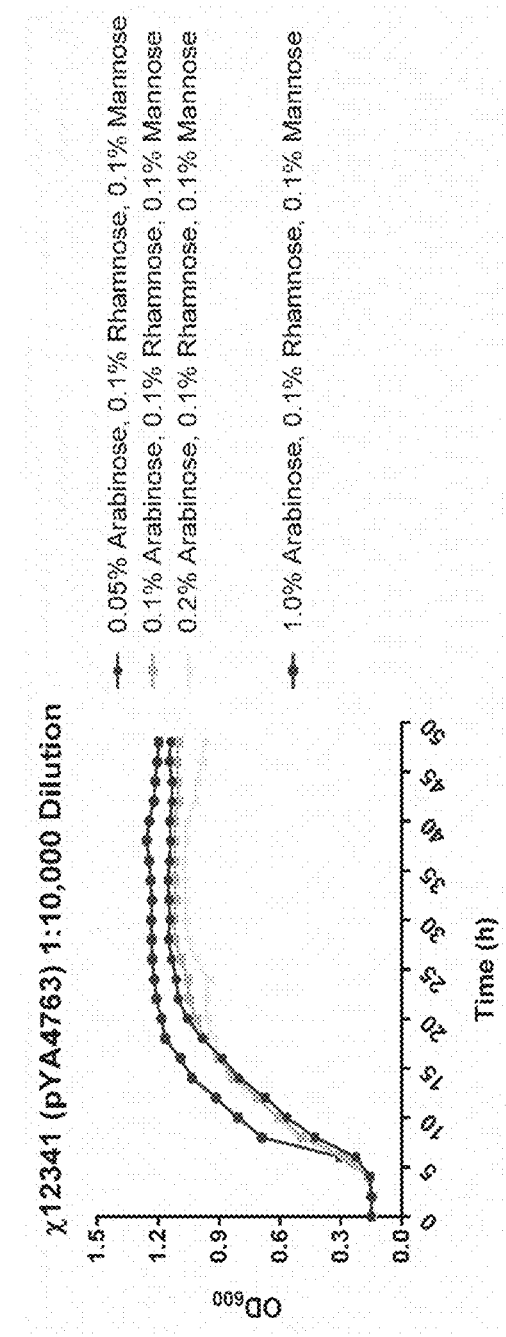
Fig. 6Q
Fig. 6R

SEQUENCE LISTING

```
<160> NUMBER OF SEQ ID NOS: 12

<210> SEQ ID NO 1
<211> LENGTH: 1215
<212> TYPE: DNA
<213> ORGANISM: Artificial Sequence
<220> FEATURE:
<223> OTHER INFORMATION: Synthetic polynucleotide

<400> SEQUENCE: 1
atgctaacca catcattaac gttaaataaa gagaaatgga agccgatctg gaataaagcg      60 ctggttttc tttttgttgc cacgtatttt ctggatggta ttacgcgtta taaacatttg     120
ataatcatac ttatggttat caccgcgatt tatcaggtct cacgctcacc gaaaagtttc     180
ccccctcttt tcaaaaatag cgtattttat agcgtagcag tattatcatt aatccttgtt     240
tattccatac tcatatcgcc agatatgaaa gaaagtttca aggaatttga aaatacggta     300
ctggagggct tcttattata tactttatta attcccgtac tattaaaaga tgaaacaaaa     360
gaaacggttg cgaaaatagt acttttctcc tttttaacaa gtttaggact tcgctgcctt     420
gcagagagta ttctgtatat cgaggactat aataaaggga ttatgccatt cataagctat     480
gcgcatcgac atatgtccga ttccatggtt ttcttatttc cagcattatt gaatatttgg     540
ctgtttagaa aaaatgcaat taagttggtt tttttggtgc ttagcgccat ctacctttttc     600 tttatcctgg gaaccctatc gcgaggggca tggttggcgg tgcttatagt aggtgttctg     660
tgggcaatac tgaaccgcca atggaagtta ataggagttg gtgccatttt attagccatt     720
atcggcgctt tggttatcac tcaacataat aacaaaccag acccagaaca tttactgtat     780
aaattacagc agacagatag ctcatatcgt tatactaacg gaacccaggg caccgcgtgg     840
atactgattc aggaaaaccc gatcaagggc tacggctatg gtaatgatgt gtatgatggt     900
gtttataata aacgcgttgt cgattatcca acgtggacct taaagaatc tatcggtccg     960 cataatacca ttctgtacat ctggtttagt gcaggcatat gggtctggc gagcctggtc    1020
```

```
tatttatatg gcgctatcat cagggaaaca gccagctcta ccctcaggaa agtagagata   1080
agcccctaca atgctcatct cttgctattt ttatctttcg tcggtttttta tatcgttcgt   1140 ggcaattttg aacaggtcga tattgctcaa attggtatca ttaccggttt tctgctggcg   1200
ctaagaaata gataa                                                    1215
```

```
<210> SEQ ID NO 2
<211> LENGTH: 404
<212> TYPE: PRT
<213> ORGANISM: Artificial Sequence
<220> FEATURE:
<223> OTHER INFORMATION: Synthetic polypeptide

<400> SEQUENCE: 2

Met Leu Thr Thr Ser Leu Thr Leu Asn Lys Glu Lys Trp Lys Pro Ile
1               5                   10                  15

Trp Asn Lys Ala Leu Val Phe Leu Phe Val Ala Thr Tyr Phe Leu Asp
                20                  25                  30

Gly Ile Thr Arg Tyr Lys His Leu Ile Ile Ile Leu Met Val Ile Thr
            35                  40                  45

Ala Ile Tyr Gln Val Ser Arg Ser Pro Lys Ser Phe Pro Pro Leu Phe
        50                  55                  60

Lys Asn Ser Val Phe Tyr Ser Val Ala Val Leu Ser Leu Ile Leu Val
65                  70                  75                  80

Tyr Ser Ile Leu Ile Ser Pro Asp Met Lys Glu Ser Phe Lys Glu Phe
                85                  90                  95

Glu Asn Thr Val Leu Glu Gly Phe Leu Leu Tyr Thr Leu Leu Ile Pro
            100                 105                 110

Val Leu Leu Lys Asp Glu Thr Lys Glu Thr Val Ala Lys Ile Val Leu
        115                 120                 125

Phe Ser Phe Leu Thr Ser Leu Gly Leu Arg Cys Leu Ala Glu Ser Ile
130                 135                 140

Leu Tyr Ile Glu Asp Tyr Asn Lys Gly Ile Met Pro Phe Ile Ser Tyr
145                 150                 155                 160

Ala His Arg His Met Ser Asp Ser Met Val Phe Leu Phe Pro Ala Leu
                165                 170                 175

Leu Asn Ile Trp Leu Phe Arg Lys Asn Ala Ile Lys Leu Val Phe Leu
            180                 185                 190

Val Leu Ser Ala Ile Tyr Leu Phe Phe Ile Leu Gly Thr Leu Ser Arg
        195                 200                 205

Gly Ala Trp Leu Ala Val Leu Ile Val Gly Val Leu Trp Ala Ile Leu
210                 215                 220

Asn Arg Gln Trp Lys Leu Ile Gly Val Gly Ala Ile Leu Leu Ala Ile
225                 230                 235                 240

Ile Gly Ala Leu Val Ile Thr Gln His Asn Asn Lys Pro Asp Pro Glu
                245                 250                 255

His Leu Leu Tyr Lys Leu Gln Gln Thr Asp Ser Ser Tyr Arg Tyr Thr
            260                 265                 270

Asn Gly Thr Gln Gly Thr Ala Trp Ile Leu Ile Gln Glu Asn Pro Ile
        275                 280                 285

Lys Gly Tyr Gly Tyr Gly Asn Asp Val Tyr Asp Gly Val Tyr Asn Lys
290                 295                 300

Arg Val Val Asp Tyr Pro Thr Trp Thr Phe Lys Glu Ser Ile Gly Pro
305                 310                 315                 320

His Asn Thr Ile Leu Tyr Ile Trp Phe Ser Ala Gly Ile Leu Gly Leu
```

```
              325                 330                 335
Ala Ser Leu Val Tyr Leu Tyr Gly Ala Ile Ile Arg Glu Thr Ala Ser
            340                 345                 350

Ser Thr Leu Arg Lys Val Glu Ile Ser Pro Tyr Asn Ala His Leu Leu
        355                 360                 365

Leu Phe Leu Ser Phe Val Gly Phe Tyr Ile Val Arg Gly Asn Phe Glu
    370                 375                 380

Gln Val Asp Ile Ala Gln Ile Gly Ile Ile Thr Gly Phe Leu Leu Ala
385                 390                 395                 400

Leu Arg Asn Arg

<210> SEQ ID NO 3
<211> LENGTH: 453
<212> TYPE: DNA
<213> ORGANISM: Artificial Sequence
<220> FEATURE:
<223> OTHER INFORMATION: Synthetic polynucleotide

<400> SEQUENCE: 3
atgactgaca acaataccgc attaaagaag gctggcctga agtaacgct tcctcgttta      60 aaaattctgg aagttcttca ggaaccagat aaccatcacg tcagtgcgga agatttatac   120
aaacgcctga tcgacatggg tgaagaaatc ggtctggcaa ccgtataccg tgtgctgaac   180
cagtttgacg atgccggtat cgtgacccgc cataattttg aaggcggtaa atccgttttt   240
gaactgacgc aacagcatca tcacgaccat cttatctgcc ttgattgcgg aaaagtgatt   300
gaatttagtg atgactctat tgaagcgcgc cagcgtgaaa ttgcggcgaa acacggtatt   360
cgtttaacta atcacagcct ctatctttac ggccactgcg ctgaaggcga ctgccgcgaa   420
gacgagcacg cgcacgatga cgcgactaaa taa                                 453

<210> SEQ ID NO 4
<211> LENGTH: 150
<212> TYPE: PRT
<213> ORGANISM: Artificial Sequence
<220> FEATURE:
<223> OTHER INFORMATION: Synthetic polypeptide

<400> SEQUENCE: 4

Met Thr Asp Asn Asn Thr Ala Leu Lys Lys Ala Gly Leu Lys Val Thr
1               5                  10                  15

Leu Pro Arg Leu Lys Ile Leu Glu Val Leu Gln Glu Pro Asp Asn His
            20                  25                  30

His Val Ser Ala Glu Asp Leu Tyr Lys Arg Leu Ile Asp Met Gly Glu
        35                  40                  45

Glu Ile Gly Leu Ala Thr Val Tyr Arg Val Leu Asn Gln Phe Asp Asp
    50                  55                  60

Ala Gly Ile Val Thr Arg His Asn Phe Glu Gly Gly Lys Ser Val Phe
65                  70                  75                  80

Glu Leu Thr Gln Gln His His His Asp His Leu Ile Cys Leu Asp Cys
                85                  90                  95

Gly Lys Val Ile Glu Phe Ser Asp Asp Ser Ile Glu Ala Arg Gln Arg
            100                 105                 110

Glu Ile Ala Ala Lys His Gly Ile Arg Leu Thr Asn His Ser Leu Tyr
        115                 120                 125

Leu Tyr Gly His Cys Ala Glu Gly Asp Cys Arg Glu Asp Glu His Ala
    130                 135                 140
```

His Asp Asp Ala Thr Lys
145                 150

<210> SEQ ID NO 5
<211> LENGTH: 453
<212> TYPE: DNA
<213> ORGANISM: Artificial Sequence
<220> FEATURE:
<223> OTHER INFORMATION: Synthetic polynucleotide

<400> SEQUENCE: 5

```
atgactgaca acaataccgc attaaagaag gctggcctga agtaacgct tcctcgttta      60
aaaattctgg aagttcttca ggaaccagat aaccatcacg tcagtgcgga agatttatac   120
aaacgcctga tcgacatggg tgaagaaatc ggtctggcaa ccgtataccg tgtgctgaac   180
cagtttgacg atgccggtat cgtgacccgc cataattttg aaggcggtaa atccgttttt   240
gaactgacgc aacagcatca tcacgaccat cttatctgcc ttgattgcgg aaaagtgatt   300
gaatttagtg atgactctat tgaagcgcgc cagcgtgaaa ttgcggcgaa acacggtatt   360
cgtttaacta atcacagcct ctatctttac ggccactgcg ctgaaggcga ctgccgcgaa   420
gacgagcacg cgcacgatga cgcgactaaa taa                                 453
```

<210> SEQ ID NO 6
<211> LENGTH: 150
<212> TYPE: PRT
<213> ORGANISM: Artificial Sequence
<220> FEATURE:
<223> OTHER INFORMATION: Synthetic polypeptide

<400> SEQUENCE: 6

Met Thr Asp Asn Asn Thr Ala Leu Lys Lys Ala Gly Leu Lys Val Thr
1               5                   10                  15

Leu Pro Arg Leu Lys Ile Leu Glu Val Leu Gln Glu Pro Asp Asn His
            20                  25                  30

His Val Ser Ala Glu Asp Leu Tyr Lys Arg Leu Ile Asp Met Gly Glu
        35                  40                  45

Glu Ile Gly Leu Ala Thr Val Tyr Arg Val Leu Asn Gln Phe Asp Asp
    50                  55                  60

Ala Gly Ile Val Thr Arg His Asn Phe Glu Gly Gly Lys Ser Val Phe
65                  70                  75                  80

Glu Leu Thr Gln Gln His His His Asp His Leu Ile Cys Leu Asp Cys
                85                  90                  95

Gly Lys Val Ile Glu Phe Ser Asp Asp Ser Ile Glu Ala Arg Gln Arg
            100                 105                 110

Glu Ile Ala Ala Lys His Gly Ile Arg Leu Thr Asn His Ser Leu Tyr
        115                 120                 125

Leu Tyr Gly His Cys Ala Glu Gly Asp Cys Arg Glu Asp Glu His Ala
    130                 135                 140

His Asp Asp Ala Thr Lys
145                 150

<210> SEQ ID NO 7
<211> LENGTH: 1011
<212> TYPE: DNA
<213> ORGANISM: Artificial Sequence
<220> FEATURE:
<223> OTHER INFORMATION: Synthetic polynucleotide

<400> SEQUENCE: 7

```
atgccgatta ctataggga atggttttta aaaagtgaaa tccttaccaa ctccccaagg      60
aatacgaaag aagcatggtg gaaagttta tgggaaaaaa ttaaagactt ctttttttct     120
actggcaaag caaaagcgga ccgttgtcta catgagatgt tgtttgccga acgcgccccc    180
acacgagagc ggcttacaga gattttttt gagttgaaag agttagcctg cgcatcgcaa    240
agagatagat ttcaggttca taatcctcat gaaaatgatg ccaccattat tcttcgcatc    300
atggatcaaa acgaagagaa cgaattgtta cgtatcactc aaaataccga tacctttagc    360
tgtgaagtca tggggaatct ttatttttta atgaaagatc gcccggatat tttaaaatcg    420
catccacaaa tgacggccat gattaagaga agatatagcg aaatcgtaga ctaccccctc    480
ccttcgacat tatgtctcaa tcctgctggc gcgccgatat tatcggttcc attagacaac    540
atagaggggt attttatatac tgaattgaga aaggacatt tagatgggtg aaagcgcaa    600 gaaaaggcaa cctacctggc agcgaaaatt cagtctggga ttgaaaagac aacgcgcatt    660
ttacaccatg cgaatatatc cgaaagtact cagcaaaacg cattttttaga aacaatggcg    720 atgtgtggat taaaacagct tgaaatacca ccaccgcata cccacatacc tattgaaaaa    780
atggtaaaag aggttttact agcggataag acgtttcagg cgttcctcgt aacggatccc    840
agcaccagcc aaagtatgtt agctgagata gtcgaagcca tctctgatca ggttttcac    900 gccattttta aatagacccc ccaggctata caaaaaatgg cggaagaaca gttaaccacg    960
ctacacgttc gctcagaaca acaaagcggc tgtttatgtt gttttttata a            1011
```

<210> SEQ ID NO 8
<211> LENGTH: 336
<212> TYPE: PRT
<213> ORGANISM: Artificial Sequence
<220> FEATURE:
<223> OTHER INFORMATION: Synthetic polypeptide

<400> SEQUENCE: 8

```
Met Pro Ile Thr Ile Gly Asn Gly Phe Leu Lys Ser Glu Ile Leu Thr
1               5                   10                  15

Asn Ser Pro Arg Asn Thr Lys Glu Ala Trp Trp Lys Val Leu Trp Glu
            20                  25                  30

Lys Ile Lys Asp Phe Phe Ser Thr Gly Lys Ala Lys Ala Asp Arg
        35                  40                  45

Cys Leu His Glu Met Leu Phe Ala Glu Arg Ala Pro Thr Arg Glu Arg
    50                  55                  60

Leu Thr Glu Ile Phe Phe Glu Leu Lys Glu Leu Ala Cys Ala Ser Gln
65                  70                  75                  80

Arg Asp Arg Phe Gln Val His Asn Pro His Glu Asn Asp Ala Thr Ile
                85                  90                  95

Ile Leu Arg Ile Met Asp Gln Asn Glu Glu Asn Glu Leu Leu Arg Ile
            100                 105                 110

Thr Gln Asn Thr Asp Thr Phe Ser Cys Glu Val Met Gly Asn Leu Tyr
        115                 120                 125

Phe Leu Met Lys Asp Arg Pro Asp Ile Leu Lys Ser His Pro Gln Met
    130                 135                 140

Thr Ala Met Ile Lys Arg Arg Tyr Ser Glu Ile Val Asp Tyr Pro Leu
145                 150                 155                 160

Pro Ser Thr Leu Cys Leu Asn Pro Ala Gly Ala Pro Ile Leu Ser Val
                165                 170                 175

Pro Leu Asp Asn Ile Glu Gly Tyr Leu Tyr Thr Glu Leu Arg Lys Gly
            180                 185                 190
```

His Leu Asp Gly Trp Lys Ala Gln Glu Lys Ala Thr Tyr Leu Ala Ala
    195                 200                 205

Lys Ile Gln Ser Gly Ile Glu Lys Thr Thr Arg Ile Leu His His Ala
210                 215                 220

Asn Ile Ser Glu Ser Thr Gln Gln Asn Ala Phe Leu Glu Thr Met Ala
225                 230                 235                 240

Met Cys Gly Leu Lys Gln Leu Glu Ile Pro Pro His Thr His Ile
                245                 250                 255

Pro Ile Glu Lys Met Val Lys Glu Val Leu Leu Ala Asp Lys Thr Phe
            260                 265                 270

Gln Ala Phe Leu Val Thr Asp Pro Ser Thr Ser Gln Ser Met Leu Ala
                275                 280                 285

Glu Ile Val Glu Ala Ile Ser Asp Gln Val Phe His Ala Ile Phe Arg
    290                 295                 300

Ile Asp Pro Gln Ala Ile Gln Lys Met Ala Glu Gln Leu Thr Thr
305                 310                 315                 320

Leu His Val Arg Ser Glu Gln Gln Ser Gly Cys Leu Cys Cys Phe Leu
                325                 330                 335

<210> SEQ ID NO 9
<211> LENGTH: 1083
<212> TYPE: DNA
<213> ORGANISM: Artificial Sequence
<220> FEATURE:
<223> OTHER INFORMATION: Synthetic polynucleotide

<400> SEQUENCE: 9

```
gtgaaaccag taacgttata cgatgtcgca gagtatgccg gtgtctctta tcagaccgtt        60
tcccgcgtgg tgaaccaggc cagccacgtt tctgcgaaaa cgcgggaaaa agtggaagcg       120
gcgatggcgg agctgaatta cattcccaac cgcgtggcac aacaactggc gggcaaacag       180
tcgttgctga ttggcgttgc cacctccagt ctggccctgc acgcgccgtc gcaaattgtc       240
gcggcgatta atctcgcgc cgatcaactg ggtgccagcg tggtggtgtc gatggtagaa       300
cgaagcggcg tcgaagcctg taaagcggcg gtgcacaatc ttctcgcgca acgcgtcagt       360
gggctgatca ttaactatcc gctggatgac caggatgcca ttgctgtgga agctgcctgc       420
actaatgttc cggcgttatt tcttgatgtc tctgaccaga cacccatcaa cagtattatt       480
ttctcccatg aagacggtac gcgactgggc gtggagcatc tggtcgcatt gggtcaccag       540
caaatcgcgc tgttagcggg cccattaagt tctgtctcgg cgcgtctgcg tctggctggc       600
tggcataaat atctcactcg caatcaaatt cagccgatag cggaacggga aggcgactgg       660
agtgccatgt ccggttttca acaaaccatg caaatgctga atgagggcat cgttcccact       720
gcgatgctgg ttgccaacga tcagatggcg ctgggcgcaa tgcgcgccat taccgagtcc       780
gggctgcgcg ttggtgcgga tatctcggta gtgggatacg acgataccga agacagctca       840
tgttatatcc cgccgttaac caccatcaaa caggattttc gcctgctggg gcaaaccagc       900
gtggaccgct gctgcaact ctctcagggc caggcggtga agggcaatca gctgttgccc       960
gtctcactgg tgaaaagaaa aaccaccctg gcgcccaata cgcaaaccgc ctctccccgc      1020
gcgttggccg attcattaat gcagctggca cgacaggttt cccgactgga aagcgggcag      1080
tga                                                                    1083
```

<210> SEQ ID NO 10
<211> LENGTH: 360

<212> TYPE: PRT
<213> ORGANISM: Artificial Sequence
<220> FEATURE:
<223> OTHER INFORMATION: Synthetic polypeptide

<400> SEQUENCE: 10

```
Met Lys Pro Val Thr Leu Tyr Asp Val Ala Glu Tyr Ala Gly Val Ser
1               5                   10                  15

Tyr Gln Thr Val Ser Arg Val Val Asn Gln Ala Ser His Val Ser Ala
            20                  25                  30

Lys Thr Arg Glu Lys Val Glu Ala Ala Met Ala Glu Leu Asn Tyr Ile
        35                  40                  45

Pro Asn Arg Val Ala Gln Gln Leu Ala Gly Lys Gln Ser Leu Leu Ile
50                  55                  60

Gly Val Ala Thr Ser Ser Leu Ala Leu His Ala Pro Ser Gln Ile Val
65                  70                  75                  80

Ala Ala Ile Lys Ser Arg Ala Asp Gln Leu Gly Ala Ser Val Val Val
                85                  90                  95

Ser Met Val Glu Arg Ser Gly Val Glu Ala Cys Lys Ala Ala Val His
            100                 105                 110

Asn Leu Leu Ala Gln Arg Val Ser Gly Leu Ile Ile Asn Tyr Pro Leu
        115                 120                 125

Asp Asp Gln Asp Ala Ile Ala Val Glu Ala Ala Cys Thr Asn Val Pro
130                 135                 140

Ala Leu Phe Leu Asp Val Ser Asp Gln Thr Pro Ile Asn Ser Ile Ile
145                 150                 155                 160

Phe Ser His Glu Asp Gly Thr Arg Leu Gly Val Glu His Leu Val Ala
                165                 170                 175

Leu Gly His Gln Gln Ile Ala Leu Leu Ala Gly Pro Leu Ser Ser Val
            180                 185                 190

Ser Ala Arg Leu Arg Leu Ala Gly Trp His Lys Tyr Leu Thr Arg Asn
        195                 200                 205

Gln Ile Gln Pro Ile Ala Glu Arg Glu Gly Asp Trp Ser Ala Met Ser
210                 215                 220

Gly Phe Gln Gln Thr Met Gln Met Leu Asn Glu Gly Ile Val Pro Thr
225                 230                 235                 240

Ala Met Leu Val Ala Asn Asp Gln Met Ala Leu Gly Ala Met Arg Ala
                245                 250                 255

Ile Thr Glu Ser Gly Leu Arg Val Gly Ala Asp Ile Ser Val Val Gly
            260                 265                 270

Tyr Asp Asp Thr Glu Asp Ser Ser Cys Tyr Ile Pro Pro Leu Thr Thr
        275                 280                 285

Ile Lys Gln Asp Phe Arg Leu Leu Gly Gln Thr Ser Val Asp Arg Leu
290                 295                 300

Leu Gln Leu Ser Gln Gly Gln Ala Val Lys Gly Asn Gln Leu Leu Pro
305                 310                 315                 320

Val Ser Leu Val Lys Arg Lys Thr Thr Leu Ala Pro Asn Thr Gln Thr
                325                 330                 335

Ala Ser Pro Arg Ala Leu Ala Asp Ser Leu Met Gln Leu Ala Arg Gln
            340                 345                 350

Val Ser Arg Leu Glu Ser Gly Gln
        355                 360
```

<210> SEQ ID NO 11
<211> LENGTH: 4844

```
<212> TYPE: DNA
<213> ORGANISM: Artificial Sequence
<220> FEATURE:
<223> OTHER INFORMATION: Synthetic polynucleotide

<400> SEQUENCE: 11
gggcgaattc gagctcggta ccctcgaggc tgaatttcat tacgaccagt ctaaaaagcg      60
cctgaattcg cgaccttctc gttactgaca ggaaaatggg ccattggcaa ccagggaaag     120
atgaacgtga tgatgttcac aatttgctga attgtggtga tgtgatgctc accgcatttc     180
ctgaaaattc acgctgtatc ttgaaaaatc gacgtttttt acgtggtttt ccgtcgaaaa     240
tttaaggtaa gaacctgacc tcgtgattac tatttcgccg tgttgacgac atcaggaggc     300
cagtatgacc gtattacata gtgtggattt ttttccgtct ggtaacgcgt ccgtggcgat     360
agaaccccgg ctcccgcagg cggatttttcc tgaacatcat catgattttc atgaaattgt     420
gattgtcgaa catggcacgg gtattcatgt gtttaatggg cagccctata ccatcaccgg     480
tggcacggtc tgtttcgtac gcgatcatga tcggcatctg tatgaacata ccgataatct     540
gtgtctgacc aatgtgctgt atcgctcgcc ggatcgattt cagtttctcg ccgggctgaa     600
tcagttgctg ccacaagagc tggatgggca gtatccgtct cactggcgcg ttaaccacag     660
cgtattgcag caggtgcgac agctggttgc acagatggaa cagcaggaag gggaaaatga     720
tttaccctcg accgccagtc gcgagatctt gtttatgcaa ttactgctct tgctgcgtaa     780
aagcagtttg caggagaacc tggaaaacag cgcatcacgt ctcaacttgc ttctggcctg     840
gctggaggac cattttgccg atgaggtgaa ttgggatgcc gtggcggatc aattttctct     900
ttcactgcgt acgctacatc ggcagcttaa gcagcaaacg ggactgacgc ctcagcgata     960
cctgaaccgc ctgcgactga tgaaagcccg acatctgcta cgccacagcg aggccagcgt    1020
tactgacatc gcctatcgct gtggattcag cgacagtaac cacttttcga cgcttttttcg    1080 ccgagagttt aactggtcac cgcgtgatat tcgccaggga cgggatggct ttctgcaata    1140
acgcgaatct tctcaacgta tttgtacgcc atattgcgaa taatcaactt cgttctctgg    1200
ccgaggtagc cacggtggcg catcagttaa aacttctcaa agatgatttt tttgccagcg    1260
accagcaggc agtcgctgtg gctgaccgtt atccgcaaga tgtctttgct gaacatacac    1320 atgattttg tgagctggtg attgtctggc gcggtaatgg cctgcatgta ctcaacgatc    1380
gcccttatcg cattacccgt ggcgatctct tttacattca tgctgacgat aaacactcct    1440
acgcttccgt taacgatctg gttttgcaga atattattta ttgcccggag cgtctgaagc    1500
tgaatcttga ctggcagggg gcgattccgg gatttaacgc cagcgcaggg caaccacact    1560
ggcgcttagg tagcatgggg atggcgcagg cgcggcaggt tatcggtcag cttgagcatg    1620
aaagtagtca gcatgtgccg tttgctaacg aaatggctga gttgctgttc gggcagttgg    1680
tgatgttgct gaatcgccat cgttacacca gtgattcgtt gccgccaaca tccagcgaaa    1740
cgttgctgga taagctgatt acccggctgg cggctagcct gaaaagtccc tttgcgctgg    1800
ataaattttg tgatgaggca tcgtgcagtg agcgcgtttt gcgtcagcaa tttcgccagc    1860
agactggaat gaccatcaat caatatctgc gacaggtcag agtgtgtcat gcgcaatatc    1920
ttctccagca tagccgcctg ttaatcagtg atatttcgac cgaatgtggc tttgaagata    1980 gtaactatt ttcggtggtg tttacccggg aaaccgggat gacgcccagc cagtggcgtc    2040
atctcaattc gcagaaagat taatctagat aaataaaagc agtttacaac tcctagaatt    2100
gtgaatatat tatcacaatt ctaggataga ataataaaag atctctgcag gcatgcaagc    2160
```

```
ttgagtattc tatagtgtca cctaaatagc ttggcgtaat catggtcata gctgtttcct      2220
gtgtgaaatt gttatccgct cacaattcca cacaacatac gagccggaag cataaagtgt      2280
aaagcctggg gtgcctaatg agtgagctaa ctcacattaa ttgcgttgcg ctcactgccc      2340
gctttccagt cgggaaacct gtcgtgccag ctgcattaat gaatcggcca acgcgcgggg      2400
agaggcggtt tgcgtattgg gcgctcttcc gcttcctcgc tcactgactc gctgcgctcg      2460
gtcgttcggc tgcggcgagc ggtatcagct cactcaaagg cggtaatacg gttatccaca      2520
gaatcagggg ataacgcagg aaagaacatg tgagcaaaag gccagcaaaa ggccaggaac      2580
cgtaaaaagg ccgcgttgct ggcgtttttc cataggctcc gcccccctga cgagcatcac      2640
aaaaatcgac gctcaagtca gaggtggcga acccgacag  gactataaag ataccaggcg      2700
tttccccctg gaagctccct cgtgcgctct cctgttccga ccctgccgct taccggatac      2760
ctgtccgcct ttctcccttc gggaagcgtg gcgctttctc atagctcacg ctgtaggtat      2820
ctcagttcgg tgtaggtcgt tcgctccaag ctgggctgtg tgcacgaacc ccccgttcag      2880
cccgaccgct gcgccttatc cggtaactat cgtcttgagt ccaacccggt aagacacgac      2940
ttatcgccac tggcagcagc cactggtaac aggattagca gagcgaggta tgtaggcggt      3000
gctacagagt tcttgaagtg gtggcctaac tacggctaca ctagaagaac agtatttggt      3060
atctgcgctc tgctgaagcc agttaccttc ggaaaaagag ttggtagctc ttgatccggc      3120
aaacaaacca ccgctggtag cggtggtttt tttgtttgca agcagcagat tacgcgcaga      3180
aaaaaaggat ctcaagaaga tcctttgatc ttttctacgg ggtctgacgc tcagtggaac      3240
gaaaactcac gttaagggat tttggtcatg agattatcaa aaaggatctt cacctagatc      3300
cttttaaatt aaaaatgaag ttttaaatca atctaaagta tatatgagta aacttggtct      3360
gacagttacc aatgcttaat cagtgaggca cctatctcag cgatctgtct atttcgttca      3420
tccatagttg cctgactccc cgtcgtgtag ataactacga tacgggaggg cttaccatct      3480
ggccccagtg ctgcaatgat accgcgagac ccacgctcac cggctccaga tttatcagca      3540
ataaaccagc cagccggaag ggccgagcgc agaagtggtc ctgcaacttt atccgcctcc      3600
atccagtcta ttaattgttg ccgggaagct agagtaagta gttcgccagt taatagtttg      3660
cgcaacgttg ttgccattgc tacaggcatc gtggtgtcac gctcgtcgtt tggtatggct      3720
tcattcagct ccggttccca acgatcaagg cgagttacat gatcccccat gttgtgcaaa      3780
aaagcggtta gctccttcgg tcctccgatc gttgtcagaa gtaagttggc cgcagtgtta      3840
tcactcatgg ttatggcagc actgcataat tctcttactg tcatgccatc cgtaagatgc      3900
ttttctgtga ctggtgagta ctcaaccaag tcattctgag aatagtgtat gcggcgaccg      3960
agttgctctt gcccggcgtc aatacgggat aataccgcgc cacatagcag aactttaaaa      4020
gtgctcatca ttggaaaacg ttcttcgggg cgaaaactct caaggatctt accgctgttg      4080
agatccagtt cgatgtaacc cactcgtgca cccaactgat cttcagcatc ttttactttc      4140
accagcgttt ctgggtgagc aaaaacagga aggcaaaatg ccgcaaaaaa gggaataagg      4200
gcgacacgga aatgttgaat actcatactc ttcctttttc aatattattg aagcatttat      4260
cagggttatt gtctcatgag cggatacata tttgaatgta tttagaaaaa taaacaaata      4320
ggggttccgc gcacatttcc ccgaaaagtg ccacctgacg tctaagaaac cattattatc      4380
atgacattaa cctataaaaa taggcgtatc acgaggccct ttcgtctcgc gcgtttcggt      4440
gatgacggtg aaaacctctg acacatgcag ctcccggaga cggtcacagc ttgtctgtaa      4500
gcggatgccg ggagcagaca agcccgtcag ggcgcgtcag cgggtgttgg cgggtgtcgg      4560
```

```
ggctggctta actatgcggc atcagagcag attgtactga gagtgcacca tatgcggtgt    4620
gaaataccgc acagatgcgt aaggagaaaa taccgcatca ggcgccattc gccattcagg    4680
ctgcgcaact gttgggaagg gcgatcggtg cgggcctctt cgctattacg ccagctggcg    4740 aaaggggggat gtgctgcaag gcgattaagt tgggtaacgc cagggttttc ccagtcacga    4800
cgttgtaaaa cgacggccag tgaattgtaa tacgactcac tata                     4844
```

<210> SEQ ID NO 12
<211> LENGTH: 4228
<212> TYPE: DNA
<213> ORGANISM: Artificial Sequence
<220> FEATURE:
<223> OTHER INFORMATION: Synthetic polynucleotide

<400> SEQUENCE: 12

```
gggcgaattc gagctcggta ccctcgagtc cataatcagg taatgccgcg gtgatggat     60 gatgtcgtaa tattgggcac tccctttcag ttgctcaatt atgttatttc acactgctat    120
tgagataatt cacaagtgtg cgctcgctcg caaaataaaa tggaatgatg aaactgggta    180
attccgctag cttttgataa aaattttctc aaagccggtt acgtattacc ggttttgagt    240
ttttgcatga ttcagcagga aaagaaccat gtttactaaa cgtcaccgca tcacattact    300
gttcaatgcc aataaagcct atgaccggca ggtagtagaa ggcgtagggg aatatttaca    360
ggcgtcacaa tcggaatggg atattttcat tgaagaagat ttccgcgccc gcattgataa    420
aatcaaggac tggttaggag atggcgtcat tgccgacttc gacgacaaac agatcgagca    480
agcgctggct gatgtcgacg tccccattgt tggggttggc ggctcgtatc accttgcaga    540
aagttaccca cccgttcatt acattgccac cgataactat cgctggttg aaagcgcatt     600 tttgcattta aaagagaaag cgttaaccg ctttgctttt tatggtcttc cggaatcaag     660
cggcaaacgt tgggccactg agcgcgaata tgcatttcgt cagcttgtcg ccgaagaaaa    720
gtatcgcgga gtggtttatc aggggttaga accgcgcca gagaactggc aacacgcgca    780
aaatcggctg gcagactggc tacaaacgct accaccgcaa accgggatta ttgccgttac    840
tgacgcccga gcgcggcata ttctgcaagt atgtgaacat ctacatattc ccgtaccgga    900
aaaattatgc gtgattggca tcgataacga agaactgacc cgctatctgt cgcgtgtcgc    960
cctttcttcg gtcgctcagg gcgcgcggca aatgggctat caggcggcaa aactgttgca    1020
tcgattatta gataaagaag aaatgccgct acagcgaatt ttggtcccac cagttcgcgt    1080
cattgaacgg cgctcaacag attatcgctc gctgaccgat cccgccgtta ttcaggccat    1140
gcattacatt cgtaatcacg cctgtaaagg gattaaagtg gatcaggtac tggatgcggt    1200
cgggatctcg cgctccaatc ttgagaagcg ttttaaagaa gaggtgggtg aaaccatcca    1260
tgccatgatt catgccgaga gctggagaa agcgcgcagt ctgctgattt caaccacctt    1320
gtcgatcaat gagatatcgc aaatgtgcgg ttatccatcg ctgcaatatt tctactctgt    1380
ttttaaaaaa gcatatgaca cgacgccaaa agagtatcgc gatgtaaata gcgaggtcat    1440
gttgtaattc tagataaata aaagcagttt acaactccta gaattgtgaa tatattatca    1500
caattctagg atagaataat aaaagatctc tgcaggcatg caagcttgag tattctatag    1560
tgtcacctaa atagcttggc gtaatcatgg tcatagctgt ttcctgtgtg aaattgttat    1620
ccgctcacaa ttccacacaa catacgagcc ggaagcataa agtgtaaagc ctgggtgcct    1680
aatgagtgag ctaactcaca ttaattgcgt tgcgctcact gcccgctttc cagtcgggaa    1740
```

```
acctgtcgtg ccagctgcat taatgaatcg gccaacgcgc ggggagaggc ggtttgcgta    1800
ttgggcgctc ttccgcttcc tcgctcactg actcgctgcg ctcggtcgtt cggctgcggc    1860
gagcggtatc agctcactca aaggcggtaa tacggttatc cacagaatca ggggataacg    1920
caggaaagaa catgtgagca aaaggccagc aaaaggccag gaaccgtaaa aaggccgcgt    1980
tgctggcgtt tttccatagg ctccgccccc ctgacgagca tcacaaaaat cgacgctcaa    2040
gtcagaggtg gcgaaacccg acaggactat aaagatacca ggcgtttccc cctggaagct    2100
ccctcgtgcg ctctcctgtt ccgaccctgc cgcttaccgg atacctgtcc gcctttctcc    2160
cttcgggaag cgtggcgctt tctcatagct cacgctgtag gtatctcagt tcggtgtagg    2220
tcgttcgctc caagctgggc tgtgtgcacg aaccccccgt tcagcccgac cgctgcgcct    2280
tatccggtaa ctatcgtctt gagtccaacc cggtaagaca cgacttatcg ccactggcag    2340
cagccactgg taacaggatt agcagagcga ggtatgtagg cggtgctaca gagttcttga    2400
agtggtggcc taactacggc tacactagaa gaacagtatt tggtatctgc gctctgctga    2460
agccagttac cttcggaaaa agagttggta gctcttgatc cggcaaacaa accaccgctg    2520
gtagcggtgg tttttttgtt tgcaagcagc agattacgcg cagaaaaaaa ggatctcaag    2580
aagatccttt gatcttttct acggggtctg acgctcagtg gaacgaaaac tcacgttaag    2640
ggattttggt catgagatta tcaaaaagga tcttcaccta gatcctttta aattaaaaat    2700
gaagttttaa atcaatctaa agtatatatg agtaaacttg gtctgacagt taccaatgct    2760
taatcagtga ggcacctatc tcagcgatct gtctatttcg ttcatccata gttgcctgac    2820
tccccgtcgt gtagataact acgatacggg agggcttacc atctggcccc agtgctgcaa    2880
tgataccgcg agacccacgc tcaccggctc cagatttatc agcaataaac cagccagccg    2940
gaagggccga gcgcagaagt ggtcctgcaa ctttatccgc ctccatccag tctattaatt    3000
gttgccggga agctagagta agtagttcgc cagttaatag tttgcgcaac gttgttgcca    3060
ttgctacagg catcgtggtg tcacgctcgt cgtttggtat ggcttcattc agctccggtt    3120
cccaacgatc aaggcgagtt acatgatccc ccatgttgtg caaaaaagcg gttagctcct    3180
tcggtcctcc gatcgttgtc agaagtaagt tggccgcagt gttatcactc atggttatgg    3240
cagcactgca taattctctt actgtcatgc catccgtaag atgcttttct gtgactggtg    3300
agtactcaac caagtcattc tgagaatagt gtatgcggcg accgagttgc tcttgcccgg    3360
cgtcaatacg ggataatacc gcgccacata gcagaacttt aaaagtgctc atcattggaa    3420
aacgttcttc ggggcgaaaa ctctcaagga tcttaccgct gttgagatcc agttcgatgt    3480
aacccactcg tgcacccaac tgatcttcag catcttttac tttcaccagc gtttctgggt    3540
gagcaaaaac aggaaggcaa aatgccgcaa aaagggaat aagggcgaca cggaaatgtt    3600
gaatactcat actcttcctt tttcaatatt attgaagcat ttatcagggt tattgtctca    3660
tgagcggata catatttgaa tgtatttaga aaaataaaca ataggggtt ccgcgcacat    3720 ttccccgaaa agtgccacct gacgtctaag aaaccattat tatcatgaca ttaacctata    3780
aaaataggcg tatcacgagg ccctttcgtc tcgcgcgttt cggtgatgac ggtgaaaacc    3840
tctgacacat gcagctcccg gagacggtca gcttgtctg taagcggat gccgggagca    3900 gacaagcccg tcagggcgcg tcagcgggtg ttggcgggtg tcgggctgg cttaactatg    3960 cggcatcaga gcagattgta ctgagagtgc accatatgcg gtgtgaaata ccgcacagat    4020
gcgtaaggag aaaataccgc atcaggcgcc attcgccatt caggctgcgc aactgttggg    4080
aagggcgatc ggtgcgggcc tcttcgctat tacgccagct ggcgaaaggg ggatgtgctg    4140
```

```
caaggcgatt aagttgggta acgccagggt tttcccagtc acgacgttgt aaaacgacgg    4200
ccagtgaatt gtaatacgac tcactata                                       4228
```

INDUCTION OF PROTECTIVE IMMUNITY AGAINST ANTIGENS

RELATED APPLICATIONS

This application is a continuation of U.S. patent application Ser. No. 16/480,253, filed on Jul. 23, 2019, which in turn, is a 35 U.S.C. § 371 national stage filing of International Application No. PCT/US2018/014860, filed on Jan. 23, 2018, which in turn claims priority to U.S. Provisional Application No. 62/449,228, filed on Jan. 23, 2017 and U.S. Provisional Application No. 62/541,293, filed on Aug. 4, 2017. The entire contents of each of the foregoing applications is expressly incorporated by reference herein.

This invention was made with government support under Grant Nos. AI093348, AI056289 and AI126712, awarded by The National Institutes of Health. The government has certain rights in the invention.

The Sequence Listing for this application is labeled "Seq-List.txt" which was created on Jan. 23, 2018 and is 31 KB. The entire content of the sequence listing is incorporated herein by reference in its entirety.

BACKGROUND

*Salmonella enterica* causes heavily burdened diseases in humans worldwide. S. Typhi and Paratyphi A, B and C cause enteric fever (1) and are major public health concerns (2-4). S. Typhi is estimated to cause over 20.6 million cases, 433,000 deaths globally each year (5, 6) and 12.2 million disability-adjusted life years (7). In addition to these serovars, nontyphoidal *Salmonella* (NTS) is increasingly being recognized as important causes of invasive diseases (2, 8, 9), such as sepsis and meningitis, with 93.8 million cases and 681,300 deaths annually globally (10, 11). NTS is also a leading cause of hospitalization and death from food borne disease in the US (12), ~1.2 million cases of inflammatory diarrheal disease per year, resulting in 23,000 hospitalizations and 450 deaths (12, 13) with an economic loss of approximately $3.31 billion due to premature mortality, disability, medical and productivity costs and an annual loss of 16,782 quality-adjusted life years (14). Among children <5 years old, NTS is the top bacterial pathogen and causes 4670 hospitalization and 38 deaths (15). NTS disease in the US is accounted primarily by serovars belonging to three serovars B, D and C (16). Serovars Enteritidis, Typhimurium, Newport, and Heidelberg are the most common outbreaks in the US (17). Though the vast majority of patients develop self-limiting gastroenteritis, characterized by inflammatory diarrhea, NTS can also cause systemic diseases and is the single most common cause of death from foodborne illnesses associated with viruses, parasites or bacteria in the US primarily in immunocompromised persons (18). In young children and HIV-infected individuals, NTS frequently causes systemic infection that is associated with high mortality (19). The rise of AIDS in many parts of the world, notably in sub-Saharan Africa, has resulted in a dramatic increase in the frequency of NTS-associated systemic infection (20, 21). Bacteremia is the most severe symptom and mortality in bacteremic children who reach a clinic can be nearly 25% (18, 21). Enteric fever and NTS become increasingly difficult to treat with antibiotics because of the rise in *Salmonella* of multi-drug resistance (22, 23), leading to the risk of an increasing number of untreatable cases (24, 25).

Enteric fever can be prevented with several vaccines (26, 27). Killed whole cell preparations of serovars Typhi and Paratyphi were effective in diminishing the incidence in endemic areas (28), but were discontinued due to frequent adverse reactions (29). A live attenuated S. Typhi strain Ty21a, generated by chemical mutagenesis, confers only a moderate level of protection for up to three years against serovar Typhi, but not other relevant serovars (29, 30). Additional genetically modified *Salmonella* strains have been tested in clinical trials with some success, but none of them has been approved. The purified capsular carbohydrate Vi of serovar Typhi induces protective immunity over several years against Typhi and possibly Paratyphi C, but not against Paratyphi A and B or Typhimurium that all lack this capsule (31). Conjugation of Vi with a protein antigen improves immune responses in infants, a major susceptible population for enteric fever.

To cover the important serovar Paratyphi A, current efforts focus on linking the O-antigen, the carbohydrate part of lipopolysaccharide (LPS), with a protein antigen (27). These two commercial vaccines are mainly used for the traveler vaccine market and no new vaccine for widespread use has been licensed since the 1990s (26). Although three types of vaccines against S. Typhi are currently commercially available, unfortunately, there is still not a single licensed vaccine available against S. Paratyphi A, with very little, if any, cross-protection provided by the available S. Typhi vaccines. There are vaccines against NTS serovars Enteritidis and Typhimurium which are effective in farm animals, like poultry and pigs (32), but not available in humans (33). This represents a significant limitation in the existing prevention strategies. Therefore, treatment for systemic salmonellosis has become increasingly difficult, and current vaccines against *Salmonella* only provide at moderated levels, limited duration of protection, and limited coverage of clinically relevant serovars. These situations generate an urgent medical need for improved *Salmonella* vaccines.

The use of recombinant attenuated *Salmonella* vaccines (RASVs) as a vaccine or a heterologous antigen delivery system has been studied because of their abilities to stimulate systemic and mucosal immune responses at local and distal sites and advantages as vectors to produce and present recombinant vaccine antigens. RASVs can be used for a multitude of applications including, but not limited to, vaccination against pathogens that cause disease, cancer, chronic respiratory disease, and heart disease. Recently, Regulated Delayed Attenuated RASVs (RDA RASVs) have been developed to enhance the immune responses to RASVs and the protective antigen carried. RDA RASVs are engineered so that genes for key virulence factors are under the control of an inducible promoter PaaBAD, induced by arabinose not found in the mammalian host. The RDA RASVs are grown in vitro in the presence of arabinose so that genes mediating the pathogenic phenotype are expressed and RASVs display features of wild-type to invade into the hosts. Expression of the pathogenic genes ceases due to the absence of arabinose in vivo, with gene products diluted due to replication, producing an attenuated phenotype without causing disease. Since they replicate initially with full virulence, they colonize lymphoid tissues to higher levels to elicit more potent immune responses than a constitutively attenuated RASV.

Regulated delayed protein synthesis (RDPS) have also been developed to enhance immunogenicity. The increased antigen synthesis levels help to increase the chance that cognate T cells interact with antigen presentation cells (APCs), leading to effective proliferation and production of effector molecules and T-cell proliferation in vivo. However, high-level antigen synthesis imposes metabolic demands that impair the strains' ability to colonize effector lymphoid tissues. An RDPS system makes recombinant vaccine antigen production only after the RASV colonizes lymphoid tissues as the RASV cells multiply in vivo. This strategy is not influenced by the mode of attenuation.

Although the use of recombinant *Salmonella* as live vaccines to produce an immune response in subjects is promising, the organisms are live and sometimes pathogenic. Accordingly, it is necessary to introduce regulatory systems into the bacteria to attenuate and control the expression of antigens that are expressed by the bacteria. The currently utilized means of attenuation make live vaccine strains susceptible to environmental stresses in vivo. Consequently, fewer bacteria are able to colonize the host cell in order to achieve a desirable level of immunogenicity. Thus, there is a need for new strains of recombinant microorganisms that can be developed for use as live vaccines, which are less susceptible to environmental stresses in vivo and which can colonize host cells in order to achieve better levels of immunogenicity. There is also a need for new means to enhance the safety of live attenuated vaccines in vivo.

SUMMARY

The instant disclosure provides strains of recombinant bacteria, including *Salmonella*, which depend on three sugars to regulate the virulence phenotype of the bacteria by controlling the expression of multiple virulence genes and of an antigen of interest, as well as a regulated delayed lysis phenotype, allowing for biological containment and the enhancement of immunogenic properties. Other attributes that can be regulated by one or more of the sugars includes acid tolerance during (e.g., during oral immunization) as described in U.S. Patent Application Publication No. 2014/0370057, the entire contents of which are expressly incorporated herein by reference. The dependence on three sugars enhances the safety of the recombinant bacteria, given the improbability that the organisms will encounter all three sugars in a naturally-occurring environment. Surprisingly, the instant invention demonstrates that three distinct sugars could successfully be used to regulate attributes of the recombinant bacteria (e.g., the expression of genes encoding an antigen of interest, delayed lysis phenotype and/or virulence gene expression) without cross-interference of any one sugar in the sugar-regulatable activity of any other sugar by catabolite repression.

The organisms can be used for the safe and highly effective delivery of antigenic compounds to a subject in order to mount effective protective immune responses. Such recombinant bacteria can manipulate cell surface synthesizing protective antigens and can induce protective immune responses to multiple *Salmonella* serovars. The recombinant bacteria can be used to enhance survival of the bacteria to host defense stresses such as stomach acid; to confer regulated delayed attenuation; to confer regulated-delayed lysis in vivo (e.g., by control of asdA and murA gene expression with release of an antigen of interest or of a DNA vaccine encoding them); or to enable fusion of carbohydrate polymers onto carbohydrate and/or proteins.

Specifically, disclosed herein are triple sugar regulated Recombinant Attenuated *Salmonella* Vaccine (RASV) strains. These strains deliver multiple conserved protective *Salmonella* surface secreted antigens with their natural conformations to induce protective immunity against multiple virulent *Salmonella* serovars. As an example, the RASVs may have a rhamnose-regulated O-antigen synthesis, combined with a mannose-regulated O-antigen side chain synthesis to expose conserved inner core, and an arabinose-regulated production of Generalized Modules for Membrane Antigens (GMMA), or outer membrane vesicles, in vivo for enhancing production of conserved outer membrane proteins (OMPs). RASVs may be constructed in two *Salmonella* serovars, group B S. Typhimurium and group D S. Enteritidis, to express conserved immunogen genes and to maximize anti-*Salmonella* humoral, cellular and mucosal immune responses. The disclosed RASVs have rational design features different from other RASVs that enhance success. Specifically, the disclosed RASVs provide safe and highly effective *Salmonella* vaccines with low cost and can be used to develop S. Typhi or S. Paratyphi A RASVs for human use.

In one aspect, the disclosure provides a recombinant derivative of a pathogenic bacterium comprising: a.) a first gene regulated by a first sugar which confers a first phenotype; b.) a second gene regulated by a second sugar which confers a second phenotype; and c.) a third gene regulated by a third sugar which confers a third phenotype; wherein the first, second and third phenotypes are selected from the group consisting of: 1. a regulated-delayed attenuation; 2. a regulated-delayed expression of an antigen of interest; 3. a regulated-delayed lysis in vivo; 4. a regulated synthesis of O-antigen; 5. a regulated synthesis of an O-antigen side chain; 6. a regulated production of Generalized Modules for Membrane Antigens (GMMA); 7. regulated enhanced survival to a host stress condition; and 8. a regulated production of outer membrane vesicles (OMVs).

In one aspect, the disclosure provides a recombinant derivative of a pathogenic bacterium comprising: a.) a first gene regulated by a first sugar which confers a first phenotype; b.) a second gene regulated by a second sugar which confers a second phenotype; and c.) a third gene regulated by a third sugar which confers a third phenotype; wherein the first, second and third phenotypes are selected from the group consisting of: 1. a regulated-delayed attenuation; 2. a regulated-delayed expression of an antigen of interest; 3. a regulated-delayed lysis in vivo; 4. a regulated synthesis of O-antigen; 5. a regulated production of Generalized Modules for Membrane Antigens (GMMA); 6. regulated enhanced survival to a host stress condition; and 7. a regulated production of outer membrane vesicles (OMVs).

In one embodiment, the first sugar, second sugar, and third sugar are each a different sugar. In one embodiment, the first sugar, second sugar, or third sugar does not interfere with the regulation of a gene regulated by a different sugar.

In one embodiment, the first sugar is selected from the group consisting of arabinose, mannose, xylose, galactose, rhamnose, and maltose. In one embodiment, the second sugar is selected from the group consisting of arabinose, mannose, xylose, galactose, rhamnose, and maltose. In one embodiment, the third sugar is selected from the group consisting of arabinose, mannose, xylose, galactose, rhamnose, and maltose.

In one embodiment, the first gene is operably-linked to a first sugar-regulatable promoter. In one embodiment, the second gene is operably-linked to a second sugar-regulatable promoter. In one embodiment, the third gene is operably-linked to a third sugar-regulatable promoter.

In one embodiment, a gene is modified to enable a reversible synthesis of a sugar-containing molecule that confers a sugar regulatable phenotype. In one embodiment, the modified gene is pmi. In one embodiment, the modified gene is galE.

In one embodiment, the bacterium is a Gram-negative bacterium. In one embodiment, the bacterium belongs to the family Enterobacteriaceae.

In one embodiment, the phenotype is regulated-delayed attenuation, and the gene conferring the phenotype is fur. In one embodiment, the phenotype is regulated-delayed expression of an antigen of interest, and the gene conferring the phenotype encodes an antigen of interest. In one embodiment, the phenotype is the regulated-delayed lysis in vivo, wherein the lysis is enabled to occur in a cytosol due to mutation in a sifA gene. In one embodiment, the phenotype is regulated synthesis of O-antigen, and the gene conferring the phenotype is selected from the group consisting of waaG, rfaH, waaJ, wbaP, wzy, waaP, waaO, waaF, waaP, waaC, waaA, waaL and wbaP. In one embodiment, the phenotype is production of Generalized Modules for Membrane Antigens (GMMA) or outer membrane vesicles, and the gene conferring the phenotype is selected from the group consisting of ybgC, tolQ, tolA, tolR, tolB, paI, and ybgF.

In one embodiment, the phenotype is regulated synthesis of O-antigen side chain, and the gene conferring the phenotype is tolR. In one embodiment, the first phenotype is regulated O-antigen synthesis and the second phenotype is production of GMMA or outer membrane vesicles.

In one embodiment, the bacterium further comprises a gene encoding an antigen of interest not operably-linked to a sugar regulatable promoter.

In one embodiment, the bacterium comprises a deletion of an endogenous O-antigen synthesis gene. In one embodiment, the deletion in the endogenous O-antigen synthesis gene comprises a partial deletion of the gene. In one embodiment, the deletion in the endogenous O-antigen synthesis gene comprises a full-length deletion of the gene. In one embodiment, the O-antigen synthesis gene is waaL or wbaP.

In one embodiment, the bacterium comprises a deletion in an endogenous phosphomannose isomerase gene. In one embodiment, the deletion in the endogenous phosphomannose isomerase gene comprises a partial deletion of the gene. In one embodiment, the deletion in the endogenous phosphomannose isomerase gene comprises a full-length deletion of the gene. In one embodiment, the phosphomannose isomerase gene is pmi.

In one embodiment, the bacterium comprises a deletion in an endogenous tol-pal system gene. In one embodiment, the deletion in the endogenous tol-pal system gene comprises a partial deletion of the gene. In one embodiment, the deletion in the endogenous tol-pal system gene comprises a full-length deletion of the gene. In one embodiment, the endogenous tol-pal system gene is selected from the group consisting of ybgC, tolQ, tolA, tolR, tolB, paI, and ybgF.

In one embodiment, the first gene, second gene and/or third gene is located on a plasmid in the bacterium. In one embodiment, the first gene, second gene and/or third gene is located on a chromosome in the bacterium.

In one embodiment, the first, second or third sugar-regulatable promoter is a rhamnose-regulatable promoter. In one embodiment, the rhamnose-regulatable promoter is rhaSR $P_{rhaBAD}$.

In one embodiment, the first, second or third sugar-regulatable promoter is an arabinose-regulatable promoter. In one embodiment, the arabinose regulatable promoter is araC $P_{araBAD}$.

In one embodiment, the bacterium further comprises a deletion in an endogenous relA gene. In one embodiment, the deletion of the endogenous relA gene is a partial deletion of the gene. In one embodiment, the deletion of the endogenous relA gene is a full-length deletion of the gene.

In one embodiment, the bacterium further comprises a nucleic acid encoding a LacI repressor. In one embodiment, the LacI repressor is encoded by a lacI gene. In one embodiment, the nucleic acid encoding the LacI repressor is located on a plasmid in the bacterium. In one embodiment, the nucleic acid encoding the LacI repressor is located on a chromosome in the bacterium.

In one embodiment, the bacterium further comprises a deletion in an endogenous $P_{fur}$ promoter.

In one embodiment, the fur gene is operably-linked to an arabinose-regulatable promoter. In one embodiment, the fur gene is located on a plasmid in the bacterium. In one embodiment, the fur gene is located on a chromosome in the bacterium.

In one embodiment, the bacterium further comprises a deletion in gene encoding an aspartate-semialdehyde dehydrogenase. In one embodiment, the gene encoding the aspartate-semialdehyde dehydrogenase comprises an asd gene. In one embodiment, the gene encoding the aspartate-semialdehyde dehydrogenase comprises an asdA gene.

In one embodiment, the gene encoding the antigen of interest is located in a plasmid in the bacterium. In one embodiment, the plasmid further comprises a nucleic acid encoding an aspartate-semialdehyde dehydrogenase. In one embodiment, the aspartate-semialdehyde dehydrogenase comprises AsdA. In one embodiment, the plasmid is a low copy number plasmid. In one embodiment, the plasmid is a high copy number plasmid. In one embodiment, the plasmid is selected from the group consisting of pYA4589, pYA4595, pYA4763, pG8R15, pG8R16, pG8R17, pG8R18, pGR111, pG8R112, pG8R113, and pG8R114.

In one embodiment, the gene encoding the antigen of interest is located on a chromosome in the bacterium.

In one embodiment, the bacterium further comprises a deletion in a pagL gene. In one embodiment, the deletion of the pagL gene is a partial deletion of the gene. In one embodiment, the deletion of the pagL gene is a full-length deletion of the gene. In one embodiment, the mutation is ΔwaaL/ΔpagL::TT rhaSR $P_{rhaBAD}$ waaL.

In one embodiment, the bacterium further comprises an antigen of interest operably-linked to a repressor-regulatable promoter. In one embodiment, the promoter is a lactose-regulatable promoter. In one embodiment, the lactose-regulatable promoter is a LacI-regulatable promoter. In one embodiment, the LacI-regulatable promoter is selected from the group consisting of $P_{trc}$, $P_{lac}$, $P_{T7lac}$, $P_{tac}$, $P_{ompA\ lacO}$, and $P_{lpp\ lacO}$.

In one embodiment, the antigen of interest is an antigen derived from an infectious agent. In one embodiment, the antigen of interest is derived from an infectious agent selected from the group consisting of a virus, a bacterium, a protozoan, a prion, a fungus, and a helminth. In one embodiment, the antigen of interest is derived from a bacterium. In one embodiment, the antigen of interest is a *Salmonella* antigen. In one embodiment, the *Salmonella* antigen is selected from the group FliC, FliC180, OmpC, OmpD, OmpF, SseB, and SseI. In one embodiment, the antigen of interest is an antigen from a *Clostridium* bacterium. In one embodiment, the antigen is a *C. perfringens* antigen. In one embodiment, the antigen comprises NetB, PlcC, antigenic fragments thereof, fusion proteins comprising said antigens, or fusion proteins comprising antigenic fragments of antigens.

In one embodiment, the antigen of interest is a viral antigen. In one embodiment, the antigen of interest is an influenza antigen. In one embodiment, the influenza antigen is hemagglutinin or neuraminidase.

In one embodiment, the antigen of interest is an antigen associated with cancer. In one embodiment, the antigen associated with cancer is selected from the group consisting of MAGE-A, MAGE-C1, BAGE, GAGE, CAGE, XAGE, NY-ESO1, LAGE1, and survivin.

In one embodiment, the antigen is a protein antigen encoded by a nucleic acid sequence codon optimized for expression in said bacterium.

In one embodiment, the bacterium further comprises a deletion in a sifA gene. In one embodiment, the deletion of the sifA gene is a partial deletion of the gene. In one embodiment, the deletion of the sifA gene is a full-length deletion of the gene. In one embodiment, the sifA gene is operably-linked to an arabinose-regulatable promoter.

In one embodiment, the bacterium further comprises a deletion in a recF gene. In one embodiment, the deletion of the recF gene is a partial deletion of the gene. In one embodiment, the deletion of the recF gene is a full-length deletion of the gene.

In one embodiment, the bacterium further comprises a deletion in a recJ gene. In one embodiment, the deletion of the recJ gene is a partial deletion of the gene. In one embodiment, the deletion of the recJ gene is a full-length deletion of the gene.

In one embodiment, the bacterium is of the genus *Salmonella*. In one embodiment, the bacterium is a *Salmonella enterica* bacterium. In one embodiment, the bacterium is a *Salmonella enterica* subsp. *enterica* serovar Paratyphi A bacterium, a *Salmonella enterica* subsp. *enterica* serovar Enteritidis bacterium, a *Salmonella enterica* subsp. *enterica* serovar Typhi bacterium, a *Salmonella enterica* subsp. *enterica* serovar Typhimurium bacterium, *Salmonella enterica* subsp. *enterica* serovar Dublin, or *Salmonella enterica* subsp. *enterica* serovar Choleraesuis.

In another aspect, disclosed herein is a pharmaceutical composition comprising a recombinant bacterium disclosed herein, and a pharmaceutically acceptable carrier.

In another aspect, disclosed herein is a method for eliciting an immune response against an antigen of interest in a subject, the method comprising administering to the subject an effective amount of a pharmaceutical composition disclosed herein.

Other aspects and iterations of the invention are described more thoroughly below.

BRIEF DESCRIPTION OF THE FIGURES

FIGS. 3A, 3B, and 3C depict galactose-insensitive mutation Δ(galE-ybhC)-851.

FIGS. 4A, 4B, 4C, 4D, 4E, 4F, 4G, and 4H depict growth curves of *Salmonella* strains with different galE mutations in Nutrient broth with varying concentrations of galactose.

FIGS. 6A, 6B, 6C, 6D, 6E, 6F, 6G, 6H, 6I, 6J, 6K, 6L, 6M, 6N, 6O, 6P, 6Q, and 6R depict growth curves of *Salmonella* strains χ12341(pYA4763) and χ3761 during 24 h in growth media with varying sugar concentrations as indicated.

DETAILED DESCRIPTION

Figure 1:
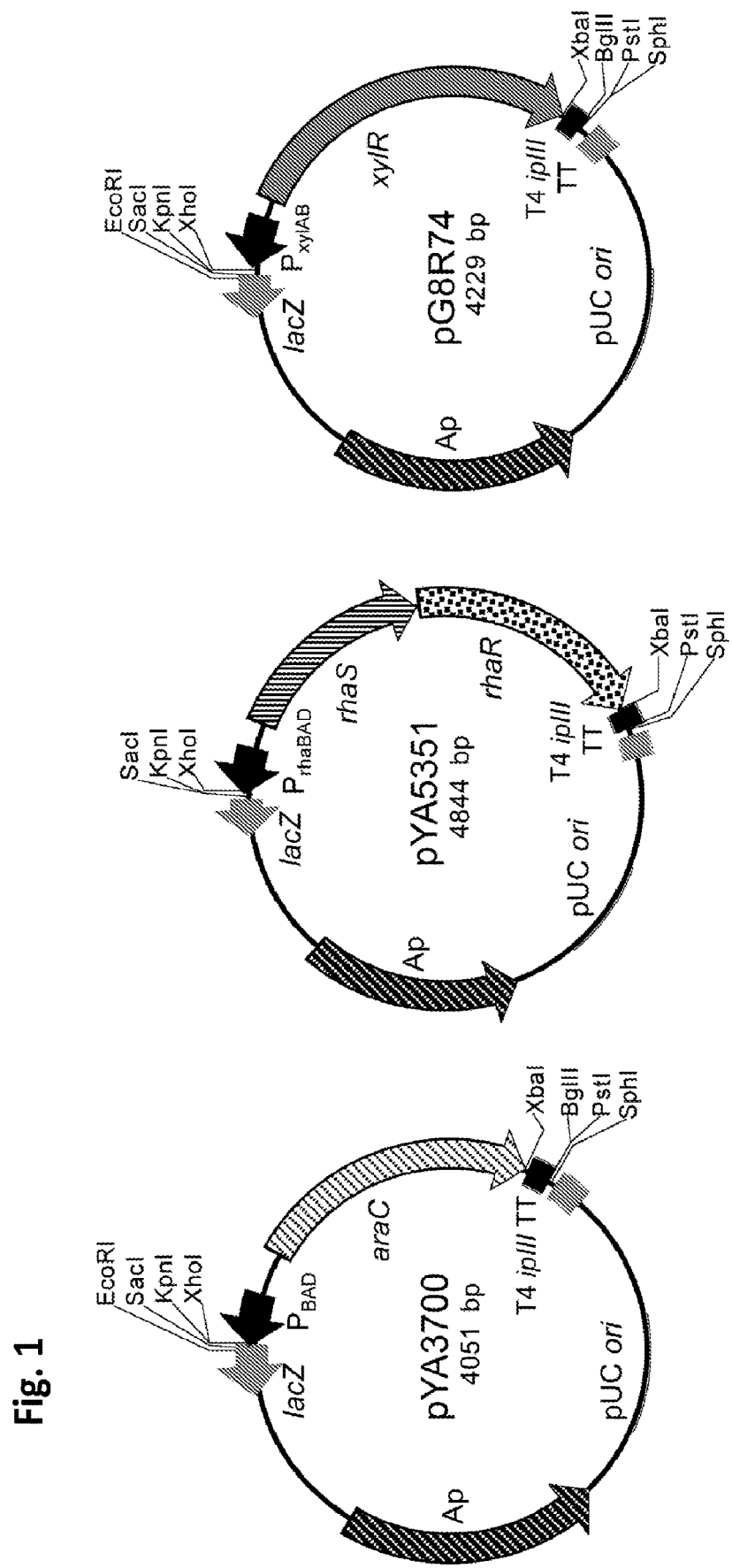
FIG. 1. Depicts three vectors containing the sugar-regulated cassettes araC $P_{araBAD}$, rhaRS-$P_{rhaBAD}$ and xylR-$P_{xylA}$ to enable construction of a suicide vector derivative to generate fusions of a sugar regulation cassette to a gene of interest for the replacement of the native promoter for that gene of interest.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

As used herein, the term "recombinant bacterium" refers to a bacterial cell that has been genetically modified from its native state. For instance, a recombinant bacterium may comprise one or more nucleotide insertions, nucleotide deletions, nucleotide rearrangements, and nucleotide modifications. These genetic modifications may be introduced into the chromosome of the bacterium, or alternatively be present on an extrachromosomal nucleic acid (e.g., a plasmid). Recombinant bacteria of the disclosure may comprise a nucleic acid located on a plasmid. Alternatively, the recombinant bacteria may comprise a nucleic acid located in the bacterial chromosome (e.g., stably incorporated therein). In some embodiments, the recombinant bacterium is avirulent. In some embodiments the recombinant bacterium exhibits reduced virulence. In some embodiments, the recombinant bacterium is non-virulent. In some embodiments, the recombinant bacterium is pathogenic. In some embodiments, the recombinant bacterium is attenuated. In another embodiment, the recombinant bacterium is a recombinant derivative of a pathogenic bacterium.

As used herein, the term "gene" refers to a nucleic acid fragment that encodes a protein or a fragment thereof, or a functional or structural RNA molecule, and may optionally include a regulatory sequence preceding (5' non-coding sequences) and following (3' non-coding sequences) the coding sequence of the nucleic acid. In some embodiments, a "gene" does not include regulatory sequences preceding and following the coding sequence.

In one embodiment, the gene is a heterologous gene. In another embodiment, the nucleic acid is a heterologous nucleic acid. As used herein, the terms "heterologous gene" or "heterologous nucleic acid" refer to a gene or a nucleic acid sequence present in a recombinant cell, e.g., bacterium, that is not normally found in the wild-type cell, e.g., bacterium, in nature. In some embodiments, the heterologous gene or heterologous nucleic acid is exogenously introduced into a given cell. In some embodiments, a heterologous gene may include a gene, or fragment thereof, introduced into a non-native host cell. In some embodiments, the term "heterologous gene" includes a second copy of a native gene, or fragment thereof, that has been introduced into the host cell in addition to the corresponding native gene. A heterologous nucleic acid may also include, in some embodiments, a gene sequence that is naturally-found in a given cell but which has been modified, e.g., by regulation by a different promoter sequence, to expresses an unnatural amount of the nucleic acid and/or the polypeptide which it encodes; and/or two or more nucleic acid sequences that are not found in the same relationship to each other in nature.

As used herein, the term "endogenous gene" refers to a native gene that is present in its natural location in the genome of an organism (e.g., a bacterial chromosome).

A "promoter" as used herein, refers to a nucleic acid sequence that is capable of controlling the expression of a coding sequence or gene. A promoter may comprise one or more specific transcriptional regulatory sequences to further enhance expression and/or to alter the spatial expression and/or temporal expression of a nucleic acid. For example, a promoter may include one or more nucleic acids that are specifically recognized by a transcriptional activator protein (e.g., an enhancer element), a transcriptional repressor protein, a polymerase, and the like. The term "operably linked," as used herein, means that expression of a nucleic acid sequence is under the control of a promoter with which it is spatially connected. A promoter may be positioned 5' (upstream) of the nucleic acid sequence under its control. The distance between the promoter and a nucleic acid sequence to be expressed may be approximately the same as the distance between that promoter and the native nucleic acid sequence it controls. As is known in the art, variation in this distance may be accommodated without loss of promoter function. The nucleic acid sequences of the promoters described herein are known in the art, and methods of operably-linking these promoters to a gene (e.g., a gene encoding a repressor) are known in the art.

In some embodiments, the promoter for use as described herein may be regulated directly or indirectly by a sugar. For example, in some embodiments, the promoter is responsive to the level of arabinose, otherwise referred to herein as an "arabinose-regulatable promoter". Generally speaking, arabinose may be present during the in vitro growth of a bacterium, while typically absent from host tissue. In one embodiment, the promoter is derived from an araC-$P_{araBAD}$ system from *Escherichia coli*. The araC $P_{araBAD}$ system is a tightly regulated expression system, which has been shown to work as a strong promoter induced by the addition of low levels of arabinose. The araC-araBAD promoter is a bidirectional promoter controlling expression of the araBAD nucleic acid sequences in one direction, and the araC nucleic acid sequence in the other direction.

For convenience, the portion of the araC-araBAD promoter that mediates expression of the araBAD nucleic acid sequences, and which is controlled by the araC nucleic acid sequence product, is referred to herein as $P_{araBAD}$. For use as described herein, a cassette with the araC nucleic acid sequence and the araC-araBAD promoter may be used. This cassette is referred to herein as araC $P_{araBAD}$. The AraC protein is both a positive and negative regulator of $P_{araBAD}$. In the presence of arabinose, the AraC protein is a positive regulatory element that allows expression from $P_{araBAD}$. In the absence of arabinose, the AraC protein represses expression from $P_{araBAD}$. Other enteric bacteria contain arabinose regulatory systems homologous to the araC-araBAD system from *E. coli*, including, for example, S. Typhimurium. For example, the *E. coli* AraC protein only activates *E. coli* $P_{araBAD}$ (in the presence of arabinose) and not S. Typhimurium $P_{araBAD}$. Thus, an arabinose regulated promoter may be used in a recombinant bacterium that possesses a similar arabinose operon, without substantial interference between the two, if the promoter and the operon are derived from two different species of bacteria. Generally speaking, the concentration of arabinose necessary to induce expression is typically less than about 2% (w/w) in a culture media. In some embodiments, the concentration is less than about 1.5%, 1%, 0.5%, 0.2%, 0.1%, or 0.05% (w/w) in a culture media. In other embodiments, the concentration is 0.05% or below, e.g. about 0.04%, 0.03%, 0.02%, or 0.01% (w/w). In an exemplary embodiment, the concentration is about 0.05% (w/w) in a culture media.

In other embodiments, the promoter may be responsive to the level of maltose in the environment, otherwise referred to herein as a "maltose-regulatable promoter". In some embodiments, the recombinant bacteria described herein are cultured in a medium comprising maltose. The malT gene encodes MalT, a positive regulator of four maltose-responsive promoters ($P_{PQ}$, $P_{EFG}$, $P_{KBM}$, and $P_S$). The combination of malT and a mal promoter creates a tightly regulated expression system that has been shown to work as a strong promoter induced in the presence of maltose. Unlike the araC-$P_{araBAD}$ system, malT expression is regulated by a promoter (i.e., $P_T$) that is functionally unrelated to the other mal promoters. $P_T$ is not regulated by MalT. The malEFG-malKBM promoter is a bidirectional promoter that controls expression of the malKBM nucleic acid sequences in one direction, and the malEFG nucleic acid sequences in the other direction. For convenience, the portion of the malEFG-malKBM promoter that mediates expression of the malKBM nucleic acid sequence, and which is controlled by MalT, is referred to herein as $P_{KBM}$, and the portion of the malEFG-malKBM promoter that mediates expression of the malEFG nucleic acid sequence, and which is controlled by MalT, is referred to herein as $P_{EFG}$. Full induction of $P_{KBM}$ requires the presence of the MalT binding sites of $P_{EFG}$. For use in the vectors and systems described herein, a gene cassette comprising a nucleic acid sequence encoding MalT and a mal promoter may be used. This gene cassette is referred to herein as malT-$P_{mal}$. In the presence of maltose, the MalT is a positive regulatory element that allows for expression mediated by $P_{mal}$. Generally speaking, the concentration of maltose necessary to induce expression is typically less than about 1% (w/w) in a culture media. In some embodiments, the concentration is less than about 1.0%, 0.9%, 0.8%, 0.7%, 0.6%, 0.5%, 0.4%, 0.3% 0.2%, 0.1%, or 0.05% (w/w) in a culture media. In other embodiments, the concentration is 0.05% or below, e.g. about 0.04%, 0.03%, 0.02%, or 0.01% (w/w). In an exemplary embodiment, the concentration is about 0.2% to about 0.4% (w/w) in a culture media.

In still other embodiments, the promoter used herein is responsive to the level of rhamnose in the environment, otherwise referred to herein as a "rhamnose-regulatable promoter". Analogous to the araC-$P_{araBAD}$ system described above, the rhaRS-$P_{rhaB}$ activator-promoter system is tightly regulated by rhamnose. Expression from the rhamnose promoter ($P_{rha}$) is induced to high levels in the presence of rhamnose. In some embodiments, the bacteria are cultured in the presence of rhamnose. Rhamnose is commonly found in bacteria but rarely found in human subjects. The rhaBAD operon is controlled by the $P_{rhaBAD}$ promoter. This promoter is regulated by two activators, RhaS and RhaR, and the corresponding nucleic acid sequences belong to one transcription unit that is located in the opposite direction of the rhaBAD nucleic acid sequences. In the presence of L-rhamnose, RhaR binds to the $P_{rhaRS}$ promoter and activates the production of RhaR and RhaS. RhaS together with L-rhamnose, in turn, bind to the $P_{rhaBAD}$ and the $P_{rhaT}$ promoters and activates the transcription of the structural nucleic acid sequences. Full induction of the arabinose, maltose and rhamonse regulated promoters described herein requires binding of the Crp-cAMP complex, which is a key regulator of catabolite repression.

Although both L-arabinose and L-rhamnose act directly as inducers of the expression of regulons that mediate their catabolism, important differences exist in regard to the regulatory mechanisms. L-Arabinose acts as an inducer with the activator AraC in the positive control of the arabinose regulon. However, the L-rhamnose regulon is subject to a regulatory cascade, and is therefore subject to even tighter control than the araC-P$_{araBAD}$ system. L-Rhamnose acts as an inducer with the activator RhaR for synthesis of RhaS, which in turn acts as an activator in the positive control of the rhamnose regulon. In the present disclosure, rhamnose may be used to interact with the RhaR protein and then the RhaS protein may activate transcription of a nucleic acid sequence operably-linked to the P$_{rhaBAD}$ promoter.

In still other embodiments, the promoter may be responsive to the level of xylose in the environment, referred to herein as a "xylose-regulatable promoter". Generally, xylose concentrations of between 0.0002% to 0.63% (w/w) in the environment activate the expression of a xylose inducible promoter described herein (see, e.g., Bhavsar et al. (2001) App. Environ. Microbiol. 67(1): 403-10(34)). The xylR-P$_{xylA}$ system is another well-established inducible activator-promoter system. Xylose induces xylose-specific operons (e.g., xylE, xylFGHR, and xylAB) that are regulated by XylR and the cyclic AMP-Crp system. The XylR protein serves as a positive regulator by binding to two distinct regions of the xyl nucleic acid sequence promoters. As with the araC-P$_{araBAD}$ system described above, the xylR-P$_{xylAB}$ and/or xylR-P$_{xylFGH}$ regulatory systems may be used. In these embodiments, xylose interacting with the XylR protein activates transcription of nucleic acid sequences operably-linked to either of the two P$_{xyl}$ promoters.

As used herein, the term "exogenous" refers to a substance (e.g., a nucleic acid or polypeptide) present in a cell other than its native source. The term exogenous can refer to a nucleic acid or a protein that has been introduced by a process involving the hand of man into a biological system such as a cell or organism in which it is not normally found or in which it is found in undetectable amounts. A substance can be considered exogenous if it is introduced into a cell or an ancestor of the cell that inherits the substance. In contrast, the term "endogenous" refers to a substance that is native to the biological system or cell.

A "pharmaceutical composition," as used herein, refers to a composition comprising an active ingredient (e.g., a recombinant bacterium described herein) with other components such as a physiologically suitable carrier and/or excipient.

As used herein, the term "pharmaceutically acceptable carrier" or a "pharmaceutically acceptable excipient" refers to a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline (e.g., phosphate-buffered saline (PBS)); (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (24) $C_2$-$C_{12}$ alcohols, such as ethanol; and (25) other non-toxic compatible substances employed in pharmaceutical formulations. Wetting agents, coloring agents, release agents, coating agents, disintegrating agents, binders, sweetening agents, flavoring agents, perfuming agents, protease inhibitors, plasticizers, emulsifiers, stabilizing agents, viscosity increasing agents, film forming agents, solubilizing agents, surfactants, preservative and antioxidants can also be present in the formulation. The terms such as "excipient", "carrier", "pharmaceutically acceptable excipient" or the like are used interchangeably herein.

A "plasmid" or "vector" includes a nucleic acid construct designed for delivery to a host cell or transfer between different host cells. The nucleic acid incorporated into the plasmid can be operatively linked to an expression control sequence when the expression control sequence controls and regulates the transcription and translation of that polynucleotide sequence.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. The terms "protein" and "polypeptide" as used herein refer to both large polypeptides and small peptides. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

A "nucleic acid" or "nucleic acid sequence" may be any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA, rRNA, and tRNA.

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (35); Bauer et al. (36); Craik (37); Smith et al. (38); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

The term "statistically significant" or "significantly" refers to statistical significance and generally means a two standard deviation (2SD) or greater difference.

As used herein, the term "host cell" refers to a cell in an organism to which the recombinant bacterium is being administered in order to, for example, induce an immune response. In one embodiment, a host is a bird, equine, or human and a host cell refers, respectively, to a bird cell, an equine cell, or a human cell.

Other than in the operating examples, or where otherwise indicated, all numbers expressing quantities of ingredients or reaction conditions used herein should be understood as modified in all instances by the term "about." The term "about" when used in connection with percentages can mean±1.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

I. Recombinant Bacteria

The present disclosure provides, in some embodiments, a recombinant bacterium capable of regulated expression of at least one nucleic acid sequence encoding an antigen of interest. The recombinant bacterium described herein is particularly effective in eliciting an immune response (e.g., protective immunity) against the antigen of interest because the bacterium comprise multiple recombinant regulatory systems that permit the bacterium to replicate upon administration and to colonize lymphoid tissues in a subject in order to elicit potent immune responses. However, after multiple replication cycles in vivo, the bacterium ultimately exhibits an attenuated phenotype which allows for safe administration to a subject, for example as a vaccine composition. The recombinant regulatory systems of the bacteria described herein depend, in part, on multiple genetic regulatory elements that are responsive to one or more sugars (e.g., arabinose, rhamnose, mannose, maltose, xylose, and galactose) that not available to the recombinant bacteria described herein can be altered upon administration to a subject. In some embodiments, the subject is administered one or more sugars before, after or concurrently with the administration of a recombinant bacterium described herein in order to activate and/or repress a sugar-responsive regulatory system of the bacteria. In some embodiments, the recombinant bacterium described herein comprises at least three regulatory systems, each dependent on a different sugar, which facilitates initial invasion of a host cell in the subject, delayed attenuation, and improved immunogenicity.

In some embodiments, the recombinant bacterium described herein can be regulated for delayed attenuation in vivo. In some embodiments, the recombinant bacterium described herein is capable of regulated delayed expression of a nucleic acid encoding an antigen of interest. In some embodiments, the recombinant bacterium described herein exhibits regulated production of Generalized Modules for Membrane Antigens (GMMA), or outer membrane vesicles, in vivo, which may lead to enhanced production of conserved outer membrane proteins present in the bacterium, and ultimately improved immunogenicity. In some embodiments, the recombinant bacterium described herein is capable of both regulated expression of at least one nucleic acid encoding at least one antigen of interest and regulated attenuation. In some embodiments, the recombinant bacterium described herein is capable of both regulated expression of at least one nucleic acid encoding at least one antigen of interest and regulated production of GMMA, or outer membrane vesicles, in vivo. In some embodiments, the recombinant bacterium described herein is capable of both regulated production of GMMA, or outer membrane vesicles, in vivo, and regulated attenuation. In some embodiments, the recombinant bacterium described herein is capable of regulated expression of at least one nucleic acid encoding at least one antigen of interest, regulated attenuation, and regulated production of GMMA, or outer membrane vesicles, in vivo. In some embodiments, each of these properties is directly or indirectly regulated by the abundance of at least one sugar (e.g., arabinose, rhamnose, mannose, xylose, maltose, and galactose).

In some embodiments, the bacterium described herein is a Gram negative bacterium. In some embodiments, the bacterium is a pathogenic bacterium. In some embodiments, the bacterium is an avirulent bacterium. In some embodiments, the bacterium belongs to the Enterobaceteriaceae. In some embodiments, the bacterium belongs to a genus selected from: *Alterococcus, Aquamonas, Aranicola, Arsenophonus, Brenneria, Rudvicia, Buttiauxella, Candidatus Phlomobacter, Cedeceae, Citrobacter, Edwardsiella, Enterobacter, Erwinia, Escherichia, Ewingella, Hafnia, Klebsiella, Kluyvera, Leclercia, Leminorella, Moellerella, Morganella, Obesumbacterium, Pantoea, Pectobacterium, Photorhabdus, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhbdus*, or *Yersinia, Yokenella*. In some embodiments, the bacterium is a pathogenic species of Enterobaceteriaceae. In some embodiments, the bacterium is selected from the group consisting of *Escherichia coli, Shigella, Edwardsiella, Salmonella, Citrobacter, Klebsiella, Enterobacter, Serratia, Proteus, Morganella, Providencia* and *Yersinia*. In some embodiments, the bacterium is of the genus *Salmonella*. In some embodiments, the bacterium is of the genus *Yersinia*. In some embodiments, the bacterium is of the genus Edwardsiella. In some embodiments, the bacterium is of a genus, species, or strain commonly used as a live or attenuated vaccine.

Some embodiments of the instant disclosure comprise a species or subspecies of the *Salmonella* genera (e.g., *S.*

*enterica* or *S. hongori*). For instance, the recombinant bacterium may be a *Salmonella enterica* serovar, including, for example, Paratyphi A, Enteritidis, Typhi, and Typhimurium. In some embodiments, the recombinant bacterium is of the serovar S. Typhimurium, S. Typhi, S. Paratyphi, S. Gallinarum, S. Enteritidis, S. Choleraesius, S. Arizonae, S. Newport, S. Heidelberg, S. Infantis, S. Cholerasiuis, or S. Dublin.

A recombinant bacterium derived from *Salmonella* may be particularly suited to use as a vaccine. For example, oral infection of a host with a *Salmonella* strain typically leads to colonization of the gut-associated lymphoid tissue (GALT) or Peyer's patches, which leads to the induction of a generalized mucosal immune response to the recombinant bacterium. Further penetration of the bacterium into the mesenteric lymph nodes, liver and spleen may augment the induction of systemic and cellular immune responses directed against the bacterium. Thus, the use of recombinant *Salmonella* for oral immunization stimulates all three branches of the immune system, which is particularly important for immunizing against infectious disease agents that colonize on and/or invade through mucosal surfaces. In some embodiments, the recombinant bacterium described herein is used to induce an immune response in poultry (e.g., as a vaccine). When used in poultry, the recombinant bacterium may be administered by course spray and thereby inoculate the conjunctiva-associated lymphoid tissue (CALT) via eye exposure, the nasal-associated lymphoid tissue (NALT) and bronchus-associated lymphoid tissue (BALT) via respiratory exposure and the GALT via oral exposure. In some embodiments, the recombinant bacterium described herein is administered to newly-hatched chicks.

A. Attenuation

In some embodiments, the recombinant bacterium described herein is modified such that the expression of one or more genes, e.g., virulence genes, can be regulated in a sugar-responsive manner. In some embodiments, one or more endogenous genes, e.g., virulence genes, are deleted from the bacterial chromosome. In some embodiments, the deletion is a partial deletion of the endogenous gene. In some embodiments, the deletion is a full-length deletion of the endogenous gene. In some embodiments, the gene, e.g., virulence gene, is genetically-altered to prevent transcription and/or translation of the gene encoding the protein. In some embodiments, the endogenous gene is genetically altered to insert a transcriptional terminator in the open reading frame of the gene. In some embodiments, a regulatory region of the gene, e.g., virulence gene, is genetically-modified to alter (e.g., decrease) the expression of the gene. In some embodiments, the promoter of a gene, e.g., virulence gene, is altered to include one or more regulatory elements (e.g., a sugar-responsive promoter).

In some embodiments, the recombinant bacterium described herein is modified to comprise a nucleic acid comprising a gene. In some embodiments, the recombinant bacterium is modified to comprise a nucleic acid comprising a gene, whereby an endogenous copy of the gene in the bacterial chromosome has been altered and/or deleted. In some embodiments, the nucleic acid comprises a gene that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to an endogenous gene in the bacterial chromosome that has been deleted and/or altered. In some embodiments, the nucleic acid comprises a gene that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to an endogenous gene in the bacterial chromosome that has been deleted and/or altered. In some embodiments, the nucleic acid comprises a gene from a bacterial species, subspecies, serovar, or strain that is different than the bacterial species of the recombinant bacterium.

In some embodiments, the nucleic acid comprises a gene from a bacterial species, subspecies, serovar, or strain that is the same as the bacterial species of the recombinant bacterium. In some embodiments, the nucleic acid comprises a gene that is operably-linked to a regulatable promoter (e.g., a sugar-regulatable promoter). In some embodiments, the nucleic acid comprises a gene that is operably-linked to a rhamnose-regulatable promoter, a xylose-regulatable promoter, a galactose-regulatable promoter, an arabinose-regulatable promoter, a mannose-regulatable promoter, or a maltose-regulatable promoter. In some embodiments, the nucleic acid comprising the gene is located in a plasmid in the bacterium. In some embodiments, the nucleic acid comprising the gene is located in the bacterial chromosome. In some embodiments, the nucleic acid comprising the gene is located at the chromosomal locus corresponding to the locus of an endogenous gene that has been deleted or altered in the bacterial chromosome. In some embodiments, the nucleic acid is codon-optimized (e.g., to improve expression of the nucleic acid in the recombinant bacterium).

1. O-antigen Synthesis Genes

In some embodiments, the recombinant bacterium comprises a deletion in an endogenous O-antigen synthesis gene. In some embodiments, the recombinant bacterium comprises a deletion in an endogenous O-antigen ligase gene. In some embodiments, the deletion is a partial deletion of the endogenous O-antigen ligase gene. In some embodiments, the deletion is a full-length deletion of the endogenous O-antigen ligase gene. In some embodiments, the endogenous O-antigen ligase gene is genetically altered to insert a transcriptional terminator in the open reading frame of the gene. In some embodiments, a regulatory region of the endogenous O-antigen ligase gene is genetically-modified to alter (e.g., decrease) the expression of the gene. In some embodiments, the promoter of a endogenous O-antigen ligase gene is altered to include one or more regulatory elements (e.g., a sugar-responsive promoter). In some embodiments, the promoter of a endogenous O-antigen ligase gene is altered to increase the spacing between the Shine-Delgarno sequence and the start codon of the gene. In some embodiments, the promoter of a endogenous O-antigen ligase gene is altered to decrease the spacing between the Shine-Delgarno sequence and the start codon of the gene. In some embodiments, the Shine-Delgarno (SD) sequence, the start codon, the second codon and/or third codons of the O-antigen ligase gene is altered to increase the frequency of adenine nucleobases in order to enhance the translation efficiency of the gene. In some embodiments, the Shine-Delgarno (SD) sequence, the start codon, the second codon and/or third codons of the O-antigen ligase gene is altered to reduce the frequency of adenine nucleobases in order to decrease the translation efficiency of the gene. In some embodiments, the O-antigen ligase gene is waaL (also known as rfaL). The O-antigen ligase WaaL is necessary to ligate polysaccharide to the lipid A-LPS core moiety. Deletion of waaL results in an intact lipid A-LPS core with no O-antigen or individual sugars attached to it. In some embodiments, the O-antigen ligase gene is selected from the group consisting of waaG (also known as rfaG), waaI (also known as rfaI), rfaH, waaJ (also known as rfaJ), wbaP (also known as rfbP), wzy (also known as rfc), waaP, waaQ, waaF, waaP, waaC, and waaA.

In some embodiments, the recombinant bacterium described herein is modified to comprise a nucleic acid comprising an O-antigen ligase gene. In some embodiments, the nucleic acid comprising an O-antigen ligase gene is located on a plasmid in the bacterium. In some embodiments, the nucleic acid comprising an O-antigen ligase gene is located on a chromosome of the bacterium. In some embodiments, the nucleic acid comprising an O-antigen ligase gene is located at the chromosomal locus corresponding to the locus of an endogenous O-antigen ligase gene that has been deleted or altered in the bacterial chromosome. In some embodiments, the recombinant bacterium is modified to comprise a nucleic acid comprising an O-antigen ligase gene, whereby an endogenous copy of the gene in the bacterial chromosome has been altered and/or deleted. In some embodiments, the nucleic acid comprises a Salmonella O-antigen ligase gene.

The nucleic acid sequence of an exemplary Salmonella waaL gene is provided below:

```
                                              (SEQ ID NO: 1)
atgctaaccacatcattaacgttaaataaagagaaatggaagccgatctg gaataaagcgctggttttcttttgttgccacgtattttctggatggta ttacgcgttataaacatttgataatcatacttatggttatcaccgcgatt tatcaggtctcacgctcaccgaaaagtttccccctcttttcaaaatag cgtattttatagcgtagcagtattatcattaatccttgtttattccatac tcatatcgccagatatgaaagaaagtttcaaggaatttgaaaatacggta ctggagggcttcttatatatactttattaattcccgtactattaaaaga tgaaacaaaagaaacggttgcgaaaatagtacttttctccttttttaacaa gtttaggacttcgctgccttgcagagagtattctgtatatcgaggactat aataaagggattatgccattcataagctatgcgcatcgacatatgtccga ttccatggttttcttatttccagcattattgaatatttggctgtttagaa aaaatgcaattaagttggtttttttggtgcttagcgccatctacctttc tttatcctgggaaccctatcgcgaggggcatggttggcggtgcttatagt aggtgttctgtgggcaatactgaaccgccaatggaagttaataggagttg gtgccattttattagccattatcggcgctttggttatcactcaacataat aacaaaccagacccagaacatttactgtataaattacagcagacagatag ctcatatcgttatactaacggaacccagggcaccgcgtggatactgattc aggaaaacccgatcaagggctacggctatggtaatgatgtgtatgatggt gtttataataaacgcgttgtcgattatccaacgtggacctttaaagaatc tatcggtccgcataataccattctgtacatctggtttagtgcaggcatat tgggtctggcgagcctggtctatttatatggcgctatcatcagggaaaca gccagctctaccctcaggaaagtagagataagcccctacaatgctcatct cttgctattttttatcttttcgtcggttttttatatcgttcgtggcaattttg aacaggtcgatattgctcaaattggtatcattaccggttttctgctggcg ctaagaaatagataa.
```

The amino acid sequence of the WaaL protein encoded by the nucleic acid of SEQ ID NO: 1 is provided below:

```
                                              (SEQ ID NO: 2)
MLTTSLTLNKEKWKPIWNKALVFLFVATYFLDGITRYKHLIIILMVITA

IYQVSRSPKSFPPLFKNSVFYSVAVLSLILVYSILISPDMKESFKEFEN

TVLEGFLLYTLLIPVLLKDETKETVAKIVLFSFLTSLGLRCLAESILYI

EDYNKGIMPFISYAHRHMSDSMVFLFPALLNIWLFRKNAIKLVFLVLSA

IYLFFILGTLSRGAWLAVLIVGVLWAILNRQWKLIGVGAILLAIIGALV

ITQHNNKPDPEHLLYKLQQTDSSYRYTNGTQGTAWILIQENPIKGYGYG

NDVYDGVYNKRVVDYPTWTFKESIGPHNTILYIWFSAGILGLASLVYLY

GAIIRETASSTLRKVEISPYNAHLLLFLSFVGFYIVRGNFEQVDIAQIG

IITGFLLALRNR.
```

In some embodiments, the nucleic acid comprises a Salmonella waaL gene (provided as SEQ ID NO: 1). In some embodiments, the nucleic acid comprises a waaL gene, wherein the waaL gene comprises a nucleic acid sequence that is at least 75%, at least 80%, at least 810%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 1. In some embodiments, the nucleic acid comprises a waaL gene, wherein the waaL gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 1.

In some embodiments, the nucleic acid comprises a nucleic acid sequence encoding an O-antigen ligase, wherein said O-antigen ligase comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 2. In some embodiments, the nucleic acid comprises a nucleic acid sequence encoding an O-antigen ligase, wherein said O-antigen ligase comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 2.

In some embodiments, the nucleic acid comprises an O-antigen ligase gene from a bacterial species, subspecies, serovar, or strain that is different than the bacterial species of the recombinant bacterium. In some embodiments, the nucleic acid comprises an O-antigen ligase gene from a bacterial species, subspecies, serovar, or strain that is the same as the bacterial species of the recombinant bacterium.

In some embodiments, the nucleic acid comprises an O-antigen ligase gene that is operably-linked to a regulatable promoter (e.g., a sugar-regulatable promoter). In some embodiments, the nucleic acid comprises an O-antigen ligase gene (e.g., waaL) that is operably-linked to a sugar-regulatable promoter. Advantageously, recombinant bacterial strains comprising a nucleic acid comprising an O-antigen ligase gene (e.g., waaL) that is operably linked to a sugar regulatable promoter will synthesize normal LPS in the presence of the sugar (e.g., rhamnose) in vitro, but will form rough LPS in vivo due to the absence of the sugar that activates the promoter and therefore, the expression of the O-antigen ligase. Without wishing to be bound by any particular theory, using this strategy, the bacterium will expose conserved LPS core oligosaccharide and have enhanced production of conserved outer membrane proteins (OMPs; e.g., porins) which may lead to improved immunogenicity and aid in the production of a cross-protective immune response against an antigen of interest synthesized in the bacterium in vivo. In some embodiments, the sugar regulatable promoter exhibits increased activity (e.g., increased transcription) in the presence of a specific sugar and decreased activity in the absence of a sugar. In some embodiments, the nucleic acid comprises an O-antigen ligase gene that is operably-linked to a rhamnose-regulatable promoter (e.g., a sugar-regulatable promoter). In some embodiments, the nucleic acid comprises an O-antigen ligase gene that is operably-linked to an arabinose-regulatable promoter (e.g., a sugar-regulatable promoter). In some embodiments, the use of a rhamnose-regulatable promoter (e.g., rhaSR $P_{rhaBAD}$) may be preferable to an arabinose-regulatable promoter because a relatively higher concentration is required to activate an arabinose-regulatable promoter as compared to a rhamnose-regulatable promoter (see, e.g., Giacalone et al. (2006) BioTechniques 40(3): 355-366 (39), the entire contents of which are incorporated herein by reference). In some embodiments, the recombinant bacterium comprises the mutation ΔwaaL/ΔpagL::TT rhaSR $P_{rhaBAD}$ waaL.

2. Lipid a Deacylase Genes

In some embodiments, the recombinant bacterium comprises a deletion in an endogenous lipid A deacylase gene. In some embodiments, the deletion is a partial deletion of the endogenous lipid A deacylase gene. In some embodiments, the deletion is a full-length deletion of the endogenous lipid A deacylase gene. In some embodiments, the endogenous lipid A deacylase gene is genetically altered to insert a transcriptional terminator in the open reading frame of the gene. In some embodiments, a regulatory region of the endogenous lipid A deacylase gene is genetically-modified to alter (e.g., decrease) the expression of the gene. In some embodiments, the promoter of an endogenous lipid A deacylase gene is altered to include one or more regulatory elements (e.g., a sugar-responsive promoter). In some embodiments, the lipid A deacylase gene is pagL. Bacterial comprising a deletion of the lipid A deacylase gene pagL have been found to produced increased amounts of outer membrane vesicles (see, e.g., Elhenawy et al. (2016) mBio 7(4): e00940-16 (40)). Deletion of the pagL gene of Salmonella does not impair bacterial virulence (see, e.g., Man et al. Proc. Nat'l. Acad. Sci. USA 111: 7403-8 (41)). Without wishing to be bound by any particular theory, in some embodiments, the recombinant bacterium described herein comprise one or more genetic modifications which results in increased vesiculation (i.e., increased vesicle production) which may be particularly advantageous in inducing an immune response in the host against an antigen of interest that is expressed by the bacterium.

3. Phosphomannose Isomerase Genes

In some embodiments, the recombinant bacterium comprises a deletion in an endogenous phosphomannose isomerase gene. Phosphomannose isomerase, also known as mannose-6 phosphate isomerase, catalyzes the reversible interconversion of fructose 6-phosphate to mannose 6-phosphate. Mannose 6-phosphate is then converted to GDP-mannose and used for the synthesis of O-antigen side chains. Bacteria with deletions of the phosphomannose isomerase gene pmi are not mannose sensitive and are partially attenuated (see, e.g., Collins et al. (1991) Infect. Immun. 59(3): 1079-85 (42)). These pmi mutants synthesize wild-type levels of LPS O-antigen side chains when grown in media containing mannose, and are both attenuated but highly immunogenic (see, e.g., Curtiss et al. (2007) "Induction of host immune responses using Salmonella-vectored vaccines." In: Brogden K A, Minion F C, Cornick N, Stanton T B, Zhang Q, Nolan L K, Wannemuehler M J, ed. Virulence Mechanisms of Bacterial Pathogens. 4th ed. Washington D.C.: ASM Press (43)). In some embodiments, the deletion of the endogenous phosphoisomerase gene is a partial deletion. In some embodiments, the deletion of the endogenous phosphomannose isomerase gene is a full-length deletion. In some embodiments, the endogenous phosphomannose isomerase gene is genetically altered to insert a transcriptional terminator in the open reading frame of the gene. In some embodiments, a regulatory region of the endogenous phosphomannose isomerase gene is genetically-modified to alter (e.g., decrease) the expression of the phosphomannose isomerase gene. In some embodiments, the promoter of an endogenous phosphomannose isomerase gene is altered to include one or more regulatory elements (e.g., a sugar-responsive promoter). In some embodiments, the phosphomannose isomerase gene is pmi.

In some embodiments, the bacterium comprises a deletion of a pmi gene. In some embodiments, the bacterium comprises a Δpmi-2426 mutation. A bacterium comprising a Δpmi-2426 mutation, grown in the presence of mannose, is capable of synthesizing a complete LPS O-antigen. Non-phosphorylated mannose, which is the form required for bacterial uptake, is unavailable in vivo. Hence, a bacterium comprising a Δpmi-2426 mutation loses the ability to synthesize LPS O-antigen serotype specific side chains in vivo and the number of O-antigen side chains attached to the LPS core decreases by about half after each cell division in vivo. The LPS that is synthesized comprises a core structure that is substantially similar across all Salmonella enterica serotypes except S. Arizona. This results in a bacterium that is capable of eliciting an immune response against at least two Salmonella serotypes without substantially inducing an immune response specific to the serotype of the bacterial vector. In some embodiments, the bacterium is capable of eliciting an immune response against all Salmonella serotypes without substantially inducing an immune response specific to the serotype of the bacterial vector.

A recombinant bacterium described herein that comprises a deletion in a pmi mutation may also comprise other mutations that ensure that mannose available to the bacterium during in vitro growth is used for LPS O-antigen synthesis. For instance, a bacterium may comprise a Δ(gmd-fcl)-26 mutation. This mutation deletes two nucleic acid sequences that encode enzymes for conversion of GDP-mannose to GDP-fucose, ensuring that mannose available to the bacterium during in vitro growth is used for LPS O-antigen synthesis and not colanic acid production. Similarly, a bacterium may comprise the Δ(wcaM-wza)-8 mutation, which deletes all 20 nucleic acid sequences necessary for colanic acid production, and also precludes conversion of GDP-mannose to GDP-fucose.

4. UDP-Galactose Epimerase Genes

UDP-Gal is the precursor for the assembly of the LPS O-antigen side chains, the LPS outer core, for colanic acid and other polysaccharide polymers having galactose as a constituent (44). UDP-Gal is synthesized by conversion of glucose-1-P to UDP-Glu by the enzyme glucose-1-P uridylyltransferase encoded by the galU gene with UDP-Glu converted to UDP-Gal by the enzyme UDP-galactose epimerase encoded by the galE gene (45, 46). Strains grown in the presence of galactose can synthesize UDP-Gal by a different pathway in which galactose after uptake is converted to galactose-1-P by galactose kinase encoded by the galK gene which in turn is converted to UDP-Gal by the enzyme UDP-Gal transferase encoded by the galT gene (45). Strains with a galE mutation are unable to synthesize LPS outer core and LPS O-antigen unless galactose is supplied in the growth medium (47). Because of these facts and properties *Salmonella* strains with galE mutations can synthesize LPS when grown with galactose and are invasive to colonize lyphoid tissues, but loose this ability in vivo due to the unavailability of free galactose such that they gradually loose LPS components as they multiply in the infected or immunized animal host. Just like pni mutants, they gradually become attenuated due to increasing susceptibility to complement-mediated cytotoxicity and enhanced phagocytosis and killing my macrophages. However, the supply of galactose to such galE mutants can lead to cell death by lysis since the accumulation of Gal-1-P and UDP-Gal is toxic (30, 48, 49). Because of this, growth of galE mutants in the presence of galactose selects for mutations in genes for galactose uptake or in the galK and galT genes so that toxic products are not synthesized. Unfortunately, such galactose-resistant mutants are no longer able to make LPS and are totally attenuated, non-invasive and non-immunogenic (30, 50). To circumvent these problems to enable use of galE mutations in *Salmonella* vaccine strains, we have devised a means to generate galE mutants with the potential for reversible synthesis of LPS dependent on the presence or absence of galactose that are resistant to galactose with no selection of mutants unable to synthesize UDP-Gal for LPS synthesis.

5. Iron Acquisition Regulatory Genes

In some embodiments, the recombinant bacterium comprises a deletion in the endogenous promoter $P_{fur}$, which regulates the expression of the fur gene. Fur represses the transcription of genes involved in iron acquisition in the presence of free iron. When iron concentrations become low in the bacterium, Fur ceases to be synthesized which leads to the constitutive expression of genes encoding iron acquisition proteins (e.g., iron-regulated outer membrane proteins (IROMPs). In some embodiments, the deletion is a partial deletion of the endogenous $P_{fur}$ promoter. In some embodiments, the deletion is a full-length deletion of the endogenous $P_{fur}$ promoter. In some embodiments, the endogenous $P_{fur}$ promoter is genetically-modified to alter (e.g., decrease) the expression of the fur gene. In some embodiments, the endogenous $P_{fur}$ promoter is genetically altered to comprise a transcriptional terminator.

In some embodiments, the recombinant bacterium comprises a nucleic acid comprising a fur gene (e.g., a fur gene from the same bacterial species as the recombinant bacterium).

In some embodiments, the nucleic acid comprising a fur gene is located on a plasmid in the bacterium. In some embodiments, the nucleic acid comprising a fur gene is located on a chromosome of the bacterium. In some embodiments, the nucleic acid comprising a fur gene is located at the chromosomal locus corresponding to the locus of an endogenous fur gene that has been deleted or altered in the bacterial chromosome. In some embodiments, the recombinant bacterium is modified to comprise a nucleic acid comprising a fur gene, whereby an endogenous copy of the fur gene in the bacterial chromosome has been altered and/or deleted.

The nucleic acid sequence of an exemplary *Salmonella* fur gene is provided below:

(SEQ ID NO: 3)
atgactgacaacaataccgcattaaagaaggctggcctgaaagtaacgc ttcctcgtttaaaaattctggaagttcttcaggaaccagataaccatca cgtcagtgcggaagatttatacaaacgcctgatcgacatgggtgaagaa atcggtctggcaaccgtataccgtgtgctgaaccagtttgacgatgccg gtatcgtgacccgccataattttgaaggcggtaaatccgttttttgaact gacgcaacagcatcatcacgaccatcttatctgccttgattgcggaaaa gtgattgaatttagtgatgactctattgaagcgcgccagcgtgaaattg cggcgaaacacggtattcgtttaactaatcacagcctctatctttacgg ccactgcgctgaaggcgactgccgcgaagacgagcacgcgcacgatgac gcgactaaataa.

The amino acid sequence of the Fur protein encoded by the nucleic acid of SEQ ID NO: 3 is provided below:

(SEQ ID NO: 4)
MTDNNTALKKAGLKVTLPRLKILEVLQEPDNHEIVSAEDLYKRLIDMGE

EIGLATVYRVLNQFDDAGIVTRHNFEGGKSVFELTQQHHHDHLICLDCG

KVIEFSDDSIEARQREIAAKHGIRLTNHSLYLYGHCAEGDCREDEHAHD

DATK.

In some embodiments, the nucleic acid comprises a *Salmonella* fur gene (provided as SEQ ID NO: 3). In some embodiments, the nucleic acid comprises a fur gene, wherein the fur gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 3. In some embodiments, the nucleic acid comprises a fur gene, wherein the fur gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 3.

In some embodiments, the nucleic acid comprises a nucleic acid sequence encoding a Fur protein, wherein said Fur protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 4. In some embodiments, the nucleic acid comprises a nucleic acid sequence encoding a Fur protein, wherein said Fur protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 4.

In some embodiments, the nucleic acid comprises a fur gene from a bacterial species, subspecies, serovar, or strain that is the same as the bacterial species of the recombinant bacterium.

In some embodiments, the nucleic acid comprises a fur gene that is operably-linked to a regulatable promoter (e.g., a sugar-regulatable promoter). In some embodiments, the nucleic acid comprises a fur gene that is operably-linked to a sugar-regulatable promoter. In some embodiments, the sugar regulatable promoter exhibits increased activity (e.g., increased transcription) in the presence of a specific sugar and decreased activity in the absence of a sugar. In some embodiments, the nucleic acid comprises a fur gene that is operably-linked to a rhamnose-regulatable promoter (e.g., a sugar-regulatable promoter). In some embodiments, the nucleic acid comprises a fur gene that is operably-linked to an arabinose-regulatable promoter (e.g., a sugar-regulatable promoter). In some embodiments, the arabinose-regulatable promoter is araC $P_{araBAD}$. In some embodiments, the recombinant bacterium comprises the mutation $\Delta P_{fur}$::TT araC $P_{araBAD}$ fur.

6. Colicin Uptake Genes

*Salmonella* spontaneously release 50 to 90 nm bleb-like particles of outer cell wall membrane called Generalized Modules for Membrane Antigens (GMMA) or outer membrane vesicles, which constitute an enriched source of outer membrane-associated antigens that retain their native confirmation and proper orientation. *Salmonella* can be genetically-modified to produce more GMMAs, or outer membrane vesicles (e.g., by deletion of a tolR gene) which can be readily purified (e.g., by centrifugation and filtration in the absence of detergent). GMMAs, or outer membrane vesicles, contain multiple pathogen-associated molecular patterns (PAMPS), including toll-like receptor (TLR) ligands, which may act as self-adjuvants when eliciting immune responses. Recombinant bacteria that do not express tolR produce more GMMA, or outer membrane vesicles, which may be particularly advantageous in increasing the presentation of conserved proteins to aid in inducing, for example, antibodies cross-reactive to OMPs of other *Salmonella* serovars. In addition, without wishing to be bound by any particular theory, increased production and release of GMMA, or outer membrane vesicles, will also lead to the improved presentation of an antigen of interest that is expressed by the recombinant bacterium as described herein. In some embodiments, the antigen of interest is a secreted antigen.

In some embodiments, the recombinant bacterium comprises a deletion in an endogenous gene encoding a colicin uptake protein. Two types of colicins have been described. Group A colicins are Tol-dependent colicins and Group B colicins are TonB-dependent colicins (see, e.g., Cascales et al. (2007) Microbiol. Mol. Biol. Rev. 71(1): 158-229 (51), the entire contents of which are hereby incorporated by reference). In some embodiments, the recombinant bacterium comprises a deletion in the endogenous promoter $P_{tolR}$, which regulates the expression of the tolR gene. This deletion will cause the endogenous tolR gene to not be expressed by the recombinant bacterium comprising the deletion. In some embodiments, the endogenous $P_{tolR}$ promoter is genetically-modified to alter (e.g., decrease) the expression of the tolR gene. In some embodiments, the endogenous $P_{tolR}$ promoter is genetically altered to comprise a transcriptional terminator.

In some embodiments, the recombinant bacterium described herein is modified to comprise a nucleic acid comprising a tolR gene. In some embodiments, the nucleic acid comprising a tolR gene is located on a plasmid in the bacterium. In some embodiments, the nucleic acid comprising a tolR gene is located on a chromosome of the bacterium. In some embodiments, the nucleic acid comprising a tolR gene is located at the chromosomal locus corresponding to the locus of an endogenous a tolR that has been deleted or altered in the bacterial chromosome. In some embodiments, the recombinant bacterium is modified to comprise a nucleic acid comprising a tolR gene, whereby an endogenous copy of the tolR gene in the bacterial chromosome has been altered and/or deleted.

The nucleic acid sequence of an exemplary *Salmonella* tolR gene is provided below:

```
                                            (SEQ ID NO: 5)
atgactgacaacaataccgcattaaagaaggctggcctgaaagtaacgct tcctcgtttaaaaattctggaagttcttcaggaaccagataaccatcacg tcagtgcggaagatttatacaaacgcctgatcgacatgggtgaagaaatc ggtctggcaaccgtataccgtgtgctgaaccagtttgacgatgccggtat cgtgacccgccataatttgaaggcggtaaatccgtttttgaactgacgc aacagcatcatcacgaccatcttatctgccttgattgcggaaaagtgatt gaatttagtgatgactctattgaagcgcgccagcgtgaaattgcggcgaa acacggtattcgtttaactaatcacagcctctatctttacggccactgcg ctgaaggcgactgccgcgaagacgagcacgcgcacgatgacgcgactaaa taa.
```

The amino acid sequence of the TolR protein encoded by the nucleic acid of SEQ ID NO: 5 is provided below:
MTDNNTALKKAGLKVTLPRLKILEVLQEPDNHHV-SAEDLYKRLIDMGEEIGLATVY RVLNQFDDA-GIVTRHNFEGGKSVFELTQQHHHDHLI-CLDCGKVIEFSDDSIEARQREI AAKHGIRLTNHSLYLYGHCAEGDCREDEHAHDDATK (SEQ ID NO: 6).

In some embodiments, the nucleic acid comprises a *Salmonella* tolR gene (provided as SEQ ID NO: 5). In some embodiments, the nucleic acid comprises a tolR gene, wherein the tolR gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 5. In some embodiments, the nucleic acid comprises a tolR gene, wherein the tolR gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 5.

In some embodiments, the nucleic acid comprises a nucleic acid sequence encoding a TolR protein, wherein said TolR protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 6. In some embodiments, the nucleic acid comprises a nucleic acid sequence encoding a TolR protein, wherein said TolR protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 6.

In some embodiments, the nucleic acid comprises a tolR gene from a bacterial species, subspecies, serovar, or strain that is different than the bacterial species of the recombinant bacterium. In some embodiments, the nucleic acid comprises a tolR gene from a bacterial species, subspecies, serovar, or strain that is the same as the bacterial species of the recombinant bacterium.

In some embodiments, the nucleic acid comprises a tolR gene that is operably-linked to a regulatable promoter (e.g., a sugar-regulatable promoter). In some embodiments, the nucleic acid comprises a tolR gene that is operably-linked to a sugar-regulatable promoter. In some embodiments, the sugar regulatable promoter exhibits increased activity (e.g., increased transcription) in the presence of a specific sugar and decreased activity in the absence of a sugar. In some embodiments, the nucleic acid comprises a tolR gene that is operably-linked to a rhamnose-regulatable promoter (e.g., a sugar-regulatable promoter). In some embodiments, the nucleic acid comprises a tolR gene that is operably-linked to an arabinose-regulatable promoter. In some embodiments, the arabinose-regulatable promoter is $P_{BAD}$. In some embodiments, the recombinant bacterium comprises the mutation $\Delta P_{tolR}$::TT araC $P_{araBAD}$ tolR.

7. Endosomal Escape Genes

In some embodiments, the recombinant bacterium has been genetically-altered such that the bacterium is capable of escaping the endosomal compartment of a host cell. A recombinant bacterium may exhibit a temporal delay in escaping an endosome following invasion of the host cell. Methods of detecting escape from an endosomal compartment of a host cell are well known in the art, and include, for example, microscopic analysis.

In some embodiments, the recombinant bacterium comprises a deletion in an endogenous sifA gene. In some embodiments, the recombinant bacterium comprises a mutation that alters the function of SifA. SifA is an effector protein necessary for the formation of *Salmonella*-induced filaments and for the maintenance of the vacuolar membrane enclosing the bacterium. Bacteria comprising a deletion of sifA are capable of escaping the host cell endosome (also called the *Salmonella*-containing vesicle, or SCV) following cellular invasion. In some embodiments, the deletion of the endogenous sifA gene is a partial deletion. In some embodiments, the deletion of the endogenous sifA gene is a full-length deletion. In some embodiments, the endogenous sifA gene is genetically altered to insert a transcriptional terminator in the open reading frame of the gene. In some embodiments, a regulatory region of the endogenous sifA gene is genetically-modified to alter (e.g., decrease) the expression of the sifA gene. In some embodiments, the promoter of an endogenous sifA gene is altered to include one or more regulatory elements (e.g., a sugar-responsive promoter).

In some embodiments, the recombinant bacterium described herein is modified to comprise a nucleic acid comprising a sifA gene. In some embodiments, the nucleic acid comprising a sifA gene is located on a plasmid in the bacterium. In some embodiments, the nucleic acid comprising a sifA gene is located on a chromosome of the bacterium. In some embodiments, the nucleic acid comprising a sifA gene is located at the chromosomal locus corresponding to the locus of an endogenous a sifA that has been deleted or altered in the bacterial chromosome. In some embodiments, the recombinant bacterium is modified to comprise a nucleic acid comprising a sifA gene, whereby an endogenous copy of the sifA gene in the bacterial chromosome has been altered and/or deleted.

The nucleic acid sequence of an exemplary *Salmonella* sifA gene is provided below:

```
                                         (SEQ ID NO: 7)
atgccgattactatagggaatggttttttaaaaagtgaaatccttaccaa ctccccaaggaatacgaaagaagcatggtggaaagttttatgggaaaaaa ttaaagacttcttttttctactggcaaagcaaaagcggaccgttgtcta catgagatgttgtttgccgaacgcgcccccacacgagagcggcttacaga gatttttttgagttgaaagagttagcctgcgcatcgcaaagagatagat ttcaggttcataatcctcatgaaaatgatgccaccattattcttcgcatc atggatcaaaacgaagagaacgaattgttacgtatcactcaaaataccga tacctttagctgtgaagtcatggggaatctttattttttaatgaaagatc gcccggatattttaaaatcgcatccacaaatgacggccatgattaagaga agatatagcgaaatcgtagactacccccctcccttcgacattatgtctcaa tcctgctggcgcgccgatattatcggttccattagacaacatagaggggt atttatatactgaattgagaaaaggacatttagatgggtggaaagcgcaa gaaaaggcaacctacctggcagcgaaaattcagtctgggattgaaaagac aacgcgcattttacaccatgcgaatatatccgaaagtactcagcaaaacg catttttagaaacaatggcgatgtgtggattaaaacagcttgaaatacca ccaccgcatacccacatacctattgaaaaaatggtaaaagaggttttact agcggataagacgtttcaggcgttcctcgtaacggatcccagcaccagcc aaagtatgttagctgagatagtcgaagccatctctgatcaggttttcac gccattttagaatagaccccccaggctatacaaaaaatggcggaagaaca gttaaccacgctacacgttcgctcagaacaacaaagcggctgtttatgtt gttttttataa.
```

The amino acid sequence of the SifA protein encoded by the nucleic acid of SEQ ID NO: 7 is provided below:

```
                                         (SEQ ID NO: 8)
MPITIGNGFLKSEILTNSPRNTKEAWWKVLWEKIKDFFFSTGKAKADRCL

HEMLFAERAPTRERLTEIFFELKELACASQRDRFQVHNPHENDATIILRI

MDQNEENELLRITQNTDTFSCEVIVIGNLYFLMKDRPDILKSHPQMTAMI
```

-continued

```
KRRYSEIVDYPLPSTLCLNPAGAPILSVPLDNIEGYLYTELRKGHLDGWK

AQEKATYLAAKIQSGIEKTTRILHHANISESTQQNAFLETMAMCGLKQLE

IPPPHTHIPIEKMVKEVLLADKTFQAFLVTDPSTSQSMLAEIVEAISDQV

FHAIFRIDPQAIQKMAEEQLTTLHVRSEQQSGCLCCFL.
```

In some embodiments, the nucleic acid comprises a Salmonella sifA gene (provided as SEQ ID NO: 7). In some embodiments, the nucleic acid comprises a sifA gene, wherein the sifA gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 7. In some embodiments, the nucleic acid comprises a sifA gene, wherein the sifA gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 7.

In some embodiments, the nucleic acid comprises a nucleic acid sequence encoding a SifA protein, wherein said SifA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%. at least 94%, at least 95%, at least 96%, at least 97%, at least 98%, at least 99%, or 100% identical to the amino acid sequence of SEQ ID NO: 8. In some embodiments, the nucleic acid comprises a nucleic acid sequence encoding a SifA protein, wherein said SifA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 8.

In some embodiments, the nucleic acid comprises a sifA gene from a bacterial species, subspecies, serovar, or strain that is different than the bacterial species of the recombinant bacterium. In some embodiments, the nucleic acid comprises a sifA gene from a bacterial species, subspecies, serovar, or strain that is the same as the bacterial species of the recombinant bacterium.

In some embodiments, the nucleic acid comprises a sifA gene that is operably-linked to a regulatable promoter (e.g., a sugar-regulatable promoter). In some embodiments, the nucleic acid comprises a sifA gene that is operably-linked to a sugar-regulatable promoter. In some embodiments, the sugar regulatable promoter exhibits increased activity (e.g., increased transcription) in the presence of a specific sugar and decreased activity in the absence of a sugar. In some embodiments, the nucleic acid comprises a sifA gene that is operably-linked to a rhamnose-regulatable promoter (e.g., a sugar-regulatable promoter). In some embodiments, the nucleic acid comprises a sifA gene that is operably-linked to an arabinose-regulatable promoter. In some embodiments, the arabinose-regulatable promoter is $P_{BAD}$. In some embodiments, the recombinant bacterium comprises the mutation ΔsifA::TT araC $P_{BAD}$ sifA. In some embodiments, the recombinant bacterium comprises the mutation $\Delta P_{sifA}$::TT araC $P_{araBAD}$ sifA. When the expression of the nucleic acid comprising a sifA gene is under the control of an arabinose-regulated promoter, the bacterial escape from the host endosome can be delayed. Since arabinose is absent in host cells, arabinose cannot induce the expression of the sifA gene. Thus, if the recombinant bacterium is cultured in the presence of arabinose prior to administration to the subject, the expression of sifA will gradually decrease with each round of bacterial cell division thereby allowing escape of the bacterium from the host cell endosome during the initial cell division cycles. Similar delayed-escape mutations may be constructed using other regulatable promoters, such as from the xylose-regulatable or rhamnose-regulatable promoter systems.

8. GTP Pyrophosphokinase Genes

In some embodiments, the recombinant bacterium comprises a deletion in an endogenous relA gene, which encodes the GTP pyrophosphokinase RelA. The inclusion of a relA deletion in the recombinant bacterium uncouples the occurrence of growth-dependent lysis to the need for continued protein synthesis. In some embodiments, the deletion of the endogenous relA gene is a partial deletion. In some embodiments, the deletion of the endogenous relA gene is a full-length deletion.

9. Other Attenuation Methods

Other methods of attenuation are known in the art. For instance, attenuation may be accomplished by altering (e.g., deleting) native nucleic acid sequences found in the wild-type bacterium. For instance, if the bacterium is *Salmonella*, non-limiting examples of nucleic acid sequences which may be used for attenuation include: a pab nucleic acid sequence, a pur nucleic acid sequence, an aro nucleic acid sequence, asd, a dap nucleic acid sequence, nadA, pncB, galE, pmi, fur, rpsL, ompR, htrA, hemA, cdt, cya, crp, dam, phoP, phoQ, rfc, poxA, galU, mviA, sodC, recA, ssrA, sirA, inv, hilA, rpoE, flgM, tonB, slyA, and any combination thereof. Exemplary attenuating mutations may be aroA, aroC, aroD, cdt, cya, crp, phoP, phoQ, ompR, galE, and htrA.

In certain embodiments, the above nucleic acid sequences may be placed under the control of a sugar regulated promoter wherein the sugar is present during in vitro growth of the recombinant bacterium, but substantially absent within an animal or human host. The cessation in transcription of the nucleic acid sequences listed above would then result in attenuation and the inability of the recombinant bacterium to induce disease symptoms.

B. Additional Mutations

In some embodiments, the recombinant bacterium comprises a deletion in an endogenous recF gene, which encodes the DNA replication and repair protein RecF. In some embodiments, the deletion of the endogenous recF gene is a partial deletion. In some embodiments, the deletion of the endogenous recF gene is a full-length deletion. In some embodiments, the endogenous recF gene is genetically altered to insert a transcriptional terminator in the open reading frame of the gene.

In some embodiments, the recombinant bacterium comprises a deletion in an endogenous recJ gene, which encodes the exonuclease RecJ. In some embodiments, the deletion of the endogenous recJ gene is a partial deletion. In some embodiments, the deletion of the endogenous recJ gene is a full-length deletion. In some embodiments, the endogenous recJ gene is genetically altered to insert a transcriptional terminator in the open reading frame of the gene.

The bacterium may also be modified to create a balanced-lethal host-vector system, although other types of systems may also be used (e.g., creating complementation heterozygotes). For the balanced-lethal host-vector system, the bacterium may be modified by manipulating its ability to synthesize various essential constituents needed for synthesis of the rigid peptidoglycan layer of its cell wall. In one example, the constituent is diaminopimelic acid (DAP). Various enzymes are involved in the eventual synthesis of DAP.

In some embodiments, the recombinant bacterium comprises a deletion in an endogenous asd gene. In some embodiments, the deletion of the endogenous asd gene is a partial deletion. In some embodiments, the deletion of the endogenous asd gene is a full-length deletion. In some embodiments, the endogenous asd gene is genetically altered to insert a transcriptional terminator in the open reading frame of the gene. In some embodiments, the promoter of a endogenous asd gene is altered to include one or more regulatory elements (e.g., a sugar-responsive promoter). In one example, the bacterium is modified by using a ΔasdA mutation to eliminate the bacterium's ability to produce β-aspartate semialdehyde dehydrogenase, an enzyme essential for the synthesis of DAP. Other mutations that result in the abolition of the synthesis of DAP include, but are not limited to, dapA, dapB, dapC, dapD, dapE, dapF, and asd (see, e.g., U.S. Pat. No. 6,872,547, incorporated herein by reference). Other modifications that may be employed include modifications to a bacterium's ability to synthesize D-alanine or to synthesize D-glutamic acid (e.g., ΔmurI mutations), which are both unique constituents of the peptidoglycan layer of the bacterial cell wall.

Similarly, various embodiments may comprise the araC $P_{araBAD}$ c2 gene cassette inserted into the asd nucleic acid sequence that encodes aspartate semialdehyde dehydrogenase. Since the araC nucleic acid sequence is transcribed in a direction that could lead to interference in the expression of adjacent nucleic acid sequences and adversely affect vaccine strain performance, a transcription termination (TT) sequence is generally inserted 3' to the araC nucleic acid sequence. The chromosomal asd nucleic acid sequence is typically inactivated to enable use of plasmid vectors encoding the wild-type asd nucleic acid sequence in the balanced lethal host-vector system. This allows for stable maintenance of plasmids in vivo in the absence of any drug resistance attributes that are not permissible in live bacterial vaccines. In some of these embodiments, the wild-type asd nucleic acid sequence may be encoded by the vector described herein. The vector enables the regulated expression of an antigen encoding sequence through the repressible promoter.

C. Repressor Regulatory Systems

In some embodiments, the recombinant bacterium comprises a nucleic acid (e.g., a gene) that is operably linked to a repressor-regulatable promoter to facilitate the regulatable expression of the gene. Thus, in some embodiments, the recombinant bacterium comprises a nucleic acid comprising a gene encoding a repressor. In some embodiments, the gene encoding the repressor is operably-linked to a regulatable promoter. Methods of chromosomally integrating a nucleic acid sequence encoding a repressor operably-linked to a regulatable promoter are known in the art and detailed in the examples. In some embodiments, the nucleic acid sequence encoding a repressor is not integrated into a chromosomal locus such that the ability of the bacterium to colonize a host cell is disrupted. In some embodiments, the recombinant bacterium comprises a nucleic acid encoding a repressor that is integrated into the relA locus of the bacterial chromosome. In some embodiments, the recombinant bacterium comprises a nucleic acid encoding a repressor that is integrated into the endA locus of the bacterial chromosome. In some embodiments, the recombinant bacterium comprises at least one nucleic acid sequence encoding a repressor. In some embodiments, the recombinant bacterium comprises at least two, at least three, at least four, at least five, at least six or more nucleic acids encoding a repressor. In some embodiments, the nucleic acid encoding the repressor is present on a plasmid in the bacterium. In some embodiments, the nucleic acid encoding the repressor is located in the bacterial chromosome. If there is more than one nucleic acid sequence encoding a repressor, each nucleic acid sequence encoding a repressor may be operably linked to a regulatable promoter, such that each promoter is regulated by the same compound or condition. Alternatively, each nucleic acid sequence encoding a repressor may be operably linked to a regulatable promoter, each of which is regulated by a different compound or condition.

As used herein, a "repressor" refers to a biomolecule that represses the transcriptional activity of a promoter. In some embodiments, the repressor is synthesized by the recombinant bacterium in high enough quantities during in vitro culture, such that the transcription of a nucleic acid that is operably linked to a repressor-regulatable promoter is repressed. This may be particularly advantageous if, for example, expression of the product encoded by said nucleic acid impedes the in vitro growth of the bacterium, and/or the ability of the bacterium to infect and/or colonize a subject. In some embodiments, the nucleic acid that is operably-linked to the repressor-regulatable promoter expresses an antigen of interest. In some embodiments, the concentration of the repressor within the cell gradually decreases with each cell division cycle after transcription of the gene encoding the repressor decreases or ceases (e.g., in vivo). The use of a particular repressor, as described herein, may depend, in part, on the species, subspecies, strain or serovar of the recombinant bacterium being used. In some embodiments, the repressor is derived from the same species (e.g., the same bacterial species or the same phage) from which the repressor-regulatable promoter is derived. In some embodiments the repressor is not derived from the same bacterial species as the bacterial species in which the repressor is expressed. For example, in some embodiments, the repressor is derived from E. coli if the recombinant bacterium is of the genus Salmonella. Other suitable repressors include repressors derived from a bacteriophage.

A nucleic acid sequence encoding a repressor and regulatable promoter detailed above may be modified so as to optimize the expression level of the nucleic acid sequence encoding the repressor. The optimal level of expression of the nucleic acid sequence encoding the repressor may be estimated, or may be determined by experimentation. Such a determination should take into consideration whether the repressor acts as a monomer, dimer, trimer, tetramer, or higher multiple, and should also take into consideration the copy number of the vector encoding the antigen of interest. In an exemplary embodiment, the level of expression is optimized so that the repressor is synthesized while in a permissive environment (i.e., in vitro growth) at a level that substantially inhibits the expression of the nucleic acid encoding an antigen of interest, and is substantially not synthesized in a non-permissive environment, thereby allowing expression of the nucleic acid encoding an antigen of interest.

In some embodiments, the recombinant bacterium described herein is modified to comprise a nucleic acid comprising a lacI gene, which encodes the LacI repressor protein. The expression of the lacI-encoded repressor in the recombinant bacterium described herein may be used to regulate the expression of a gene encoding an antigen of interest expressed by the bacterium. For example, in some embodiments, the expression of the lacI gene is regulated by a sugar-regulatable promoter (e.g., an arabinose-regulatable promoter). When cultured in the presence of arabinose, the recombinant bacterium will synthesize the LacI repressor protein, which in turn will repress the expression of a gene encoding an antigen of interest that is operably-linked to a LacI-responsive promoter (e.g., P$_{trc}$, P$_{lac}$, P$_{T7lac}$ and P$_{tac}$). Upon administration to the subject and in the absence of a source of arabinose, the synthesis of LacI repressor ceases, leading to de-repression of the LacI-responsive promoter and the subsequence causing expression of the antigen of interest. The concentration of Lac in the cell decreases by about half at each cell division in vivo, leading to a gradual decreased level of repression and gradual increased synthesis of the antigen of interest.

In some embodiments, the nucleic acid comprising a lac gene is located on a plasmid in the bacterium. In some embodiments, the nucleic acid comprising a lacI gene is located on a chromosome of the bacterium. In some embodiments, the nucleic acid comprising a lacI gene is located at the chromosomal locus corresponding to the locus of an endogenous –relA gene that has been deleted or altered in the bacterial chromosome. In some embodiments, the recombinant bacterium is modified to comprise a nucleic acid comprising a lacI gene, whereby an endogenous copy of the lacI gene in the bacterial chromosome has been altered and/or deleted.

In some embodiments, the nucleic acid comprises an *Escherichia coli* lacI gene. The nucleic acid sequence of the *E. coli* lacI gene is provided below:

(SEQ ID NO: 9)
gtgaaaccagtaacgttatacgatgtcgcagagtatgccggtgtctctta tcagaccgtttcccgcgtggtgaaccaggccagccacgtttctgcgaaaa cgcgggaaaaagtggaagcggcgatggcggagctgaattacattcccaac cgcgtggcacaacaactggcgggcaaacagtcgttgctgattggcgttgc cacctccagtctggccctgcacgcgccgtcgcaaattgtcgcggcgatta aatctcgcgccgatcaactgggtgccagcgtggtggtgtcgatggtagaa cgaagcggcgtcgaagcctgtaaagcggcggtgcacaatcttctcgcgca acgcgtcagtgggctgatcattaactatccgctggatgaccaggatgcca ttgctgtggaagctgcctgcactaatgttccggcgttatttcttgatgtc tctgaccagacacccatcaacagtattattttctcccatgaagacggtac gcgactgggcgtggagcatctggtcgcattgggtcaccagcaaatcgcgc tgttagcgggcccattaagttctgtctcggcgcgtctgcgtctggctggc tggcataaatatctcactcgcaatcaaattcagccgatageggaacggga aggcgactggagtgccatgtccggttttcaacaaaccatgcaaatgctga atgagggcatcgttcccactgcgatgctggttgccaacgatcagatggcg ctgggcgcaatgcgcgccattaccgagtccgggctgcgcgttggtgcgga tatctcggtagtgggatacgacgataccgaagacagctcatgttatatcc cgccgttaaccaccatcaaacaggattttcgcctgctggggcaaaccagc gtggaccgcttgctgcaactctctcagggccaggcggtgaagggcaatca gctgttgcccgtctcactggtgaaaagaaaaaccaccctggcgcccaata cgcaaaccgcctctccccgcgcgttggccgattcattaatgcagctggca cgacaggtttcccgactggaaagcgggcagtga.

The amino acid sequence of the *E. coli* LacI protein encoded by the nucleic acid of SEQ ID NO: 9 is provided below:

(SEQ ID NO: 10)
MKPVTLYDVAEYAGVSYQTVSRVVNQASHVSAKTREKVEAAMAELNYIPN

RVAQQLAGKQSLLIGVATSSLALHAPSQIVAAIKSRADQLGASVVVSMVE

RSGVEACKAAVHNLLAQRVSGLIINYPLDDQDAIAVEAACTNVPALFLDV

SDQTPINSIIFSHEDGTRLGVEHLVALGHQQIALLAGPLSSVSARLRLAG

WHKYLTRNQIQPIAEREGDWSAMSGFQQTMQMLNEGIVPTAMLVANDQMA

LGAMRAITESGLRVGADISVVGYDDTEDSSCYIPPLTTIKQDFRLLGQTS

VDRLLQLSQGQAVKGNQLLPVSLVKRKTTLAPNTQTASPRALADSLMQLA

RQVSRLESGQ.

In some embodiments, the nucleic acid comprises a lacI gene, wherein the lacI gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 9. In some embodiments, the nucleic acid comprises a lacI gene, wherein the lacI gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 9.

In some embodiments, the nucleic acid comprises a nucleic acid sequence encoding a Lac protein, wherein said Lac protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 10. In some embodiments, the nucleic acid comprises a nucleic acid sequence encoding a LacI protein, wherein said LacI protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 10.

In some embodiments, the nucleic acid comprises a lacI gene that is operably-linked to a regulatable promoter (e.g., a sugar-regulatable promoter). In some embodiments, the nucleic acid comprises a lacI gene that is operably-linked to a sugar-regulatable promoter. In some embodiments, the sugar regulatable promoter exhibits increased activity (e.g., increased transcription) in the presence of a specific sugar and decreased activity in the absence of a sugar. In some embodiments, the nucleic acid comprises a lacI gene that is operably-linked to a rhamnose-regulatable promoter (e.g., a sugar-regulatable promoter). In some embodiments, the nucleic acid comprises a lac gene that is operably-linked to an arabinose-regulatable promoter. In some embodiments, the arabinose-regulatable promoter is $P_{araBAD}$. In some embodiments, the recombinant bacterium comprises the mutation ΔrelA::araC $P_{araBAD}$ lac TT.

D. Antigens

In some embodiment, the recombinant bacterium comprises a nucleic acid encoding an antigen of interest. As used herein, "antigen" refers to a biomolecule capable of eliciting an immune response in a host. In some embodiments, an antigen may be a protein, or fragment of a protein. In some embodiments, the recombinant bacterium comprises a nucleic acid (e.g., a plasmid) encoding an antigen of interest, wherein the nucleic acid is expressed by the host cell (e.g., a DNA vaccine). In an exemplary embodiment, the antigen elicits a protective immune response in a subject.

As used herein, "protective" means that the immune response contributes to the lessening of any symptoms associated with infection of a host with the pathogen the antigen was derived from or designed to elicit a response against. For example, a protective antigen from a pathogen, such as Salmonella, may induce an immune response that helps to ameliorate symptoms associated with Salmonella infection or reduce the morbidity and mortality associated with infection with the pathogen or may reduce the ability of Salmonella to infect and colonize the host. The use of the term "protective" in this disclosure does not necessarily require that the host is completely protected from the effects of the pathogen.

In some embodiments, the antigen of interest is an antigen derived from an infectious agent. In some embodiments, the antigen of interest is derived from an infectious agent selected from the group consisting of a virus, a bacterium, a protozoan, a prion, a fungus, and a helminth. In some embodiments, the antigen of interest is derived from a bacterium. In some embodiments, the antigen of interest is a Salmonella antigen. In some embodiments, the Salmonella antigen is selected from the group FliC, FliC180, OmpC, OmpD, OmpF, SseB, and SseI. In some embodiments, the antigen of interest is a viral antigen. In some embodiments, the antigen of interest is an influenza antigen. In some embodiments, the influenza antigen is hemagglutinin or neuraminidase, if delivered by a DNA vaccine. In some embodiments, the antigen of interest is an antigen associated with cancer. In some embodiments, the antigen associated with cancer is selected from the group consisting of MAGE-A, MAGE-C1, BAGE, GAGE, XAGE, NY-ESO1 (also known as CTAG1B and LAGE2), LAGE1 (also known as CTAG2) and survivin.

Alternatively, antigens may be derived from gametes, provided they are gamete specific, and may be designed to block fertilization. In another alternative, antigens may be tumor antigens, and may be designed to decrease tumor growth. It is specifically contemplated that antigens from organisms newly identified or newly associated with a disease or pathogenic condition, or new or emerging pathogens of animals or humans, including those now known or identified in the future, may be expressed by a bacterium detailed herein. Furthermore, antigens are not limited to those from pathogenic organisms.

Immunogenicity of the bacterium may be augmented and/or modulated by constructing strains that also express sequences for cytokines, adjuvants, and other immunomodulators.

Some examples of microorganisms useful as a source for antigen are listed below. These may include microorganisms for the control of plague caused by *Yersinia pestis* and other *Yersinia* species such as *Y. pseudotuberculosis* and *Y. enterocolitica*, for the control of gonorrhea caused by *Neisseria gonorrhoea*, for the control of syphilis caused by *Treponema pallidum*, and for the control of venereal diseases as well as eye infections caused by *Chlamydia trachomatis*. Species of *Streptococcus* from both group A and group B, such as those species that cause sore throat or heart diseases, *Streptococcus equi*, which causes strangles in equines, *Streptococcus mutans*, which causes cavities, and *Streptococcus pneumoniae, Erysipelothrix rhusiopathiae, Neisseria meningitidis, Mycoplasma pneumoniae* and other *Mycoplasma*-species, *Hemophilus influenza, Bordelella perlussis, Mycobaclerium tuberculosis, Mycobacterium leprae*, other *Bordetella* species, *Escherichia coli, Brucella abortus, Pasteurella hemolytica* and *P. multocida, Vibrio cholera, Shigella* species, *Borrellia* species, *Bartonella* species, *Heliobacter pylori, Campylobacter* species, *Pseudomonas* species, *Moraxella* species, *Brucella* species, *Francisella* species, *Aeromonas* species, *Actinohacillus* species, *Clostridium* species (such as *C. perfringens*), *Rickettsia* species, *Bacillus* species, *Coxiella* species, *Ehrlichia* species, *Listeria* species, and *Legionella pneumophila* are additional examples of bacteria within the scope of this disclosure from which antigen nucleic acid sequences could be obtained.

Viral antigens may also be used. Viral antigens may be used in antigen delivery microorganisms directed against viruses, either DNA or RNA viruses, for example from the classes Papovavirus, Adenovirus, Herpesvirus, Poxvirus, Parvovirus, Reovirus, Picornavirus, Myxovirus, Paramyxovirus, Flavivirus or Retrovirus. Antigens may also be derived from pathogenic fungi, protozoa and parasites. However, means of antigen delivery or sequences encoding the antigen depends on the type of antigen and/or virus.

In certain embodiments, an antigen may comprise a B cell epitope or a T cell epitope. Alternatively, an antigen to which an immune response is desired may be expressed as a fusion to a carrier protein that contains a strong promiscuous T cell epitope and/or serves as an adjuvant and/or facilitates presentation of the antigen to enhance, in all cases, the immune response to the antigen or its component part. This can be accomplished by methods known in the art. Fusion to tenus toxin fragment C, CT-B, LT-B and hepatitis virus B core are particularly useful for these purposes, although other epitope presentation systems are well known in the art.

In further embodiments, a nucleic acid sequence encoding an antigen may comprise a secretion signal.

As stated above, the level of synthesis of an antigen of interest may be optimized by modifying the nucleic acid sequence encoding the repressor and/or promoter. As used herein, "modify" refers to an alteration of the nucleic acid sequence of the repressor and/or promoter that results in a change in the level of transcription of the nucleic acid sequence encoding the repressor, or that results in a change in the level of synthesis of the repressor. For instance, in one embodiment, modify may refer to altering the start codon of the nucleic acid sequence encoding the repressor. Generally speaking, a GTG or TTG start codon, as opposed to an ATG start codon, may decrease translation efficiency ten-fold. In another embodiment, modify may refer to altering the Shine-Dalgarno (SD) sequence of the nucleic acid sequence encoding the repressor. The SD sequence is a ribosomal binding site generally located 6-7 nucleotides upstream of the start codon. The SD consensus sequence is AGGAGG, and variations of the consensus sequence may alter translation efficiency. In yet another embodiment, modify may refer to altering the distance between the SD sequence and the start codon. In still another embodiment, modify may refer to altering the −35 sequence for RNA polymerase recognition. In a similar embodiment, modify may refer to altering the −10 sequence for RNA polymerase binding. In an additional embodiment, modify may refer to altering the number of nucleotides between the −35 and −10 sequences. In an alternative embodiment, modify may refer to optimizing the codons of the nucleic acid sequence encoding the repressor to alter the level of translation of the mRNA encoding the repressor. For instance, non-A rich codons initially after the start codon of the nucleic acid sequence encoding the repressor may not maximize translation of the mRNA encoding the repressor. Similarly, the codons of the nucleic acid sequence encoding any of the proteins described herein may be codon-optimized, i.e., altered so as to mimic the codons from highly synthesized proteins of a particular organism. In a further embodiment, modify may refer to altering the GC content of the nucleic acid sequence encoding the repressor to change the level of translation of the mRNA encoding the repressor. Methods of modifying a nucleic acid sequence are known in the art.

In some embodiments, more than one modification or type of modification may be performed to optimize the expression level of a nucleic acid described herein (e.g., a nucleic acid encoding a repressor or antigen of interest). For instance, at least one, two, three, four, five, six, seven, eight, or nine modifications, or types of modifications, may be performed to optimize the expression level of a nucleic acid described herein. By way of non-limiting example, when the repressor is LacI, then the nucleic acid sequence of LacI and the promoter may be altered so as to increase the level of LacI synthesis. In one embodiment, the start codon of the LacI repressor may be altered from GTG to ATG. In another embodiment, the SD sequence may be altered from AGGG to AGGA. In yet another embodiment, the codons of lac may be optimized according to the codon usage for highly synthesized proteins of *Salmonella*. In a further embodiment, the start codon of lac may be altered, the SD sequence may be altered, and the codons of lac may be optimized.

In some embodiments, the recombinant bacterium comprises a nucleic acid that is located in a plasmid or vector. As used herein, "vector" refers to an autonomously replicating nucleic acid unit. The present disclosure can be practiced with any known type of vector, including viral, cosmid, phasmid, and plasmid vectors. The most preferred type of vector is a plasmid vector. In some embodiments, the plasmid or vector is a high copy plasmid. In some embodiments, the plasmid or vector is a low copy plasmid or vector.

As is well known in the art, plasmids and other vectors may possess a wide array of promoters, multiple cloning sequences, transcription terminators, etc., and vectors may be selected so as to control the level of expression of the nucleic acid sequence encoding an antigen by controlling the relative copy number of the vector. In some instances in which the vector might encode a surface localized adhesin as the antigen, or an antigen capable of stimulating T-cell immunity, it may be preferable to use a vector with a low copy number such as at least two, three, four, five, six, seven, eight, nine, or ten copies per bacterial cell. A non-limiting example of a low copy number vector may be a vector comprising the pSC101 ori.

In some embodiments, the plasmid comprises a nucleic acid sequence encoding an aspartate-semialdehyde dehydrogenase gene (e.g., asdA). These plasmids may be advantageously used to complement a bacterium that comprises an aspartate-semialdehyde dehydrogenase gene mutation (e.g., asdA). In some embodiments, the plasmid is selected from the group consisting of pYA3342, pYA3337, and pYA3332.

In other cases, an intermediate copy number vector might be optimal for inducing desired immune responses. For instance, an intermediate copy number vector may have at least 10, 11, 12, 13, 14, 15, 16, 17, 18, 19, 20, 21, 22, 23, 24, 25, 26, 27, 28, 29, or 30 copies per bacterial cell. A non-limiting example of an intermediate copy number vector may be a vector comprising the p15A ori.

In still other cases, a high copy number vector might be optimal for the induction of maximal antibody responses. A high copy number vector may have at least 31, 35, 40, 45, 50, 55, 60, 65, 70, 75, 80, 85, 90, 95, or 100 copies per bacterial cell. In some embodiments, a high copy number vector may have at least 100, 125, 150, 175, 200, 225, 250, 275, 300, 325, 350, 375, or 400 copies per bacterial cell. Non-limiting examples of high copy number vectors may include a vector comprising the pBR on or the pUC ori.

Additionally, vector copy number may be increased by selecting for mutations that increase plasmid copy number. These mutations may occur in the bacterial chromosome but are more likely to occur in the plasmid vector.

Preferably, vectors used herein do not comprise antibiotic resistance markers to select for maintenance of the vector.

Promoters for use in the embodiments described herein are known in the art. One of skill in the art would recognize that the selection of a repressor dictates, in part, the selection of the promoter to be used to regulate the expression of a nucleic acid described herein. For instance, if the repressor is LacI, then the promoter may be selected from the group consisting of LacI responsive promoters, such as $P_{trc}$, $P_{lac}$, $P_{T7lac}$, $P_{tac}$, $P_{ompA\ lacO}$, and $P_{lpp\ lacO}$. If the repressor is C2, then the promoter may be selected from the group consisting of C2 responsive promoters, such as P22 promoters $P_L$ and $P_R$. If the repressor is C1, then the promoter may be selected from the group consisting of C1 responsive promoters, such as λ promoters $P_L$ and $P_R$.

In each embodiment herein, the promoter regulates expression of a nucleic acid sequence. In some embodiments, the promoter comprises a regulatory sequence controlled by a repressor, such that expression of the nucleic acid sequence is repressed when the repressor is synthesized (e.g., during in vitro growth of the bacterium), but expression of the nucleic acid sequence encoding an antigen is high when the repressor is not synthesized (e.g., in vivo). Generally speaking, the concentration of the repressor will decrease with every cell division after expression of the gene encoding the repressor ceases. In some embodiments, the concentration of the repressor decreases such that high levels of expression of the nucleic acid sequence that is being regulated is achieved after about 2, 3, 4, 5, 6, 7, 8, 9, 10, 11, or 12 divisions of the bacterium. In an exemplary embodiment, the concentration of the repressor decreases enough to allow high-level expression of the nucleic acid sequence encoding an antigen after about 5 divisions of the bacterium in vivo.

In certain embodiments, the promoter may comprise other regulatory elements. For instance, the promoter may comprise lacO if the repressor is LacI. This is the case with the lipoprotein promoter $P_{lpp\ lacO}$ that is regulated by LacI since it possesses the LacI binding domain lacO. In one embodiment, the repressor is a LacI repressor and the promoter is $P_{trc}$.

In some embodiments, the expression of the nucleic acid sequence regulated by a repressor is repressed in vivo. Expression may be "repressed" or "partially repressed" when it is about 50%, 45%, 40%, 35%, 30%, 25%, 20%, 15%, 10%, 5%, 1%, or even less than 1% of the expression under non-repressed conditions. Thus although the level of expression under conditions of "complete repression" might be exceeding low, it is likely to be detectable using very sensitive methods since repression can never by absolute.

Conversely, the expression of the nucleic acid sequence encoding the antigen should be high when the expression of the repressor is repressed. For instance, if the repressor is not synthesized during growth of the recombinant bacterium in a host, the expression of the nucleic acid under the control of the repressor will be high. As used herein, "high level" expression refers to expression that is strong enough to elicit an immune response to the antigen. Consequently, the copy number correlating with high level expression can and will vary depending on the antigen and the type of immune response desired. Methods of determining whether an antigen elicits an immune response such as by measuring antibody levels or antigen-dependent T cell populations or antigen-dependent cytokine levels are known in the art, and methods of measuring levels of expression of antigen encoding sequences by measuring levels of mRNA transcribed or by quantitating the expression level of a protein are also known in the art.

In each of the above embodiments, a recombinant bacterium capable of regulated expression may also be attenuated. "Attenuated" refers to the state of the bacterium wherein the bacterium has been weakened from its wild-type fitness by some form of recombinant or physical manipulation. This includes altering the genotype of the bacterium to reduce its ability to cause disease. However, the bacterium's ability to colonize the gut (in the case of *Salmonella*) and induce immune responses is, preferably, not substantially compromised.

In an exemplary embodiment, a recombinant bacterium may be attenuated as described above. In which case, both regulated attenuation and regulated expression of an antigen encoding sequence may be dependent upon a sugar regulatable system. Consequently, the concentration of sugar (e.g., arabinose) needed for optimal expression of the regulated antigen encoding sequence may not be the same as the concentration for optimal expression of attenuation. In an exemplary embodiment, the concentration of arabinose for the optimization of both regulated attenuation and regulated expression of sequences encoding antigen will be substantially the same.

Accordingly, the promoter and/or the nucleic acid sequence encoding an attenuation protein may be modified to optimize the system. Methods of modification are detailed above. Briefly, for example, the SD ribosome binding sequence may be altered, and/or the start codon may be altered from ATG to GTG for the nucleic acid sequences fhr and phoPQ, so that the production levels of Fur and PhoPQ are optimal for both the regulated attenuation phenotype and the regulated expression when growing strains with a given concentration of arabinose. One of skill in the art will appreciate that other nucleic acid sequences, in addition to fur and phoPQ, may also be altered as described herein in combination with other well-known protocols. In addition, these attenuating nucleic acid sequences may be regulated by other systems using well-established protocols known to one of skill in the art. For example, they may be regulated using with promoters dependent on addition of maltose, rhamnose, or xylose rather than arabinose.

II. Pharmaceutical Compositions

A recombinant bacterium may be administered to a host as a pharmaceutical composition. In some embodiments, the pharmaceutical composition may be used as a vaccine to elicit an immune response to the recombinant bacterium, including any antigens that may be synthesized and delivered by the bacterium. In an exemplary embodiment, the immune response is protective. Immune responses to antigens are well studied and widely reported.

Pharmaceutical compositions may be administered to any host capable of mounting an immune response. Such hosts may include all vertebrates, for example, mammals, including domestic animals, agricultural animals, laboratory animals, and humans, and various species of birds, including domestic birds and birds of agricultural importance. Preferably, the host is a warm-blooded animal. In one embodiment, the host is a cow. In some embodiments, the host is an equine. In another embodiment, the host is an avian. In another embodiment, the host is a human. The pharmaceutical composition can be administered to the subject as a prophylactic or for treatment purposes.

In some embodiments, the recombinant bacterium is alive when administered to a host in a pharmaceutical composition described herein. Suitable vaccine composition formulations and methods of administration are detailed below.

A pharmaceutical composition comprising a recombinant bacterium may optionally comprise one or more possible additives, such as carriers, preservatives, stabilizers, adjuvants, and other substances.

In one embodiment, the pharmaceutical composition comprises an adjuvant. Adjuvants are optionally added to increase the ability of the vaccine to trigger, enhance, or prolong an immune response. In exemplary embodiments, the use of a live attenuated recombinant bacterium may act as a natural adjuvant. In some embodiments, the recombinant bacterium synthesizes and secretes an immune modulator. Additional materials, such as cytokines, chemokines, and bacterial nucleic acid sequences naturally found in bacteria, like CpG, are also potential vaccine adjuvants.

In some embodiments, the pharmaceutical composition comprises buffered saline (e.g., phosphate-buffered saline (PBS)).

In some embodiments, the pharmaceutical composition comprises a food product.

In another embodiment, the pharmaceutical may comprise a pharmaceutical carrier (or excipient). Such a carrier may be any solvent or solid material for encapsulation that is non-toxic to the inoculated host and compatible with the recombinant bacterium. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995). When used for administering via the bronchial tubes, the pharmaceutical composition is preferably presented in the form of an aerosol.

In some embodiments, the pharmaceutical composition is delivered to a farm animal (e.g., poultry). In some embodiments, the pharmaceutical composition is delivered as a course spray (e.g., for use in hatcheries for delivery to poultry). In some embodiments, the pharmaceutical composition is delivered in the drinking water.

Care should be taken when using additives so that the live recombinant bacterium is not killed, or have its ability to effectively colonize lymphoid tissues such as the GALT, NALT and BALT compromised by the use of additives. Stabilizers, such as lactose or monosodium glutamate (MSG), may be added to stabilize the pharmaceutical composition against a variety of conditions, such as temperature variations or a freeze-drying process. The recombinant bacterium may also be co-administered with glutamate and/or arginine as described herein.

The dosages of a pharmaceutical composition can and will vary depending on the recombinant bacterium, the regulated antigen, and the intended host, as will be appreciated by one of skill in the art. Generally speaking, the dosage need only be sufficient to elicit a protective immune response in a majority of hosts. Routine experimentation may readily establish the required dosage. Typical initial dosages of vaccine for oral administration could be about $1 \times 10^7$ to $1 \times 10^{10}$ CFU depending upon the age of the host to be immunized. Administering multiple dosages may also be used as needed to provide the desired level of protective immunity.

In order to stimulate a preferred response of the GALT, NALT or BALT cells, administration of the pharmaceutical composition directly into the gut, nasopharynx, or bronchus is preferred, such as by oral administration, intranasal administration, gastric intubation or in the form of aerosols, although other methods of administering the recombinant bacterium, such as intravenous, intramuscular, subcutaneous injection or intramammary, intrapenial, intrarectal, vaginal administration, or other parenteral routes, are possible, e.g., for anti-cancer applications.

In some embodiments, these compositions are formulated for administration by injection (e.g., intraperitoneally, intravenously, subcutaneously, intradermally, intramuscularly, etc.).

In another embodiment, the disclosure provides a method for eliciting an immune response against an antigen in a host. The method comprises administering to the host an effective amount of a pharmaceutical composition comprising a recombinant bacterium described herein.

In still another embodiment, a recombinant bacterium may be used in a method for eliciting an immune response against a pathogen in an individual in need thereof. The method comprises administrating to the host an effective amount of a pharmaceutical composition comprising a recombinant bacterium as described herein. In a further embodiment, a recombinant bacterium described herein may be used in a method for ameliorating one or more symptoms of an infectious disease in a host in need thereof. The method comprises administering an effective amount of a pharmaceutical composition comprising a recombinant bacterium as described herein.

EXAMPLES

The present invention is further illustrated by the following examples that should not be construed as limiting in any way. The contents of all cited references, including literature references, issued patents, and published patent applications, as cited throughout this application are hereby expressly incorporated herein by reference. It should further be understood that the contents of all the figures and tables attached hereto are also expressly incorporated herein by reference.

Example 1: Background

Protective immunity to *Salmonella* depends on the combined action of specific antibodies, B cells and T-cell-acquired immune responses (52-56). Effective clearance of primary infection requires a Th1 response, with the help of antibody limiting bacteremia (55, 57). Antibody responses are important to achieve protection against *Salmonella* infection (58-60), as seen for protection against S. Typhi in mice (61) and humans (62-64). RASVs induce all three branches of the immune system (i.e., mucosal antibody and cellular responses, and systemic antibody and cellular responses). All three of branches of the immune system are important in conferring protective immunity to *Salmonella* and all pathogens that colonize on or invade through the mucosal surface.

*Salmonella* possess a number of immunologically-related cross-reactive antigens. These include the LPS core polysaccharide that is the same in most, if not all, *S. enterica* serovars (65, 66) except for S. Arizonae (67, 68). In addition, OMPs, although possessing micro-heterogeneity, nevertheless share antigenic determinants (69), as well as iron-regulated outer membrane proteins (IROMPs) (70) that are required for iron acquisition (70), an essential important function for pathogen success within an infected animal.

*Salmonella* vaccines can be used to display wild-type surface antigenic determinants in vitro and during the initial phase of infection through mucosal surfaces in the orally immunized host and then cease to synthesize LPS O-antigen side chains by a Δpmi mutation (71-74) and to constitutively synthesize IROMPs in internal organs (75, 76) by a $\Delta P_{fur}$:: TT araC $P_{araBAD}$ fur ($\Delta P_{fur}$) deletion-insertion mutation (77). S. Typhimurium strains with the Δpmi mutation are not completely attenuated, but have high immunogenicity, efficacy in enhancing induction of high antibody titers to cross-protective OMPs, IROMPs (76) and conserved LPS core (78, 79). However, the LPS core is not fully exposed because there are still two sugars attached to the LPS core. Strains with the Δpmi mutation also enhance the production of Outer Membrane Vesicles (OMVs) that can deliver recombinant protective antigens for enhanced protective immunity (80). The $\Delta P_{fur}$ mutation enables expression of the fur gene to be solely dependent on the presence of arabinose (75, 81, 82) and is blind to the concentration of iron to achieve in vivo a high constitutive synthesis level of all components for iron acquisition including immunologically cross-reactive IROMPs. Immune responses to highly immunogenic IROMPs are effective in preventing septicemic infection with enteropathogens (83). Antibodies induced to IROMPs from one bacterial serotype can recognize IROMPs synthesized by other serotypes (84). Two inactivated vaccines based on IROMP overproduction are licensed to protect against salmonellosis in poultry (85, 86).

Live *Salmonella* delivering both surface polysaccharides and OMPs to the immune system are more immunogenic than glycoconjugate vaccines. *Salmonella* spontaneously releases 50 to 90 nm bleb-like particles of outer cell wall membrane (87-89). These blebs, called GMMA (Generalized Modules for Membrane Antigens) or outer membrane vesicles, constitute an enriched source of outer membrane-associated antigens in their native conformation and correct orientation. GMMA or outer membrane vesicles provide significant advantages over recombinant proteins because they contain multiple pathogen-associated molecular patterns (PAMPs), including TLR ligands, which have the potential to act as self-adjuvants in the immune responses they elicit (90-95). GMMA or outer membrane vesicles are also different from detergent extracted OMPs which lose a number of outer membrane components, like lipoproteins, and thus result in reduced immunogenicity. GMMA or outer membrane vesicles are currently being explored as vaccines for meningococcus (96, 97), *Shigella* (87) and *Salmonella* (27). Preclinical studies with candidate GMMA or outer membrane vesicles vaccines indicate good immunogenicity and broad cross protective immunity against a variety of strains (98). A prototype meningococcal GMMA or outer membrane vesicles has been tested in one Phase 1 clinical trial without adverse effects (99) and a prototype *Shigella* GMMA or outer membrane vesicles is planned for a Phase 2 trial. GMMA or outer membrane vesicles production can be enhanced by deletion of the tolR gene (87, 100, 101), as seen in tolR mutants of *Salmonella* and *Shigella* (87, 102). Deletions of genes, such as htrB (88) and msbB (103) for lipid A modification, can reduce reactogenicity. Although the new GMMA or outer membrane vesicles vaccines have a reduced number of purification steps because they are spontaneously released by appropriate vaccine bacterial seed strains, downstream procedures, like complex tangential flow filtration, for GMMA or outer membrane vesicles purification are still needed (87, 104, 105). In contrast, the instant disclosure provides an in vivo GMMA or outer membrane vesicles production system to omit downstream purification procedures without compromising the efficiency.

Among surface-exposed or secreted protective antigens in *Salmonella*, 6 antigens, FliC, OmpC, OmpD, OmpF, SseB, and SseI, may be used (106-113). These antigens are not the most abundant proteins in *Salmonella* (106). FliC synthesis is even deregulated at systemic sites (114-116). Preclinical studies in mice have demonstrated that immunization with those above antigens could protect against *Salmonella* challenge (57, 111, 117-120). OmpC and F induce long-lasting antibody responses in mice (121) and have been found to be safe and immunogenic when tested in a Phase 1 study in humans (122). OmpD is a key target for a protective B1b cell antibody response independent of T cells (57, 111) and is conserved in all serovars of *Salmonella* except serovar Typhi (123, 124). The SPI-2 translocon subunit SseB plays the critical function for the secretion of T3SS effector and replication of *Salmonella* in the cell (125). It is a serodominant target of adaptive immunity in children with *Salmonella* bacteremia (120) and encompasses multiple epitopes for CD4 T-cell immunity in human volunteers (108, 120, 126). Another SPI-2 effector, SseI, plays a role in modulating the migration of infected cells, and is required for long-term systemic infection (127-131). Preserving the correct conformation of such antigens is critical as revealed by the failure of recombinant *Salmonella* porins to protect mice (132). RASV enables delivery of these antigens in their correct conformation and orientation with high levels of production, combined with the self-adjuvanting properties of *Salmonella* that deliver innate signals through TLR ligands and other PAMPs to induce *Salmonella*-specific T-cell and B-cell immunity.

Disclosed herein is an innovative RASV platform to overproduce protective *Salmonella* antigens in vivo. This system is a unique triple sugar regulated system, double shutoff of O-antigen synthesis by rhamnose and mannose and overproduction of GMMA or outer membrane vesicles by arabinose. It will also incorporate the RDA and RDPS systems. These systems will not increase the virulence (by the introduction of these self-antigens) because most of the antigen genes are not highly expressed in vivo (106). The overexpression of antigen genes will also attenuate the strain (133, 134), as shown by overexpression of the flagellin gene (133, 135). The virulence of strains with or without chromosomal mutations for these antigen genes when carrying antigen gene expression plasmids can also be evaluated, as discussed further below. In case the expression plasmid increases the virulence high enough to cause disease, the strain or the plasmid can be modified to guarantee the attenuation attributes. Levels of gene expression can be modified up or down, as necessary, by switching the sugar regulated promoters, altering promoter and Shine-Dalgarno nucleotide sequence and the spacing between these elements and the start codon of the regulated gene.

Example 2: Materials and Methods

Bacterial strains, media and bacterial growth: Strain construction is performed in virulent S. Typhimurium strain χ3761 (75) and S. Enteritidis χ3550 (136). Different virulent wild-type *Salmonella* serovars, including S. Typhimurium χ3761 (B), S. Enteritidis χ3550 (D), S. Heidelberg χ3749 (B) (137), S. Choleraesuis χ3246 (C1) (138), S. Infantis χ3213 (C1) (139), S. Newport χ3240 (C2) (139), S. Dublin χ12323 (D) (140), are used for challenges. The $LD_{50}$s of most of these strains are between $10^3$ and $10^5$ in mice and chickens except that S. Heidelberg, S. Infantis and S. Newport do not often cause lethal disease in either mice or chickens. LB media or plates with appropriate supplements when needed are used for growth of *Salmonella* (141, 142).

Molecular and genetic procedures. Methods for DNA manipulations and PCR are standard (143). DNA sequence analysis is performed at the UFL DNA Sequence Laboratory while oligonucleotide and/or gene segment syntheses will be obtained commercially. Construction of deletions or deletion/insertions in *Salmonella* is performed using suicide vectors or P22 transduction (144-146).

Strain characterization. Vaccine strains are fully characterized at each step in their construction and before immunization studies for the presence of all phenotypes and genotypes. Genetic attributes are confirmed by PCR with appropriate probes and/or phenotype analyses. The fluorescent dye influx method is used to evaluate mutant membrane permeability. Strains are compared with vector control strains for stability of plasmid maintenance and antigen synthesis when strains are grown in the presence of arabinose or other sugars and/or DAP over a 50 generation period (147). LPS is checked by silver staining (148). Growth curves will be determined for each strain. Other experiments include determining OMP (147) and IROMPs profiles (149), OMV (80) and GMMA characterization (87, 150, 151), serum (152), bile and microbial peptides resistance (136), and attachment/invasion to epithelial INT-407 cells (153, 154). Each strain with antigen-specifying plasmid is evaluated for synthesis of the heterologous antigen by western blot.

Antigen preparation. Protective antigens, FliC, OmpC, OmpD, OmpF, SseB, and SseI, with C-terminal His-tag, are cloned into pBAD-His or pET vectors for synthesis in *E. coli* Top10 or BL21 and isolated by nickel chromatography (Sigma). Purified proteins are used for ELISA and ELISPOT assays and for preparing antiserum in New Zealand female rabbits. *Salmonella* LPS O-antigens are obtained commercially. S. Typhimurium outer membrane proteins (SOMPs) are purified from strain χ9424 that has been engineered to be unable to produce flagella, all in vitro-expressed pilus antigens, LPS O-antigen and several capsules. Other *Salmonella* OMPs are purified from correspondent 0-antigen mutants (147).

Statistics: The SAS program is used to do statistical tests and power analysis to evaluate animal numbers.

Example 3: Construction of Plasmids with Sugar-Regulated Synthesis of GFP to Enable Determination of Whether a Strain Unable to Metabolize a Sugar is Able to Take Up that Sugar to Enable Regulation of a Gene or Gene Sequence within that Strain FIG. 1 diagrams three plasmids pYA3700, pYA5351 and pG8R74 that possess the araC $P_{araBAD}$, rhaRS-$P_{rhaB}$ and xylR-$P_{xylA}$ cassettes, respectively, as sources of DNA encoding these cassettes to enable generation of suicide vectors with fusion of a selected regulatory cassette to a gene of choice in place of the promoter for that gene. These manipulations are described in Example 1 and strains with resulting deletion-insertion mutations with sugar regulated gene expression are described in the following examples.

The nucleotide sequence of the rhaRS-$P_{rhaB}$ cassette in pYA5351 is as follows:

(SEQ ID NO: 11)
```
GGGCGAATTCGAGCTCGGTACCCTCGAGGCTGAATTTCATTACGACCAGTCTAAA
AAGCGCCTGAATTCGCGACCTTCTCGTTACTGACAGGAAAATGGGCCATTGGCAA
CCAGGGAAAGATGAACGTGATGATGTTCACAATTTGCTGAATTGTGGTGATGTGA
TGCTCACCGCATTTCCTGAAAATTCACGCTGTATCTTGAAAAATCGACGTTTTTA
CGTGGTTTTCCGTCGAAAATTTAAGGTAAGAACCTGACCTCGTGATTACTATTTC
GCCGTGTTGACGACATCAGGAGGCCAGTATGACCGTATTACATAGTGTGGATTTT
TTTCCGTCTGGTAACGCGTCCGTGGCGATAGAACCCCGGCTCCCGCAGGCGGATT
TTCCTGAACATCATCATGATTTTCATGAAATTGTGATTGTCGAACATGGCACGGG
TATTCATGTGTTTAATGGGCAGCCCTATACCATCACCGGTGGCACGGTCTGTTTC
GTACGCGATCATGATCGGCATCTGTATGAACATACCGATAATCTGTGTCTGACCA
ATGTGCTGTATCGCTCGCCGGATCGATTTCAGTTTCTCGCCGGGCTGAATCAGTT
GCTGCCACAAGAGCTGGATGGGCAGTATCCGTCTCACTGGCGCGTTAACCACAG
CGTATTGCAGCAGGTGCGACAGCTGGTTGCACAGATGGAACAGCAGGAAGGGGA
AAATGATTTACCCTCGACCGCCAGTCGCGAGATCTTGTTTATGCAATTACTGCTCT
TGCTGCGTAAAAGCAGTTTGCAGGAGAACCTGGAAAACAGCGCATCACGTCTCA
ACTTGCTTCTGGCCTGGCTGGAGGACCATTTTGCCGATGAGGTGAATTGGGATGC
CGTGGCGGATCAATTTTCTCTTTCACTGCGTACGCTACATCGGCAGCTTAAGCAG
CAAACGGGACTGACGCCTCAGCGATACCTGAACCGCCTGCGACTGATGAAAGCC
CGACATCTGCTACGCCACAGCGAGGCCAGCGTTACTGACATCGCCTATCGCTGTG
GATTCAGCGACAGTAACCACTTTTCGACGCTTTTTCGCCGAGAGTTTAACTGGTC
ACCGCGTGATATTCGCCAGGGACGGGATGGCTTTCTGCAATAACGCGAATCTTCT
CAACGTATTTGTACGCCATATTGCGAATAATCAACTTCGTTCTCTGGCCGAGGTA
GCCACGGTGGCGCATCAGTTAAAACTTCTCAAAGATGATTTTTTTGCCAGCGACC
AGCAGGCAGTCGCTGTGGCTGACCGTTATCCGCAAGATGTCTTTGCTGAACATAC
ACATGATTTTTGTGAGCTGGTGATTGTCTGGCGCGGTAATGGCCTGCATGTACTC
AACGATCGCCCTTATCGCATTACCCGTGGCGATCTCTTTTACATTCATGCTGACGA
TAAACACTCCTACGCTTCCGTTAACGATCTGGTTTTGCAGAATATTATTTATTGCC
CGGAGCGTCTGAAGCTGAATCTTGACTGGCAGGGGGCGATTCCGGGATTTAACG
CCAGCGCAGGGCAACCACACTGGCGCTTAGGTAGCATGGGGATGGCGCAGGCGC
GGCAGGTTATCGGTCAGCTTGAGCATGAAAGTAGTCAGCATGTGCCGTTTGCTAA
CGAAATGGCTGAGTTGCTGTTCGGGCAGTTGGTGATGTTGCTGAATCGCCATCGT
TACACCAGTGATTCGTTGCCGCCAACATCCAGCGAAACGTTGCTGGATAAGCTGA
TTACCCGGCTGGCGGCTAGCCTGAAAAGTCCCTTTGCGCTGGATAAATTTTGTGA
```

-continued

```
TGAGGCATCGTGCAGTGAGCGCGTTTTGCGTCAGCAATTTCGCCAGCAGACTGGA

ATGACCATCAATCAATATCTGCGACAGGTCAGAGTGTGTCATGCGCAATATCTTC

TCCAGCATAGCCGCCTGTTAATCAGTGATATTTCGACCGAATGTGGCTTTGAAGA

TAGTAACTATTTTTCGGTGGTGTTTACCCGGGAAACCGGGATGACGCCCAGCCAG

TGGCGTCATCTCAATTCGCAGAAAGATTAATCTAGATAAATAAAAGCAGTTTACA

ACTCCTAGAATTGTGAATATATTATCACAATTCTAGGATAGAATAATAAAAGATC

TCTGCAGGCATGCAAGCTTGAGTATTCTATAGTGTCACCTAAATAGCTTGGCGTA

ATCATGGTCATAGCTGTTTCCTGTGTGAAATTGTTATCCGCTCACAATTCCACACA

ACATACGAGCCGGAAGCATAAAGTGTAAAGCCTGGGGTGCCTAATGAGTGAGCT

AACTCACATTAATTGCGTTGCGCTCACTGCCCGCTTTCCAGTCGGGAAACCTGTC

GTGCCAGCTGCATTAATGAATCGGCCAACGCGCGGGGAGAGGCGGTTTGCGTAT

TGGGCGCTCTTCCGCTTCCTCGCTCACTGACTCGCTGCGCTCGGTCGTTCGGCTGC

GGCGAGCGGTATCAGCTCACTCAAAGGCGGTAATACGGTTATCCACAGAATCAG

GGGATAACGCAGGAAAGAACATGTGAGCAAAAGGCCAGCAAAAGGCCAGGAAC

CGTAAAAAGGCCGCGTTGCTGGCGTTTTTCCATAGGCTCCGCCCCCCTGACGAGC

ATCACAAAAATCGACGCTCAAGTCAGAGGTGGCGAAACCCGACAGGACTATAAA

GATACCAGGCGTTTCCCCCTGGAAGCTCCCTCGTGCGCTCTCCTGTTCCGACCCT

GCCGCTTACCGGATACCTGTCCGCCTTTCTCCCTTCGGGAAGCGTGGCGCTTTCTC

ATAGCTCACGCTGTAGGTATCTCAGTTCGGTGTAGGTCGTTCGCTCCAAGCTGGG

CTGTGTGCACGAACCCCCCGTTCAGCCCGACCGCTGCGCCTTATCCGGTAACTAT

CGTCTTGAGTCCAACCCGGTAAGACACGACTTATCGCCACTGGCAGCAGCCACTG

GTAACAGGATTAGCAGAGCGAGGTATGTAGGCGGTGCTACAGAGTTCTTGAAGT

GGTGGCCTAACTACGGCTACACTAGAAGAACAGTATTTGGTATCTGCGCTCTGCT

GAAGCCAGTTACCTTCGGAAAAAGAGTTGGTAGCTCTTGATCCGGCAAACAAAC

CACCGCTGGTAGCGGTGGTTTTTTTGTTTGCAAGCAGCAGATTACGCGCAGAAAA

AAAGGATCTCAAGAAGATCCTTTGATCTTTTCTACGGGGTCTGACGCTCAGTGGA

ACGAAAACTCACGTTAAGGGATTTTGGTCATGAGATTATCAAAAAGGATCTTCAC

CTAGATCCTTTTAAATTAAAAATGAAGTTTTAAATCAATCTAAAGTATATATGAG

TAAACTTGGTCTGACAGTTACCAATGCTTAATCAGTGAGGCACCTATCTCAGCGA

TCTGTCTATTTCGTTCATCCATAGTTGCCTGACTCCCCGTCGTGTAGATAACTACG

ATACGGGAGGGCTTACCATCTGGCCCCAGTGCTGCAATGATACCGCGAGACCCA

CGCTCACCGGCTCCAGATTTATCAGCAATAAACCAGCCAGCCGGAAGGGCCGAG

CGCAGAAGTGGTCCTGCAACTTTATCCGCCTCCATCCAGTCTATTAATTGTTGCCG

GGAAGCTAGAGTAAGTAGTTCGCCAGTTAATAGTTTGCGCAACGTTGTTGCCATT

GCTACAGGCATCGTGGTGTCACGCTCGTCGTTTGGTATGGCTTCATTCAGCTCCG

GTTCCCAACGATCAAGGCGAGTTACATGATCCCCCATGTTGTGCAAAAAAGCGGT

TAGCTCCTTCGGTCCTCCGATCGTTGTCAGAAGTAAGTTGGCCGCAGTGTTATCA

CTCATGGTTATGGCAGCACTGCATAATTCTCTTACTGTCATGCCATCCGTAAGAT

GCTTTTCTGTGACTGGTGAGTACTCAACCAAGTCATTCTGAGAATAGTGTATGCG

GCGACCGAGTTGCTCTTGCCCGGCGTCAATACGGGATAATACCGCGCCACATAG
```

-continued

```
CAGAACTTTAAAAGTGCTCATCATTGGAAAACGTTCTTCGGGGCGAAAACTCTCA

AGGATCTTACCGCTGTTGAGATCCAGTTCGATGTAACCCACTCGTGCACCCAACT

GATCTTCAGCATCTTTTACTTTCACCAGCGTTTCTGGGTGAGCAAAAACAGGAAG

GCAAAATGCCGCAAAAAAGGGAATAAGGGCGACACGGAAATGTTGAATACTCAT

ACTCTTCCTTTTTCAATATTATTGAAGCATTTATCAGGGTTATTGTCTCATGAGCG

GATACATATTTGAATGTATTTAGAAAAATAAACAAATAGGGGTTCCGCGCACATT

TCCCCGAAAAGTGCCACCTGACGTCTAAGAAACCATTATTATCATGACATTAACC

TATAAAAATAGGCGTATCACGAGGCCCTTTCGTCTCGCGCGTTTCGGTGATGACG

GTGAAAACCTCTGACACATGCAGCTCCCGGAGACGGTCACAGCTTGTCTGTAAGC

GGATGCCGGGAGCAGACAAGCCCGTCAGGGCGCGTCAGCGGGTGTTGGCGGGTG

TCGGGGCTGGCTTAACTATGCGGCATCAGAGCAGATTGTACTGAGAGTGCACCAT

ATGCGGTGTGAAATACCGCACAGATGCGTAAGGAGAAAATACCGCATCAGGCGC

CATTCGCCATTCAGGCTGCGCAACTGTTGGGAAGGGCGATCGGTGCGGGCCTCTT

CGCTATTACGCCAGCTGGCGAAAGGGGATGTGCTGCAAGGCGATTAAGTTGGG

TAACGCCAGGGTTTTCCCAGTCACGACGTTGTAAAACGACGGCCAGTGAATTGTA

ATACGACTCACTATA.
```

The nucleotide sequence of the xylR-P$_{xylA}$ cassette in pG8R74 is as follows:

(SEQ ID NO: 12)
```
GGGCGAATTCGAGCTCGGTACCCTCGAGTCCATAATCAGGTAATGCCGCGGGTG

ATGGATGATGTCGTAATATTGGGCACTCCCTTTCAGTTGCTCAATTATGTTATTTC

ACACTGCTATTGAGATAATTCACAAGTGTGCGCTCGCTCGCAAAATAAAATGGA

ATGATGAAACTGGGTAATTCCGCTAGCttttgataaaaattttctcaaagccggttacgtattaccggttttgagt ttttgcatgattcagcaggaaaagaaccatgtttactaaacgtcaccgcatcacattactgttcaatgccaataaagcctatgaccggcag gtagtagaaggcgtaggggaatatttacaggcgtcacaatcggaatgggatattttcattgaagaagatttccgcgcccgcattgataaa atcaaggactggttaggagatggcgtcattgccgacttcgacgacaaacagatcgagcaagcgctggctgatgtcgacgtecccattg ttggggttggcggctcgtatcaccttgcagaaagttacccacccgttcattacattgccaccgataactatgcgctggttgaaagcgcatt tttgcatttaaaagagaaaggcgttaaccgctttgattttatggtatccggaatcaagcggcaaacgttgggccactgagcgcgaatat gcatttcgtcagcttgtcgccgaagaaaagtatcgcggagtggtttatcaggggttagaaaccgcgccagagaactggcaacacgcg caaaatcggctggcagactggctacaaacgctaccaccgcaaaccgggattattgccgttactgacgcccgagcgcggcatattctg caagtatgtgaacatctacatattcccgtaccggaaaaattatgcgtgattggcatcgataacgaagaactgacccgctatctgtcgcgt gtcgccctttcttcggtcgctcagggcgcgcggcaaatgggctatcaggcggcaaaactgttgcatcgattattagataaagaagaaat gccgctacagcgaattttggtcccaccagttcgcgtcattgaacggcgctcaacagattatcgctcgctgaccgatcccgccgttattca ggccatgcattacattcgtaatcacgcctgtaaagggattaaagtggatcaggtactggatgcggtegggatctcgcgctccaatcttga gaagcgttttaaagaagaggtgggtgaaaccatccatgccatgattcatgccgagaagctggagaaagcgcgcagtctgctgatttca accaccttgtcgatcaatgagatatcgcaaatgtgcggttatccatcgctgcaatatttctactctgttttaaaaaagcatatgacacga cgccaaaagagtatcgcgatgtaaatagcgaggtcatgttgtaatTCTAGAtaaataaaagcagtttacaactcctagaattgtgaatat attatcacaattctaggatagaataataaaagatctctgcagGCATGCAAGCTTGAGTATTCTATAGTGTCA

CCTAAATAGCTTGGCGTAATCATGGTCATAGCTGTTTCCTGTGTGAAATTGTTATC

CGCTCACAATTCCACACAACATACGAGCCGGAAGCATAAAGTGTAAAGCCTGGG
```

-continued

```
TGCCTAATGAGTGAGCTAACTCACATTAATTGCGTTGCGCTCACTGCCCGCTTTCC

AGTCGGGAAACCTGTCGTGCCAGCTGCATTAATGAATCGGCCAACGCGCGGGGA

GAGGCGGTTTGCGTATTGGGCGCTCTTCCGCTTCCTCGCTCACTGACTCGCTGC

GCTCGGTCGTTCGGCTGCGGCGAGCGGTATCAGCTCACTCAAAGGCGGTAATAC

GGTTATCCACAGAATCAGGGGATAACGCAGGAAAGAACATGTGAGCAAAAGGC

CAGCAAAAGGCCAGGAACCGTAAAAAGGCCGCGTTGCTGGCGTTTTTCCATAG

GCTCCGCCCCCTGACGAGCATCACAAAAATCGACGCTCAAGTCAGAGGTGGCG

AAACCCGACAGGACTATAAAGATACCAGGCGTTTCCCCCTGGAAGCTCCCTCGT

GCGCTCTCCTGTTCCGACCCTGCCGCTTACCGGATACCTGTCCGCCTTTCTCCCTT

CGGGAAGCGTGGCGCTTTCTCATAGCTCACGCTGTAGGTATCTCAGTTCGGTGTA

GGTCGTTCGCTCCAAGCTGGGCTGTGTGCACGAACCCCCCGTTCAGCCCGACCGC

TGCGCCTTATCCGGTAACTATCGTCTTGAGTCCAACCCGGTAAGACACGACTTAT

CGCCACTGGCAGCAGCCACTGGTAACAGGATTAGCAGAGCGAGGTATGTAGGCG

GTGCTACAGAGTTCTTGAAGTGGTGGCCTAACTACGGCTACACTAGAAGAACAG

TATTTGGTATCTGCGCTCTGCTGAAGCCAGTTACCTTCGGAAAAAGAGTTGGTAG

CTCTTGATCCGGCAAACAAACCACCGCTGGTAGCGGTGGTTTTTTTGTTTGCAAG

CAGCAGATTACGCGCAGAAAAAAAGGATCTCAAGAAGATCCTTTGATCTTTTCTA

CGGGGTCTGACGCTCAGTGGAACGAAAACTCACGTTAAGGGATTTTGGTCATGA

GATTATCAAAAAGGATCTTCACCTAGATCCTTTTAAATTAAAAATGAAGTTTTAA

ATCAATCTAAAGTATATATGAGTAAACTTGGTCTGACAGTTACCAATGCTTAATC

AGTGAGGCACCTATCTCAGCGATCTGTCTATTTCGTTCATCCATAGTTGCCTGACT

CCCCGTCGTGTAGATAACTACGATACGGGAGGGCTTACCATCTGGCCCCAGTGCT

GCAATGATACCGCGAGACCCACGCTCACCGGCTCCAGATTTATCAGCAATAAAC

CAGCCAGCCGGAAGGGCCGAGCGCAGAAGTGGTCCTGCAACTTTATCCGCCTCC

ATCCAGTCTATTAATTGTTGCCGGGAAGCTAGAGTAAGTAGTTCGCCAGTTAATA

GTTTGCGCAACGTTGTTGCCATTGCTACAGGCATCGTGGTGTCACGCTCGTCGTTT

GGTATGGCTTCATTCAGCTCCGGTTCCCAACGATCAAGGCGAGTTACATGATCCC

CCATGTTGTGCAAAAAAGCGGTTAGCTCCTTCGGTCCTCCGATCGTTGTCAGAAG

TAAGTTGGCCGCAGTGTTATCACTCATGGTTATGGCAGCACTGCATAATTCTCTT

ACTGTCATGCCATCCGTAAGATGCTTTTCTGTGACTGGTGAGTACTCAACCAAGT

CATTCTGAGAATAGTGTATGCGGCGACCGAGTTGCTCTTGCCCGGCGTCAATACG

GGATAATACCGCGCCACATAGCAGAACTTTAAAAGTGCTCATCATTGGAAAACG

TTCTTCGGGGCGAAAACTCTCAAGGATCTTACCGCTGTTGAGATCCAGTTCGATG

TAACCCACTCGTGCACCCAACTGATCTTCAGCATCTTTTACTTTCACCAGCGTTTC

TGGGTGAGCAAAAACAGGAAGGCAAAATGCCGCAAAAAAGGGAATAAGGGCGA

CACGGAAATGTTGAATACTCATACTCTTCCTTTTTCAATATTATTGAAGCATTTAT

CAGGGTTATTGTCTCATGAGCGGATACATATTTGAATGTATTTAGAAAAATAAAC

AAATAGGGGTTCCGCGCACATTTCCCCGAAAAGTGCCACCTGACGTCTAAGAAA

CCATTATTATCATGACATTAACCTATAAAAATAGGCGTATCACGAGGCCCTTTCG

TCTCGCGCGTTTCGGTGATGACGGTGAAAACCTCTGACACATGCAGCTCCCGGAG

ACGGTCACAGCTTGTCTGTAAGCGGATGCCGGGAGCAGACAAGCCCGTCAGGGC
```

```
GCGTCAGCGGGTGTTGGCGGGTGTCGGGGCTGGCTTAACTATGCGGCATCAGAG

CAGATTGTACTGAGAGTGCACCATATGCGGTGTGAAATACCGCACAGATGCGTA

AGGAGAAAATACCGCATCAGGCGCCATTCGCCATTCAGGCTGCGCAACTGTTGG

GAAGGGCGATCGGTGCGGGCCTCTTCGCTATTACGCCAGCTGGCGAAAGGGGGA

TGTGCTGCAAGGCGATTAAGTTGGGTAACGCCAGGGTTTTCCCAGTCACGACGTT

GTAAAACGACGGCCAGTGAATTGTAATACGACTCACTATA
```

Figure 2:
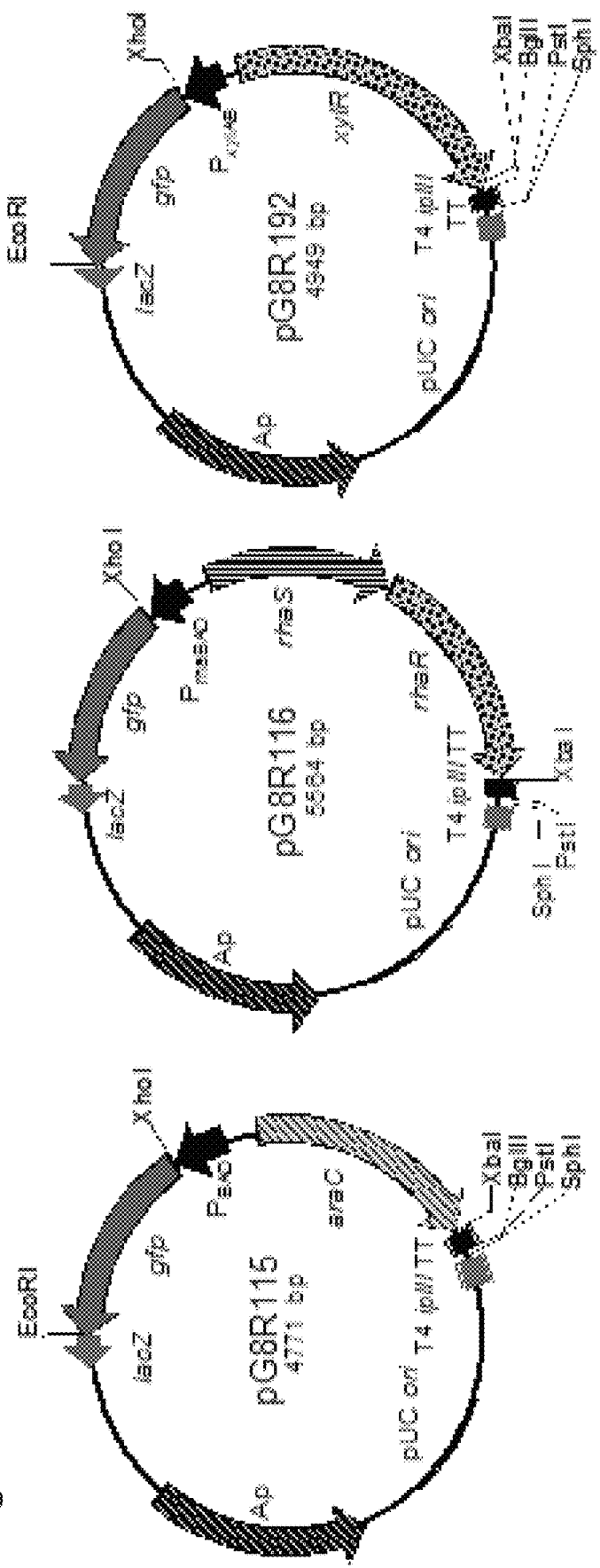
FIG. 2 depicts three plasmids in which GFP synthesis is regulated by three different sugars.

FIG. 2 depicts the plasmids pG8R115, pG8R116 and pG8R192 that cause synthesis of GFP to be dependent on the presence of arabinose, rhamnose or xylose, respectively. These plasmids can be electroporated into any strain of multiple bacterial species by selection for ampicillin resistance and then screened for synthesis of GFP in the presence of the sugar of interest and the cessation of GFP synthesis in the absence of the sugar. If GFP synthesis is observed, then it is possible to construct mutant strains in which a promoter for a gene of interest has been deleted and replaced by a araC $P_{araBAD}$, rhaRS-$P_{rhaB}$ or xylR-$P_{xylA}$ cassette so that gene expression is now dependent on the presence of arabinose or rhamnose or xylose, respectively. It should be noted that this capability is very useful when the bacterial strain or species of interest is unable to metabolize or grow on arabinose, rhamnose or xylose such that is unknown whether these sugars can be transported into the bacterial cells that would be necessary is one is to use the presence of that sugar for the expression of genes in that bacterial strain or species.

Figure 3A:
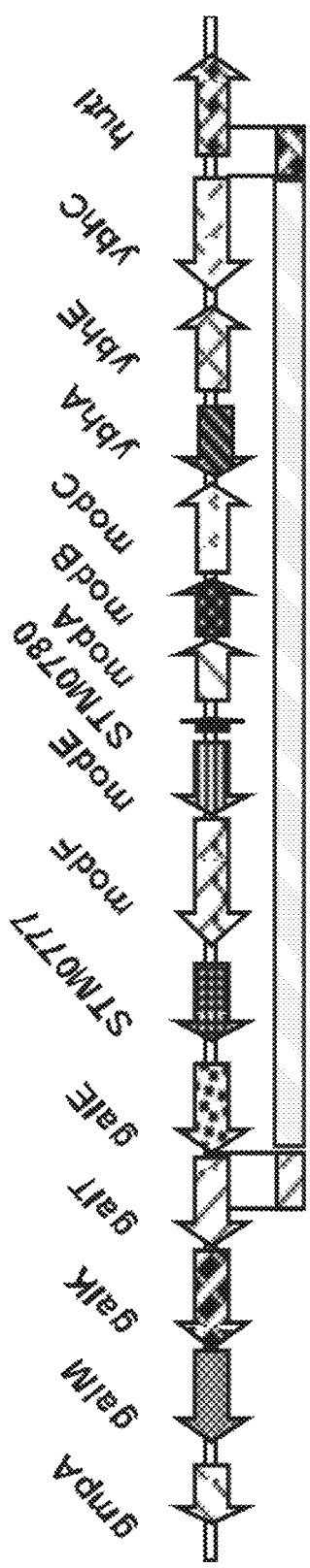
Figure 3B:
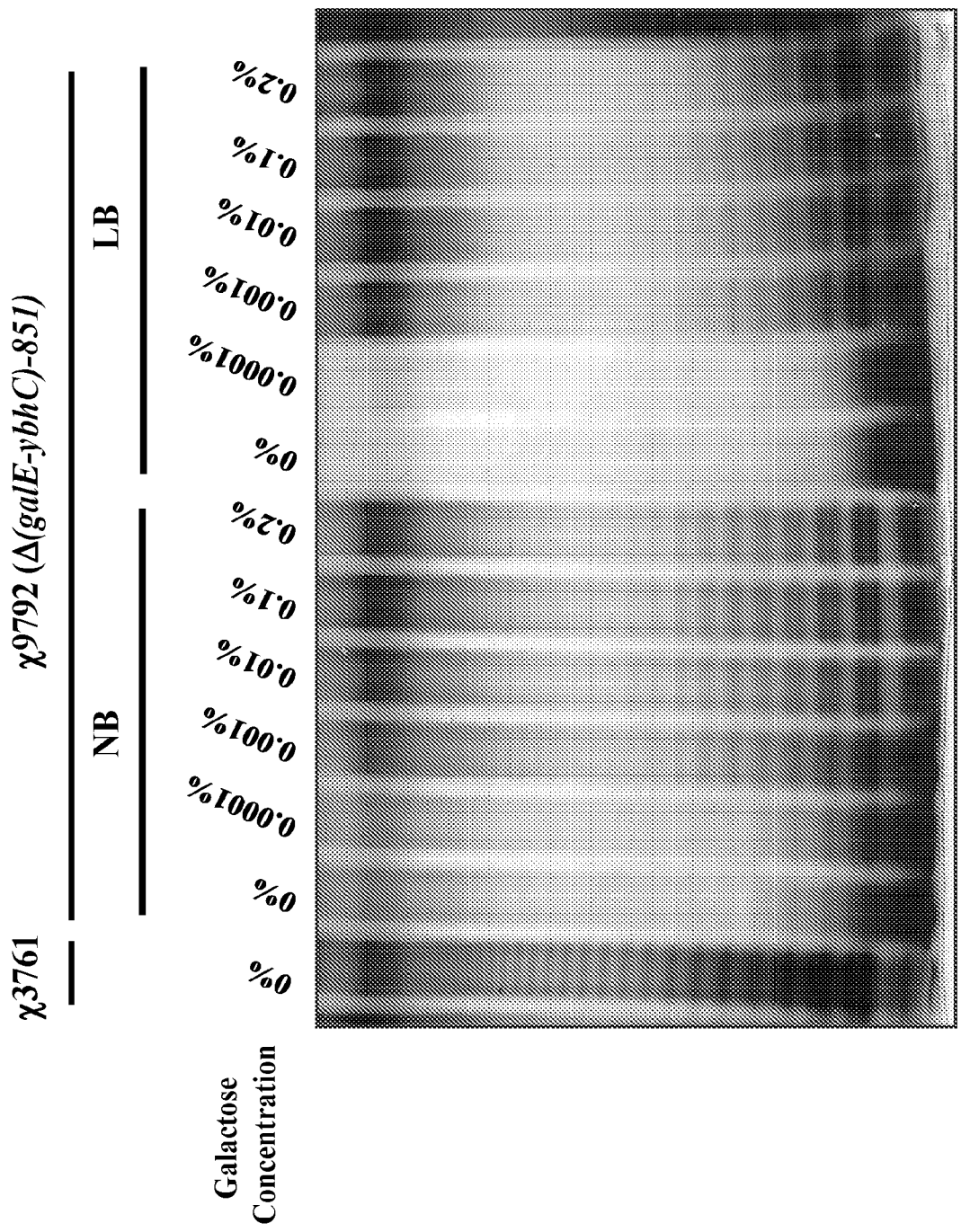

Example 4: Isolation and Characterization of Strains with galE Mutations to Enable Functional Reversible Synthesis of LPS Dependent on Presence of Free Galactose. Construction of Vaccine Vector Strains with galE Mutations to Enable Regulated Synthesis of UDP-Gal Needed for Synthesis of LPS O-Antigen Side Chains and the LPS Outer Core and Enable Growth in Presence of Galactose without Toxicity and Potential Selection of Galactose-Resistant Variants to Reduce Immunogenicity The gene galE encodes UDP-galactose 4-epimerase, which interconverts UDP-galactose and UDP-glucose. As a part of galactose catabolism, galE was related to both galactose synthesis and degradation. All surface liposolysaccharide (LPS) of *Salmonella* species contain galactose units, in the LPS core and in the LPS O-antigen side chain. Since UDP-galactose is the precursor of the galactose units in LPS, the galE mutant synthesizes core-defective or "rough" LPS unless exogenous galactose is provided (47). The galE mutant of S. Typhimurium is avirulent and confers protection against virulent S. Typhimurium challenge in mice (47, 50, 155). Some of the galE mutants of S. Choleraesius are also avirulent (156, 157). The only licensed live attenuation bacterial vaccine approved for human use is S. Typhi Ty21a with a galE mutation as well as other mutations (30, 158, 159). S. Typhi Ty21a was only partially attenuated and confers moderate protective immunity against typhoid in human field trials (30, 47, 160-163).

However, a single galE mutation in S. Typhi still enables virulence for humans and only provides moderate protection against typhoid (30, 47, 161, 163, 164) as also observed with the galE mutants of S. Choleraesuis (165). Besides, *Salmonella* galE mutants are sensitive to galactose to induce lysis in vitro (48, 166, 167). Even a defined deletion of galE in S. Typhimurium confers sensitivity to galactose-induced lysis, which is an undesirable attribute to the vaccine. Licensed strain Ty21a has this unfavored attribute too. galE mutants lack the enzyme UDP galactose 4-epimerase but keep the ability to take up galactose from exogenous sources through galactose transporters (168, 169). When grown in the presence of galactose, the galactokinase and galactose-1-phosphate uridyltransferase, encoded by genes galK and galT, respectively, can synthesize UDP-galactose from galactose via galactose-1-phosphate and lead to cell growth arrest and even lysis. The exact lytic mechanism is unknown, but death is correlated to the growth and intracellular accumulation of galactose metabolites, especially the accumulation of galactose 1-phosphate and UDP-galactose due to galactokinase activity (30, 48). The accumulation of UDP-D-galactose leads to the growth arrested due to low availability of CTP and UTP, which results in reduced RNA synthesis (49). The galE mutants grow poorly and their viability are significantly reduced by lyophilization (50). The avirulence of galE mutants is chiefly due to the incomplete cell wall lipopolysaccharide and to galactose-induced bacterial cell lysis (30). It will select for galactose-resistance and $Gal^+$ phenotype (170). The lysis can happen at galactose concentrations as low as 0.002% (166). Galactose-induced lysis occurs in strain Ty21a in vitro at >6 mM galactose (30, 47) whereas Ty2 with a defined galE mutation is even more sensitive to >0.06 mM galactose (50, 163). Growth of galE mutants in the presence of galactose also selects for galactose-resistant strains that lose the ability to show the reversible rough to smooth variation dependent on supply of galactose (170). Glucose can protect galactose-sensitive galE strains from lysing by catabolite repression to the extent that lysis levels of galactose intermediates cannot accumulate (167, 171). Lowering the galactokinase activity may also give the strain resistance to galactose (48, 166, 167). Thus, to conquer this problem and extend the usage of galE mutations conferring a reversible rough-smooth variation that serves as a means for regulated delayed attenuation for vaccines, we constructed a strain with a new galE mutation with increased resistance to galactose and yet displaying the regulated attenuation dependent of the presence of added galactose, which is unavailable in vivo. We then evaluated the inclusion of this mutation in S. Typhimurium vaccine strains.

Three strains with different galE mutations were generated. Strain χ4094 has a galactose sensitive galE496 mutation, as seen with most galE mutants. Strain χ4700 has an uncharacterized deletion mutation Δ(galE-uvrB)-1005 which enables strains to be insensitive to galactose. Strain χ9792 has a galactose insensitive Δ(galE-ybhC)-851 mutation, which deletes 11 gene sequences from galE to ybhC (FIG. 3A). The strain requires 0.0010% galactose in growth media to form complex LPS O-antigen (FIG. 3B) in either Nutrient broth or LB broth.

To determine whether addition of galactose affects the growth of *Salmonella* strains with different galE mutations, growth experiments were performed. The first experiment evaluated the final ODs of overnight cultures with varying galactose concentrations in LB broth or NB broth. It should be noted that NB broth is devoid of all sugars such that there can be no interference in results due to trace amounts of galactose. In LB media, the ODs of the overnight culture of χ4094 is 1.088 with 0.0010% galactose, but drops to 0.159 with 0.01% galactose. The ODs of χ4700 and χ9792 were not significantly affected by varying concentrations of galactose. Similar trends were observed when galE mutants were grown in NB broth with varying galactose concentrations (FIG. 3C). Overall the data confirms χ9792 (Δ(galE-ybhC)-851)) is not as sensitive to galactose as χ4094.

A second experiment evaluated growth of the strains during a 7-hour period in growth media with varying galactose concentrations (FIGS. 4A-4H). An overnight culture of each strain was grown in NB broth without galactose. A subculture was made by dilution at 1:100 into prewarmed 3 ml NB broth with varying percent concentrations of galactose (0, 0.001, 0.01, 0.02, 0.05, 0.1, 0.2, 0.5). The cultures were incubated at 37° C. with shaking. Optical densities were measured and recorded every 1 hour. Without galactose, all strains grows similarly. Strain χ4094 has the galactose sensitive galE496 mutation. Strain χ4700 has the galactose insensitive Δ(galE-uvrB)-1005 mutation. Strain χ9792 has the galactose insensitive Δ(galE-ybhC)-851 mutation. Strain χ11015 has the galactose insensitive Δ(galE-ybhC)-851 ΔgalP211 mutation. Strain χ11141 has the galactose insensitive Δ(galE-ybhC)-851 ΔgalP211 ΔmglBAC mutation. FIGS. 4A-4H showed that mutations ΔgalP211 and ΔmglBAC help the strain reach higher ODs.

Figure 4A:
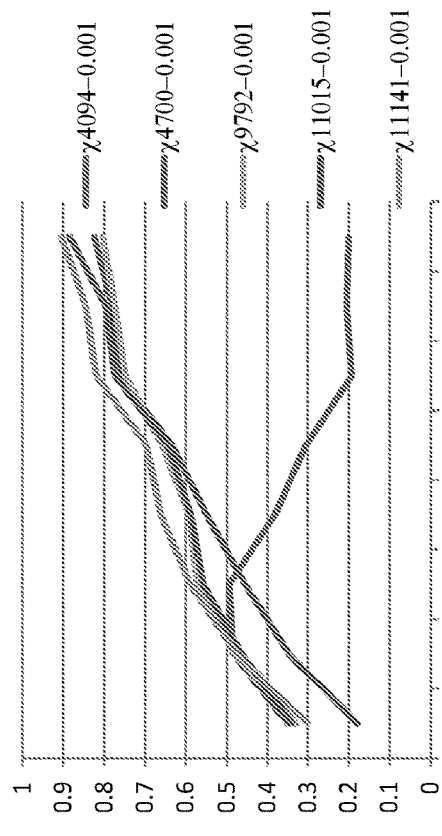
Figure 4B:
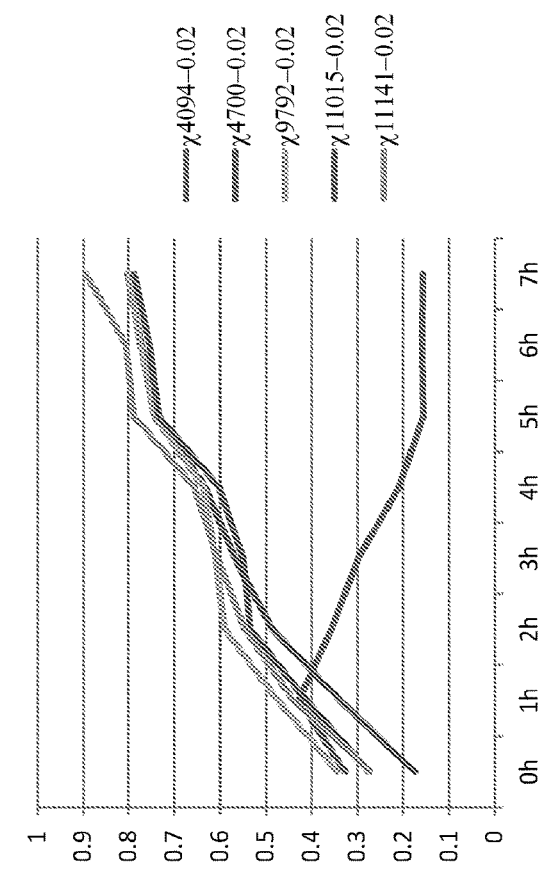
Figure 4C:
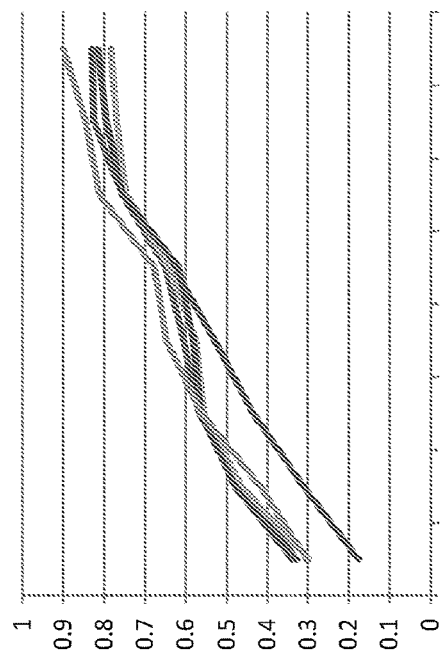
Figure 4D:
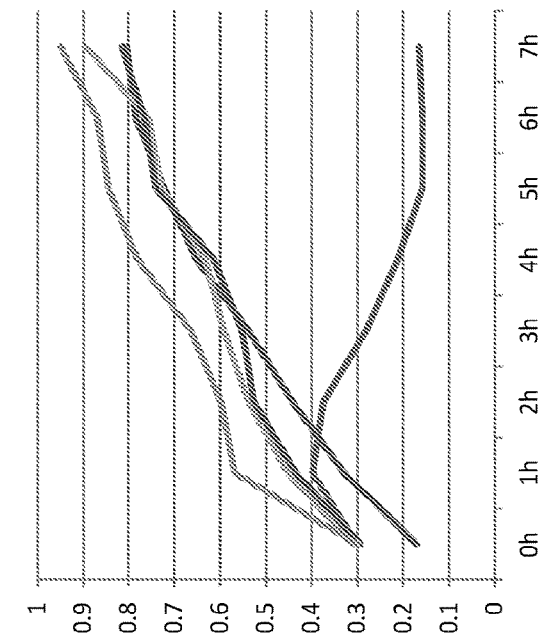
Figure 5:
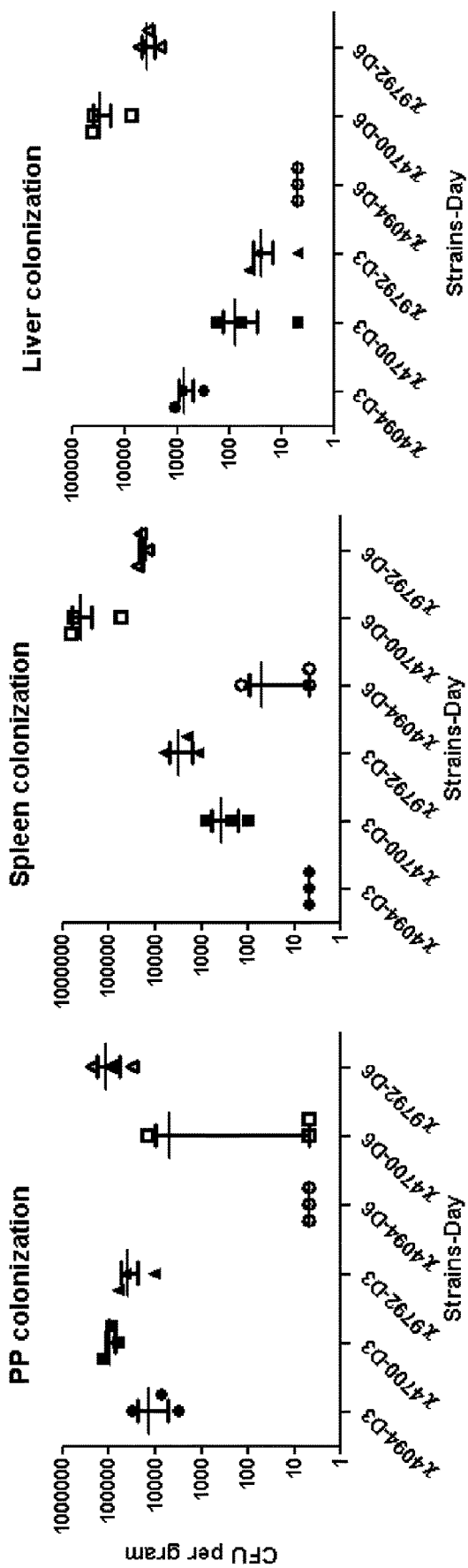
FIG. 5 depicts the colonization of galE mutants.
Figure 6C:
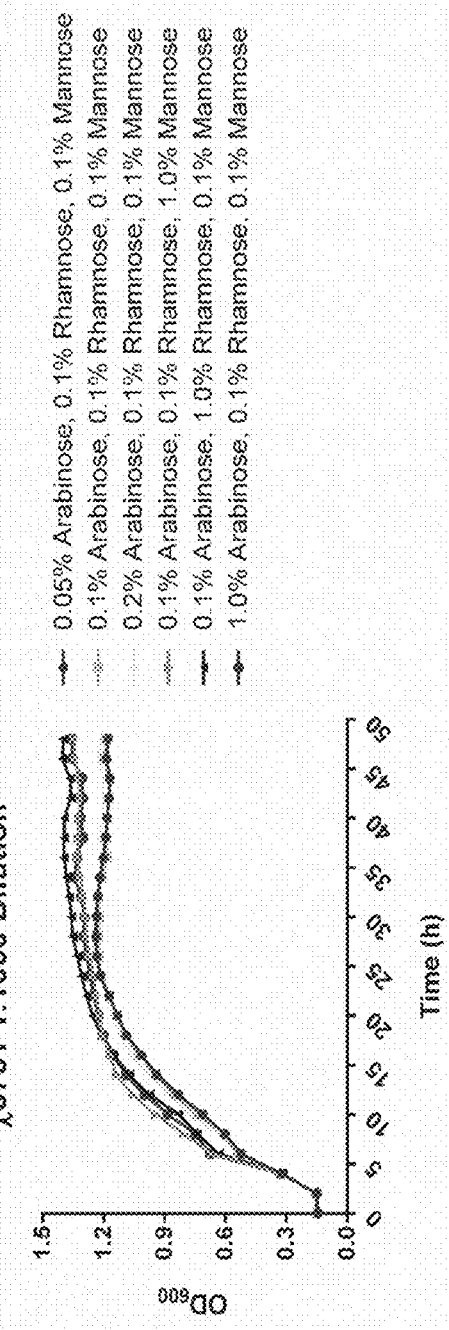
Figure 6D:
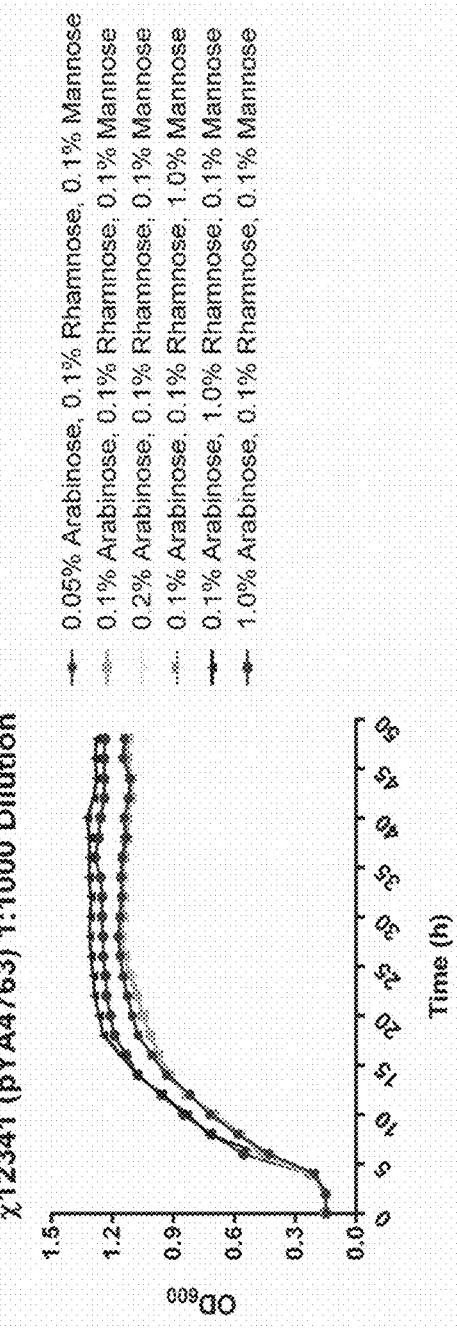
Figure 6E:
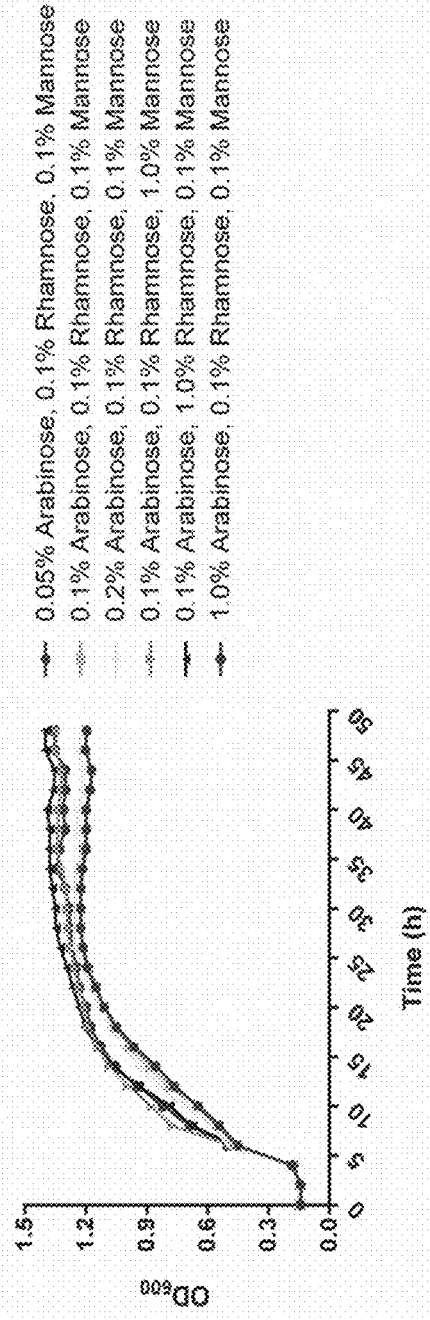
Figure 6F:
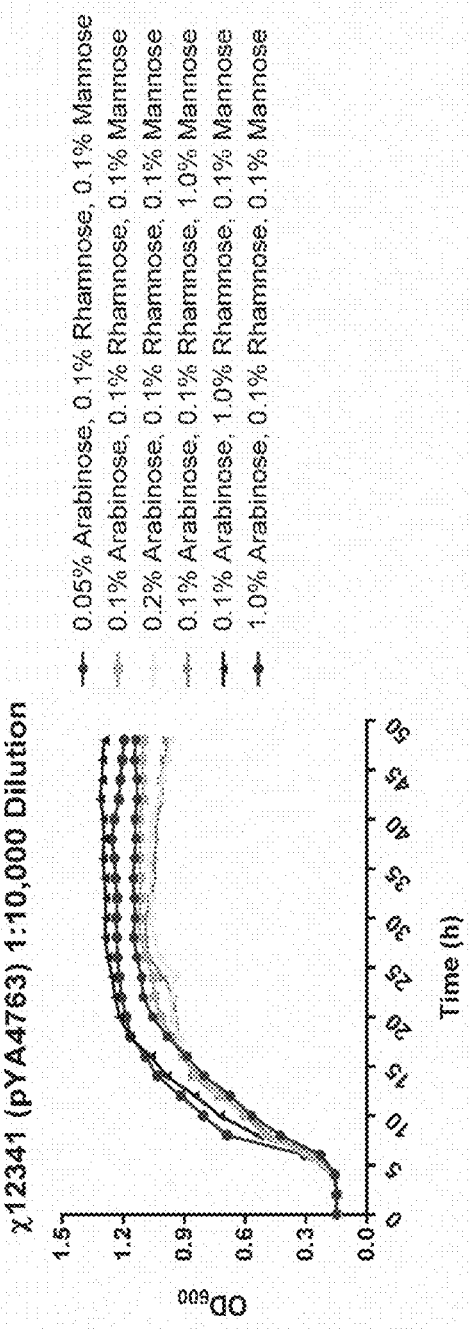
Figure 6I:
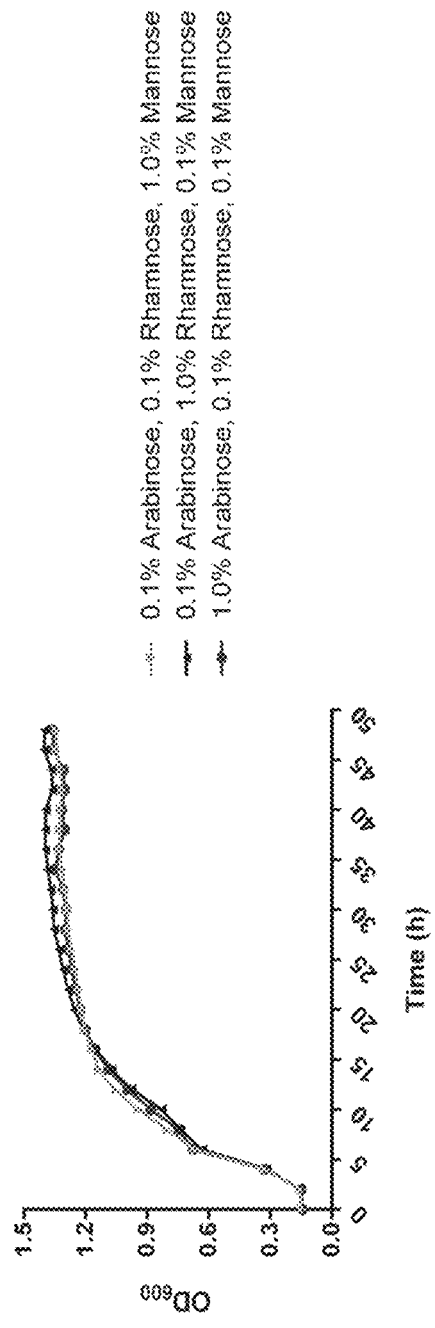
Figure 6J:
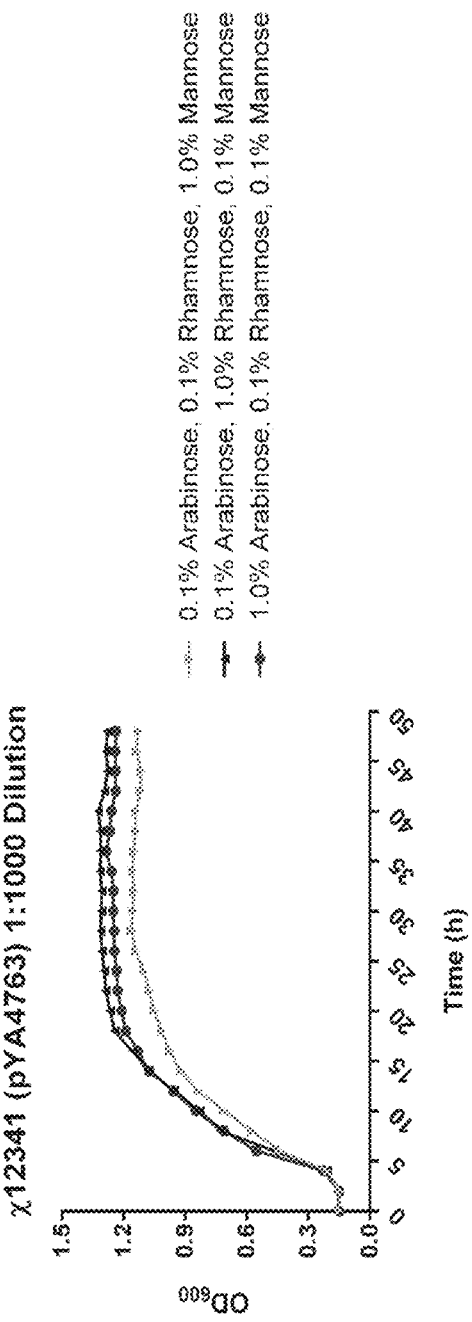
Figure 6K:
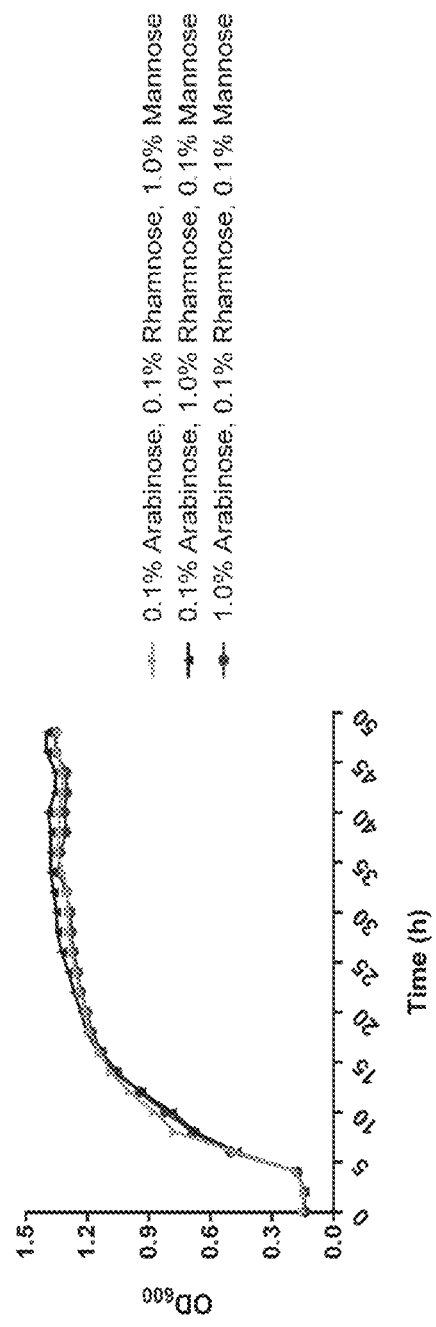
Figure 6L:
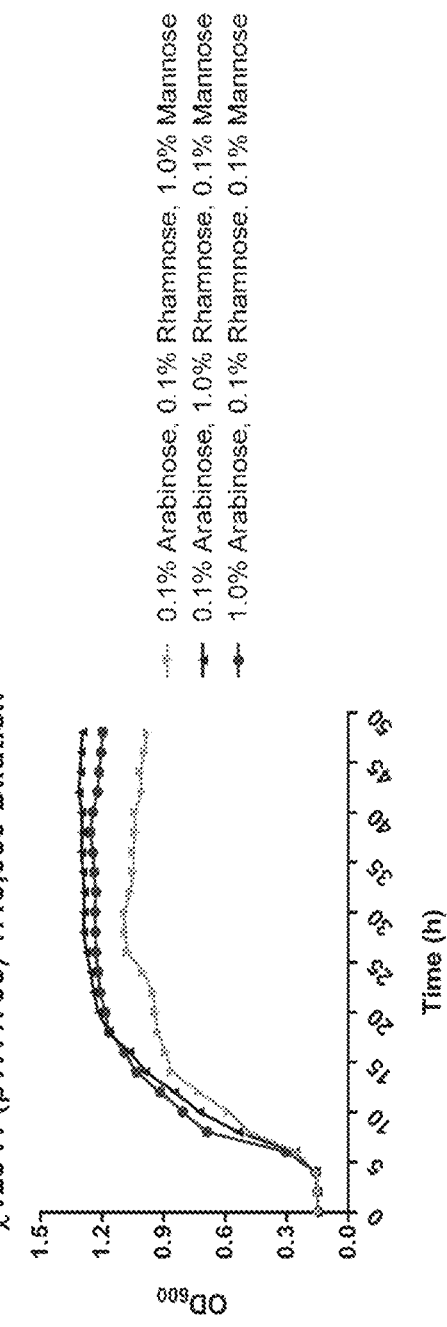
Figure 6M:
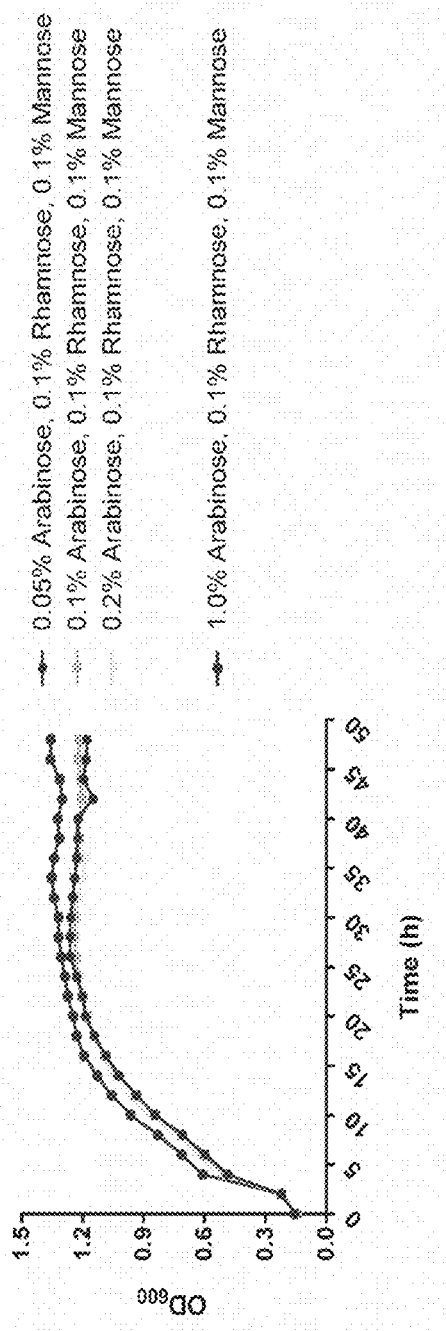
Figure 6N:
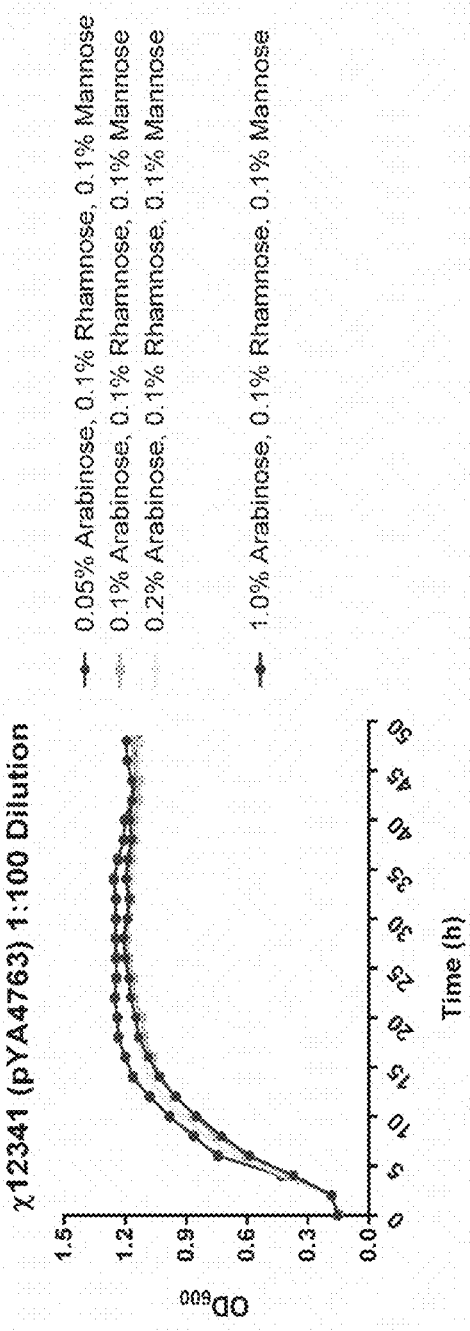
Figure 6O:
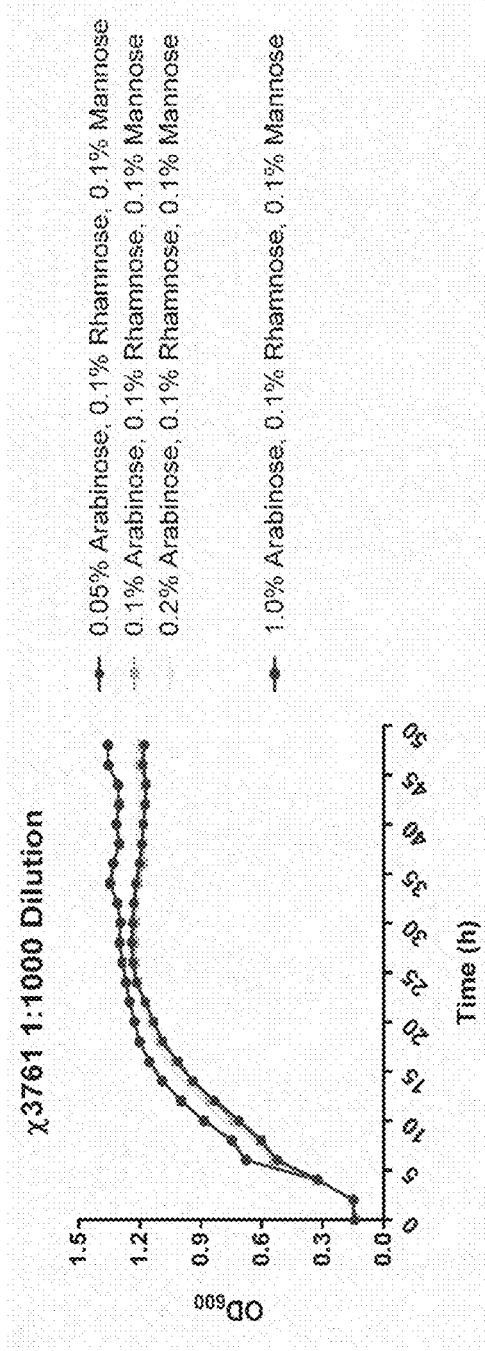
Figure 6P:
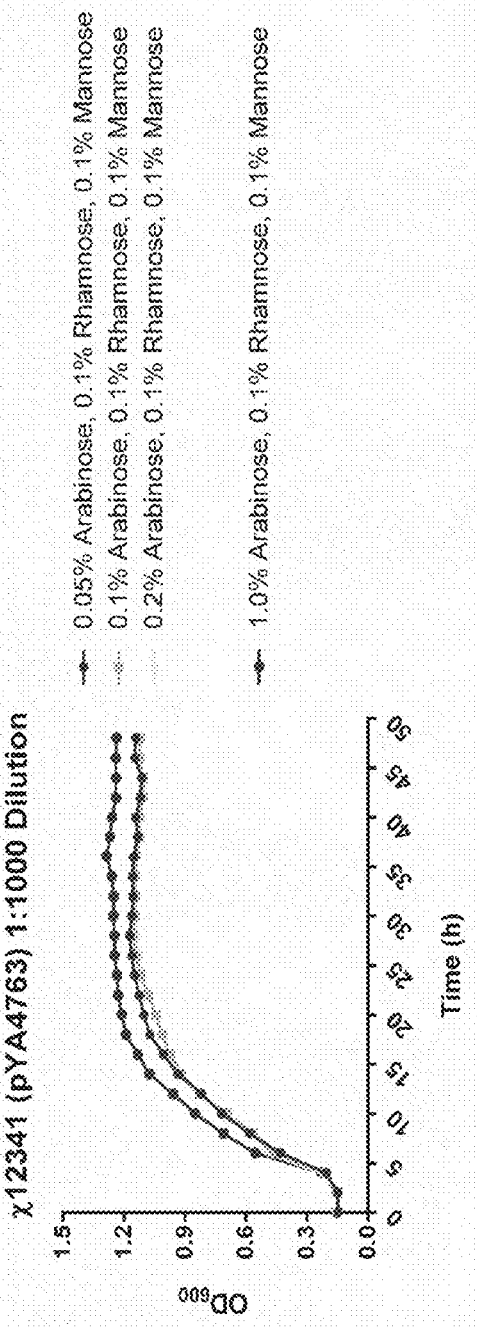

As shown in FIG. 4B, strain χ4094 grows for 2 hours and then starts to lyse even with 0.001% galactose. With the increasing galactose concentrations, the starting time for lysis was reduced. Both strains χ4700 and χ9792 can tolerate galactose as high as 0.5% without compromising growth (see FIGS. 4A-4H). These results demonstrate that high concentrations of galactose do not inhibit the growth and colonization of a strain with the Δ(galE-ybhC) mutation. The improved galactose tolerance enables the strain to display higher tissue colonization than the strain with the sensitive galE496 mutation at day 6 (FIG. 5) following oral inoculation of mice. The data confirms that the Δ(galE-ybhC)-851 mutation can be used in vaccine strains to enable a reversible rough-smooth phenotype dependent of the presence of galactose in the growth medium and will confer an additional means of regulated delayed attenuation in vivo since free non-phosphorylated galactose is not present in animal tissues.

Example 5: Construction and Evaluation of Group B RASV S. Typhimurium Strains with Rhamnose-Regulated Delayed O-Antigen Synthesis, Mannose-Regulated 0-Antigen Side Chain Synthesis and Arabinose-Regulated Production of GMMA, or Outer Membrane Vesicles, Synthesizing Protective Antigens In Vivo O-antigen ligase WaaL is necessary to ligate polysaccharide to the lipid A-core moiety. Mutation of waaL results in an intact core with no O-antigen attached to it (172, 173). We deleted the waaL in the operon and put the rhamnose regulated waaL ($\Delta P_{rhaBAD}$ waaL) in the pagL gene since the pagL mutation does not impair *Salmonella* virulence (174). Rhamnose will replace arabinose to achieve down-regulation of O-antigen synthesis in vivo because a relatively high concentration of rhamnose is necessary to activate this promoter (175). RASV strains with rhamnose-regulated waaL will synthesis normal LPS in the presence of rhamnose in vitro, but form rough LPS due to the absence of O-antigen ligase in vivo. This strategy exposes the conserved LPS core oligosaccharide and enhance production of conserved OMPs, including porins (176, 177), result in more effective presentation of conserved OMPs to the host immune system for enhancing immunogenicity and aid in production of a cross-protective immune response against heterologous bacteria (173).

The mutant strain is attenuated to $10^9$ CFU and provides protection against both S. Typhimurium and S. Enteritidis challenge at $10^9$ CFU (Table 1). However, this mutation is not fully attenuated as it still causes death at $10^9$. Therefore, a Δpmi mutation is also included as double shutoff of O-antigen synthesis in strain χ12339. RASVs with $\Delta P_{rhaBAD}$ waaL and Δpmi mutations need both rhamnose and mannose to form complete 0-antigen. To further increase the protection, a $\Delta P_{fur}$ mutation is included to up-regulate IROMPs in vivo to enhance the induction of cross-protective immunity to enteric pathogens as was done in strain χ12362.

TABLE 1

Oral immunization of BALB/c mice (6-8 weeks) with strain χ12337 (ΔwaaL ΔpagL:: TT rhaSR $P_{rhaBAD}$ waaL) and with survivors challenged orally with $10^9$ wild-type *S. Typhimurium* χ3761[a] and *S. Enteritidis* χ3550[b] 30 days later.

| | Immunization data | | Challenge data |
|---|---|---|---|
| Bacterial strain for immunization | Dose (CFU) | No. of survivors/ total no. of mice | No. of survivors/ total no. of mice |
| S. Typhimurium χ12337 | 1.46 × $10^9$ | 4/5 | 4/4[a] |
| | 1.64 × $10^5$ | 5/5 | 4/5[a] |
| | 1.46-1.64 × $10^8$ | 10/10 | 10/10[b] |
| | 1.64 × $10^6$ | 5/5 | 3/5[b] |
| | 1.64 × $10^6$ | 5/5 | 3/5[b] |

* Strain was grown in LB broth with 0.1% rhamnose.

All mutations are dedicated to increase the presentation of conserved proteins to aid in the induction of cross-protective immunity and achieve regulated delayed attenuation. As a tolR mutation can increase GMMA or outer membrane vesicles production (100, 101), candidate RASVs have been further modified by introduction of an arabinose-regulated tolR mutation ($\Delta P_{tolR}$::TT araC $P_{araBAD}$ tolR, simplified as $\Delta P_{tolR}$ thereafter) to further up-regulate GMMA or outer membrane vesicles in vivo to maximally induce antibodies cross-reactive to the OMPs of other *Salmonella* serovars. Furthermore, plasmids encoding protective antigens will be introduced in the vaccine strains to evaluate protective immunity. Since candidate antigen genes are either repressed or expressed at low levels in vivo (106), overproduction of these antigens will facilitate their presentation (106, 108).

The final strain will need arabinose, mannose and rhamnose to behave as wild-type and achieve attenuation in vivo gradually (Table 2). Rhamnose- and mannose-regulated genes will lose their function first, to expose surface antigens, and then arabinose-regulated genes shut off will increase GMMA or outer membrane vesicles.

TABLE 2

| Phenotypes associated with key mutations in RASV strains | |
|---|---|
| Mutation | Phenotype |
| ΔwaaL/ΔpagL:: TT rhaSR $P_{BAD}$ waaL | Deletion of the O-antigen ligase gene waaL, insertion of rhamnose-regulated waal to pagL gene position and deletion of the pagL gene, enable the synthesis of WaaL dependent on the presence of rhamnose in growth medium for normal LPS as wild type in vitro and ceases to be synthesized in vivo due to the absence of rhamnose, resulting in incomplete O-antigen synthesis and attenuation. |
| Δpmi | Deletion of phosphomannose isomerase gene to convert fructose to mannose necessary for synthesis of LPS O-antigen side chains. LPS O-antigen can be synthesized during in vitro growth by exogenous mannose in the growth medium for exhibiting nearly wild-type attributes for survival and colonization of lymphoid tissues at the time of immunization and lost after five to ten cell divisions in vivo and become avirulent due to inability to synthesize the LPS O-antigen side chains for the absence of free non-phosphorylated mannose and also become sensitive to complement-mediated cytotoxicity and susceptible to phagocytosis by macrophages. |
| $\Delta P_{fur}$:: TT araC $P_{BAD}$ fur | The fur gene encodes a repressor that represses all genes involved in iron acquisition in presence of free iron. When iron concentrations become low, as in animal host tissues beyond the intestinal wall barrier, the Fur ceases to be synthesized and constitutive synthesis of IROMPs commences. This mutation enables turn on the fur gene with arabinose in vitro and turn off in the absence of arabinose in vivo for overexpression of IROMPs in vivo and leads to attenuation. |
| $\Delta P_{tolR}$:: TT araC $P_{BAD}$ tolR | The deletion-insertion mutation eliminates TolR synthesis and up-regulate GMMA or outer membrane vesicles production in vivo due to the absence of arabinose. |
| ΔrelA:: araC $P_{BAD}$ lacI TT | The deletion-insertion mutation eliminates RelA which governs synthesis of ppGpp and couples growth to protein synthesis. The araC $P_{BAD}$ lacI insertion causes an arabinose-dependent synthesis of the LacI repressor in vitro, which governs the express of genes encoding protective protein antigens encoded on plasmids, and enable antigen production in vivo due to depletion of LacI in vivo. |
| ΔasdA | For balanced-lethal system and maintains complete sensitivity of RASV to all antibiotics. |
| Δ(wza-wcaM) | Eliminates twenty enzymes needed to synthesize several exopolysaccharides that promote biofilm formation and synthesis of GDP-fucose required for colanic acid synthesis (178), which protects cells undergoing cell wall-less death from lysing (179) |
| Δ(galE-ybhC) | Deletion of UDP-glucose 4-epimerase gene to interconvert UDP-galactose and UDP-glucose necessary for synthesis of LPS O-antigen core. LPS O-antigen can be synthesized during in vitro growth by exogenous galactose in the growth medium for exhibiting nearly wild-type attributes for survival and colonization of lymphoid tissues at the time of immunization and lost after several cell divisions in vivo and become avirulent due to inability to synthesize the LPS O-antigen core due to the absence of free non-phosphorylated galactose and also become sensitive to complement-mediated cytotoxicity and susceptible to phagocytosis by macrophages. Mutants with this mutation can tolerate high concentration of galactose to 0.5% |

Note:
Δ = Deletion of genetic sequence;
P = Promoter for RNA polymerase recognition and binding;
:: = insertion of DNA or gene sequence;
TT = Transcription terminator.

Strain construction. Strain χ12470 is generated by using Strain χ12337 and subsequently adding mutations Δpmi, ΔP$_{fur}$ and ΔP$_{tolR}$ sequentially (Table 2). Mutations ΔrelA::araC P$_{araBAD}$ lacI TT (ΔrelA) for RDPS (180), ΔasdA for the balanced-lethal system, and Δ(wza-wcaM) to eliminate synthesis of exopolysaccharides (Table 2) are introduced result in strain χ12465 to facilitate its use as a vector. A ΔP$_{tolR}$ mutation—is added to generate strain χ12473. After confirmation of final strain by phenotypic and PCR analysis, Asd$^+$ plasmids carrying an individual antigen gene are introduced into the strain. The corresponding antigen gene will be deleted using a suicide vector (144, 181) from the chromosome to prevent potential recombination between genes on the chromosome and plasmid. Membrane integrity, OMVs production (101), presence and stability of all phenotypic traits of strains are thoroughly investigated. The sugar regulated promoters or SD or start codon may be switched to regulate the production of O-antigen ligase, Fur, TolR in vitro to balance the immunogenicity and attenuation (75).

Plasmid construction. Since all the antigens are surface exposed or secreted, natural gene sequences are expressed using the balanced-lethal Asd$^+$ vector pYA3342 (P$_{trc}$, pBR ori) (147). The presence of RDPS will repress the antigen gene expression in vitro by arabinose, but up-regulate in vivo (180). A shift to a low copy plasmid pYA3337 (P$_{trc}$, pSC101 ori) (182) or pYA3332 (P$_{trc}$, p15A ori) (183) is performed if overproduction leads to a metabolic burden as indicted by significantly slower growth.

All the genes except fliC are used according to their natural sequence. A truncated FliC180, which deletes the 180 amino acids encoding the antigenically variable serovar-specific hypervariable domain of the flagellin antigen, is used to reduce the induction of antibody titers to serovar-specific antigens and increase the cross protection against conserved domain of flagellin. The FliC180 protein retains the conserved N- and C-terminal regions that interact with TLR5 to recruit/stimulate innate immune responses (184, 185) and the CD4-dependent T-cell epitopes (186). The individual antigen is tested first, followed by testing of multiple antigens using plasmid encoding several antigens as an operon (183, 187, 188) or with multiple genes that are independently regulated (189-193). The recF mutation will be incorporated to reduce recombination between antigens on plasmid (194).

In vitro evaluation of RASVs expressing protective antigen genes. The ability of the RASV strains to synthesize and secrete protective antigen is analyzed by conducting cell fractionation studies to determine the amount of antigen present in the cytoplasm, periplasm and supernatant fractions by western blot. Strains are grown in Luria Broth (LB) to an OD$_{600}$ of 0.8 at 37° C. and centrifuged. The supernatant fluid is saved for analysis of secreted proteins. Periplasmic and cytoplasmic fractions are prepared by a lysozyme-osmotic shock method (147, 195, 196). Equal volumes of periplasmic, cytoplasmic and supernatant fractions and total lysate samples are analyzed via western blots probed with correspondent antibody. Tissue culture experiments are performed to evaluate antigen translocation into mouse macrophage-like cell lines, J774.A and/or P388D1 by western blots and immunofluorescence (197-199).

Animal experiments. BALB/c female mice, six to eight weeks of age, are used and housed in BSL2 containment with filter bonnet covered cages. Typical experiments include groups of fifteen mice for challenge (repeat once) (200). Additional mice are used to determine colonization and for harvesting spleens for immunological analyses. Colonization and immunogenicity is evaluated for all constructions synthesizing Salmonella conserved protective antigens.

Mice are immunized orally on day 0 with a dose of ~ 10$^9$ CFU RASVs, boosted with the same dose 1 week after, and orally challenged at week 4 with 100×LD$_{50}$ virulent Salmonella strain according to standard procedures (200). LD$_{50}$s of wild type strains are known or are evaluated. Morbidity and mortality are recorded daily. First, strains carrying each individual antigen with PBS control against S. enteritidis challenge are compared. If protection is observed in this test, subsequent studies are done to determine the cross protection against other Salmonella serovars. Blood, PP, liver and spleen are harvested from challenged mice for Salmonella enumeration in tissues to determine the kinetics of elimination of viable Salmonella as a function of time after challenge and monitor post-challenge immune responses.

Measurement of immune responses conferred by RASVs synthesizing protective antigens. Serum IgG and mucosal SIgA responses from vaginal washes in immunized mice are evaluated by ELISA using the protective antigens, OMPs, IROMPs and LPS from different serovars at 2 and 4 weeks, as well as IgG1 and IgG2a titers to distinguish between Th1 and Th2 responses. At 4 weeks post-immunization, the splenocyte responses to stimulation with purified Salmonella antigens or Salmonella are determined for measurement of T-cell immunity by ELISPOT to determine the CD4 T-cell profile that produce IL-4, IFN-γ and IL-17 (201). Since the amount of secreted IgA obtained in vaginal washes may not accurately reflect the mucosal response in the gut, the number of IgA secreting cells present in the lamina propria of the intestine is measured by antigen-specific IgA ELISPOT. Sera are collected for cytokine assays using a multiplex assay at 24, 48 and 72 h post-challenge using the Bio-plex Protein Array System (BIO-RAD) according to the manufacturer's instructions (202). The cytokines IL-2, IL-4, IL-6, IL-10, IL-17A, IFN-γ, TNF-α, IL-21 and IL-23 are measured as a result of co-cultures of the T lymphocytes with Salmonella antigens to determine the T-cell differentiation pathways among Th1/Th2/Th17/Tth using a Bioplex assay (202-204). Specially, IL-1β and IL-18 are monitored for bacterial multiplication in the liver and spleen (41, 205, 206), TNF-α and IL-6 for LPS induced cytokines (207, 208). Flow cytometry is used to determine distribution of the memory B and T cells in mouse PBMCs and tissues (209, 210) and T-cell proliferation by CFSE staining (211-218).

Example 6: Construction and Evaluation of Group D RASV S. Enteritidis Strains with Rhamnose-Regulated Delayed O-Antigen Synthesis, Mannose-Regulated O-Antigen Side Chain Synthesis and Arabinose-Regulated Production of GMMA or Outer Membrane Vesicles Synthesizing Protective Antigens In Vivo RASV-Enteritidis strains with the same features as RASV-Typhimurium synthesizing protective antigens will be constructed and evaluated in parallel with RASV-Typhimurium as a complementary strategy. The suicide vectors used for S. Typhimurium may be used for S. Enteritidis due to the high homology between the two serovars. Since there is no animal model for S. Typhi, this work also facilitates the translation of results to S. typhi because both of them are group D *Salmonella*. It may also help to use as a bivalent vaccine or for prime-boost immunization against the majority of NTS infections (219).

Construction of RASV Enteritidis Vaccine Strains Similar strategies are used to construct S. enteritidis strains with the mutations, ΔwaaL, ΔP$_{rhaBAD}$ waaL, Δpmi, ΔP$_{fur}$ and ΔP$_{tolR}$, derived from S. enteritidis χ3550, to generate vaccine strain B 1. A ΔP$_{tolR}$ mutation will be added to strain χ12457, derived from strain χ3550 with mutations ΔwaaL, ΔP$_{rhaBAD}$ waaL, Δpmi and ΔP$_{fur}$, to generate vaccine strain B1. The virulence of the resulting strain is assessed in BALB/c mice. Mutations to reduce the lipid A toxicity are introduced if the strain is still virulent (220, 221). Providing the strain is attenuated as expected, immunized mice are challenged orally with 100×LD$_{50}$ of wild-type S. Typhimurium strain χ3761. If protection is observed, subsequent studies determine the cross protection against other *Salmonella* serovars. Assuming the strain is adequately attenuated and provides some protection, ΔrelA and ΔasdA are introduced to generate strain B2 to facilitate its use as a vector.

In Vitro Evaluation of RASV Enteritidis Antigen Delivery Vector.

The best vector from Example 3 is introduced into strain B2. The resulting recombinant strain is evaluated for antigen synthesis, plasmid stability and other characters in vitro and in vivo essentially as described in Example 3.

Animal Experiments and Measurement of Immune Responses Conferred by RASV-Enteritidis Synthesizing Protective Antigens.

Similar procedures and tests are carried out as in Example 3 except S. Typhimurium will be challenged first, and then other serovars.

Example 7. Improved Performance of RASV Against *Clostridium perfringens*-Induced Necrotic Enteritis in Broiler Chickens with Strains Displaying the Regulated Delayed Lysis In Vivo Phenotype and Other Attenuation and Protective Antigen Synthesis Attributes Dependent on Two Versus Three Sugar Regulated Properties To determine the protective effects of a recombinant bacterial strain or RASV comprising three sugar-regulatable attribute systems versus two sugar-regulatable attribute systems, the following experiments were performed.

I. Comparative Immunogenicity and Protective Immunity of χ11802 Versus χ12341

Broiler chickens were orally immunized with one of the following *Salmonella enterica* strains:

χ11802 ΔP$_{murA25}$::TT araC P$_{BAD}$ murA ΔasdA27::TT araC P$_{BAD}$ c2 Δpmi-2426 Δ(wza-wcaM)-8 ΔrelA 198:: araC P$_{BAD}$ lacI TT ΔrecF126 (arabinose- and mannose-regulatable phenotypes) comprising pYA5112 (described in Jiang et al. (2015) Avian Diseases 59:475-85 (188), the entire contents of which are incorporated herein by reference) encoding an operon for synthesis of PlcC and a NetB fusion as *C. perfringens* protective antigens.

χ12341 ΔP$_{murA25}$::TT araC P$_{BAD}$ murA ΔasdA27::TT araC P$_{BAD}$ c2 Δpmi-2426 ΔwaaL46 ΔpagL64::TT rhaRS P$_{rhaBAD}$ waaL Δ(wza-wcaM)-8 ΔrelA197::araC P$_{BAD}$ lacI TT ΔrecF126 ΔsifA26 (arabinose-, mannose- and rhamnose-regulatable phenotypes) comprising pYA3681 as the empty vector control or pYA5112 encoding an operon for synthesis of PlcC and a NetB fusion as *C. perfringens* protective antigens.

The study consisted of 48 cages starting with 384 chicks. The treatments were replicated in 6 blocks of 8 cages each. The study began when the birds were placed (day of hatch) (DOT 0) at which time they were allocated to the experimental cages. No birds were replaced during the course of the study.

TABLE 3

Treatment Groups

| Treatment | | Coccidial Challenge | *Clostridium perfringens* | Cages/Trt |
|---|---|---|---|---|
| T1 | Nonmedicated | DOT 14 | No | 8 |
| T2 | Nonmedicated | DOT 14 | DOT 19, 20, and 21 | 8 |
| T3 | Vaccine 1* | DOT 14 | DOT 19, 20, and 21 | 8 |
| T4 | Vaccine 2* | DOT 14 | DOT 19, 20, and 21 | 8 |
| T5 | χ12341 comprising pYA3681 (Vector Control)* | DOT 14 | DOT 19, 20, and 21 | 8 |
| T6 | BMD 50 g/t | DOT 14 | DOT 19, 20, and 21 | 8 |

*Oral gavage on DOT 0.
Vaccine 1: χ11802(pYA5112);
Vaccine 2: χ12341(pYA5112)

Experimental Ration

An unmedicated chicken starter compounded with feedstuffs commonly used in the United States was formulated. The diet was representative of a local commercial formulation and calculated analyses met or exceeded NRC broiler starter requirements. The diet formulation was included in the source data. Experimental treatment feeds were prepared from this basal starter feed. Quantities of all basal feed and test articles used to prepare treatment batches were documented. Treatment feeds were mixed to assure a uniform distribution of respective test article. The mixer was flushed to prevent cross contamination. The feed was transferred to Building #2 and distributed among cages of the same treatment. At placement, the birds were fed the treatment feeds. This ration (in mash form) was fed during the study. Feed was weighed in on DOT 0 and remaining feed was weighed on DOT 14, 21, and 28.

Feed Samples

One each from the beginning, middle, and end of each batch of treatment diet was collected and mixed to form a composite sample. One sample was taken from the composite for each treatment and retained for a period of six (6) months after study completion for potential feed analysis.

Animals

Day of hatch male broiler chicks were obtained from Cobb-Vantress, Cleveland, Ga. The strain was Cobb 500. Breeder flock information was recorded. At the hatchery, the birds were sexed and received routine vaccinations. Only healthy appearing chicks were used in the study. Each cage started with 8 chicks (DOT 0). All birds were weighed on DOT 0, 14, 21, and 28.

Strain Administration

Bacterial strains were administered at DOT 0 to each chick in Treatment Groups 3, 4, and 5 via oral gavaged with ~5×10$^8$ CFU/chick in a volume of 0.1 mL.

Disease Induction

On DOT 14, all birds were orally inoculated with ~5,000 oocysts of *E. maxima*.

Starting on DOT 19 all birds (except Treatment 1) were given a broth culture of *C. perfringens* ~10$^8$ CFU/ml. There were no feed removed in this study. The birds were administered 0.1 ml by oral gavage of a fresh broth culture once daily for 3 days (on DOTs 19, 20, and 21).

*Clostridium perfringens* Challenge Growth

The challenge strain used was *Clostridium perfringens* #6 (Hofacre, et al., 1998) (222). It was inoculated into one (1)

liter of thioglycolate broth supplemented with 5% beef extract and incubated at 37° C. for 15 hours.

Necrotic Enteritis Intestinal Lesion Scoring

Necrotic enteritis intestinal lesion scoring was performed as described in Hofacre, et al., 1998 (222). On DOT 21, three birds from each cage four (4) hours post third *Clostridium perfringens* challenge were selected, sacrificed, weighed, and examined for the degree of presence of Necrotic Enteritis lesions. The scoring was based on a 0 to 3 score, with 0 being normal and 3 being the most severe.

Data Analysis

Statistical analysis of cage weight gain, feed consumption, feed conversion, lesion scores, and NE mortality were calculated. The results of the experiment are shown below at Table 4.

TABLE 4

Determining the best vaccine strain genotype

| Treatments | Feed Conversion | | Weight Gain (kg) | | Feed Conversion | | Weight Gain (kg) | | NE Lesions | % NE Mortality |
|---|---|---|---|---|---|---|---|---|---|---|
| | D0-21 | D14-21 | D0-21 | D14-21 | D0-28 | D14-28 | D0-28 | D14-28 | | |
| 1. No Additive, No CP | 2.054b | 1.626c | 0.286a | 0.164a | 1.958b | 1.706b | 0.657a | 0.535a | 0.0d | 0.0a |
| 2. No Additive, CP | 2.585a | 2.053ab | 0.226b | 0.125b | 2.241a | 1.875ab | 0.506b | 0.405b | 0.9a | 6.3a |
| 3. χ11802(pYA5112), CP | 2.340ab | 2.093a | 0.270ab | 0.142ab | 2.106ab | 1.888a | 0.627ab | 0.499ab | 0.8a | 6.3a |
| 4. χ12341(pYA5112), CP | 2.161b | 1.826bc | 0.294a | 0.154a | 1.937b | 1.698b | 0.709a | 0.570a | 0.3cd | 0.0a |
| 5. Vector Control, CP | 2.316ab | 2.043ab | 0.276ab | 0.153a | 2.060ab | 1.854ab | 0.649a | 0.527a | 0.6ab | 4.7a |
| 6. BMD 50 g/t, CP | 2.235b | 1.889ab | 0.268ab | 0.152a | 1.981b | 1.742ab | 0.642a | 0.526a | 0.5bc | 1.6a | a: b: c: d:

TABLE 5

Determining the effect of varying doses of RASV χ12341(pYA5112)

| Treatments | Feed Conversion | | Weight Gain (kg) | | Feed Conversion | | Weight Gain (kg) | | NE Lesions | % NE Mortality |
|---|---|---|---|---|---|---|---|---|---|---|
| | D0-21 | D14-21 | D0-21 | D14-21 | D0-28 | D14-28 | D0-28 | D14-28 | | |
| 1. No Additive, No CP | 1.714c | 1.842d | 0.509a | 0.223a | 1.807b | 1.917c | 0.710a | 0.423a | 0.1b | 0.0c |
| 2. No Additive, CP | 2.329a | 3.188a | 0.354c | 0.119e | 2.210a | 2.517a | 0.501c | 0.266d | 0.4ab | 15.6a |
| 3. χ12341(pYA5112), Original titer, CP | 2.264ab | 2.197cd | 0.399b | 0.179b | 2.164a | 2.066bc | 0.602b | 0.382ab | 0.4a | 1.6bc |
| 4. χ12341(pYA5112), Intermediate titer, CP | 2.240ab | 2.444bc | 0.390bc | 0.149cd | 2.121a | 2.172bc | 0.570bc | 0.329bcd | 0.5a | 1.6bc |
| 5. χ12341(pYA5112), low titer, CP | 2.386a | 2.415bc | 0.375bc | 0.159bcd | 2.231a | 2.134bc | 0.571bc | 0.355abc | 0.5a | 6.3b |
| 6. Vector Control, CP | 2.307a | 2.754b | 0.378bc | 0.137de | 2.165a | 2.286ab | 0.537bc | 0.296cd | 0.5a | 4.7bc |
| 7. BMD 50 g/t, CP | 2.040b | 2.142cd | 0.407b | 0.166bc | 2.039a | 2.098bc | 0.591bc | 0.351abc | 0.5a | 1.6bc |

As shown in Table 4, χ12341(pYA5112) was superior to χ11802(pYA5112) (and the vector and unimmunized controls) in feed conversion efficiency and weight gain and with lower lesion scores and mortality.

I. Effect of Dose of RASV χ12341(pYA5112).

To assess the effect of dosing of RASV χ12341 (pYA5112), the following experiment was performed using either low titer ($5\times10^7$ CFU); intermediate titer ($1.5\times10^8$ CFU) or the original titer (as described above; $5\times10^8$ CFU) of the RASV χ12341(pYA5112) bacterial strain.

Materials and Methods

A. Experimental Ration

An unmedicated chicken starter compounded with feedstuffs commonly used in the United States was formulated. The diet was representative of a local commercial formulation and calculated analyses met or exceeded NRC broiler starter requirements. Experimental treatment feeds were prepared from this basal starter feed. Quantities of all basal feed and test articles used to prepare treatment batches were documented. Treatment feeds were mixed to assure a uniform distribution of respective test article. The mixer was flushed to prevent cross contamination. The feed was distributed among cages of the same treatment. This ration (in mash form) was fed during the study.

B. Animals

Day of hatch male broiler chicks were obtained from Cobb-Vantress, Cleveland, Ga. The strain was Cobb 500. Breeder flock information was recorded. At the hatchery, the birds were sexed and received routine vaccinations. Only healthy appearing chicks were used in the study. Disposition of all birds not used for allocation were documented. Papers or swabs from bottom of all chick boxes were cultured for presence of *Salmonella*.

Procedures a. Bird Allocation and Cage Randomization

The study began when the birds were placed (day of hatch) (DOT 0) at which time they were allocated to the experimental cages. No birds were replaced during the course of the study.

b. Vaccine Administration

Bacterial strains were administered at DOT 0 to each chick in Treatment Groups 3, 4, 5 and 6 via oral gavaged with ~$5\times10^8$ CFU/chick in a volume of 0.1 mL.

c. Cage Weights

All birds were weighed on DOT 0, 14, 21, and 28. Feed was weighed in on DOT 0 and remaining feed was weighed on DOT 14, 21, and 28.

d. Disease Induction

On DOT 14, all birds were orally inoculated with ~-5,000 oocysts of *E. maxima*. Starting on DOT 19 all birds (except Treatment 1) were given a broth culture of *C. perfringens* ~$10^8$ CFU/ml. No feed was removed in this study. The birds were administered 0.1 ml by oral gavage of a fresh broth culture once daily for 3 days (on DOTs 19, 20, and 21).

e. *Clostridium perfringens* Challenge Growth

The challenge strain used was *Clostridium perfringens* #6 (as described in Hofacre, et al., 1998 (222)). It was inoculated into one (1) liter of thioglycolate broth supplemented with 5% beef extract and incubated at 37° C. for 15 hours.

f. Necrotic Enteritis Intestinal Lesion Scoring

On DOT 21, three birds from each cage four (4) hours post third *Clostridium perfringens* challenge were selected, sacrificed, weighed, and examined for the degree of presence of Necrotic Enteritis lesions. The scoring was based on a 0 to 3 score, with 0 being normal and 3 being the most severe. All of the three lesion score birds were bled for serum storage.

g. Data Analysis and Results

Statistical analysis of cage weight gain, feed consumption, feed conversion, lesion scores, and mortality were calculated. The results of the experiment are shown below at Table 5. As shown in Table 5, the original and intermediate RASV doses were superior to the low dose or the controls.

III. Effect of Route of Immunization.

To determine the effect of the route of administration of RASV χ12341(pYA5112), chicks were immunized with either a high dose (5×$10^8$ CFU) or mid dose (1×$10^8$ CFU) of the χ12341(pYA5112) bacterial strain either by oral gavage, spray, or orally (in drinking water). Briefly, at DOT 0, each chick was orally gavaged with 0.1 ml of the bacterial strain, ~5×$10^8$ CFU/chick; On DOT 14, all birds were orally inoculated with ~5,000 oocysts of *E. maxima*. Starting on DOT 19 all birds (except Treatment 1) were given a broth culture of *C. perfringens* (CP) ~$10^8$ CFU/ml once daily for 3 days (on DOTs 19, 20, and 21). On DOT 21, three birds from each cage four (4) hours post third *Clostridium perfringens* challenge were examined for the degree of presence of Necrotic Enteritis lesions. The scoring was based on a 0 to 3 score, with 0 being normal and 3 being the most severe.

As shown in Table 6, all routes of immunization were superior to the control unvaccinated group. Moreover, the spray immunization group resulted in satisfactory performance as compared to the oral gavage groups. This is commercially important since spray immunization in hatcheries is the preferred and most economical means of immunization for poultry.

TABLE 6

Effects of the route of immunization of χ12341(pYA5112)

| | Feed Conversion | | Weight Gain (kg) | | Feed Conversion | | Weight Gain (kg) | | NE | % NE |
|---|---|---|---|---|---|---|---|---|---|---|
| Treatments | D0-21 | D14-21 | D0-21 | D14-21 | D0-28 | D14-28 | D0-28 | D14-28 | Lesions | Mortality |
| 1. No Additive, No CP | 1.683d | 1.883d | 0.524a | 0.240a | 1.765c | 1.937d | 0.836a | 0.552a | 0.0c | 0.0c |
| 2. No Additive, CP | 1.984a | 2.729a | 0.445bc | 0.164d | 2.212a | 3.271a | 0.635c | 0.353c | 0.9a | 40.6a |
| 3. χ12341(pYA5112)-High dose gavaged, CP | 1.958ab | 2.540ab | 0.436c | 0.172cd | 1.975bc | 2.361bc | 0.664bc | 0.400bc | 0.7ab | 20.3b |
| 4. χ12341(pYA5112)-Mid dose gavaged, CP | 1.814bcd | 2.213c | 0.468bc | 0.191bc | 1.835bc | 2.115bcd | 0.770ab | 0.496ab | 0.4bc | 12.5bc |
| 5. χ12341(pYA5112)-High dose sprayed, CP | 1.905abc | 2.493b | 0.451bc | 0.173bcd | 1.855bc | 2.189bcd | 0.773ab | 0.478ab | 0.9a | 20.3b |
| 6. χ12341(pYA5112)-High dose in drinking $H_2O$, CP | 1.904abc | 2.574ab | 0.467bc | 0.169cd | 1.978b | 2.508b | 0.789a | 0.491ab | 0.8ab | 20.3b |
| 7. BMD 50 g/t, CP | 1.760cd | 2.114c | 0.487ab | 0.197b | 1.805bc | 2.071cd | 0.832a | 0.542a | 0.4bc | 17.2b |

Example 8. Inability of High Concentrations of One Sugar to Interfere with Ability of Two Other Sugars at Low Concentrations to Regulate Genes Needed for Survival of RASV Strains with the Regulated Delayed Lysis In Vivo Phenotype χ12341(pYA4763) has an obligate requirement for arabinose to survive since it has araC $P_{araBAD}$-regulated murA genes both in the chromosome and in the pYA4763 plasmid. Since the product of the murA gene-encoded enzyme is phosphorylated and since *Salmonella* cannot take up phosphorylated sugars, the χ12341(pYA4763) strain constitutes an arabinose-dependent lethal construction. Thus any exogenous sugar that would block the ability of arabinose to be either taken up by χ12341(pYA4763) or to cause transcription of the murA gene by activation of the $P_{araBAD}$ promoter would result in lethality of χ12341(pYA4763) cells. To determine whether addition of high concentrations (i.e., 1.0%) of any of the three sugars used by χ12341(pYA4763) interferes with the activities of the other two sugars at lower concentrations (i.e., 0.1% or lower) to enable survival or display of the phenotype regulated, the following experiments were performed. Growth experiments were performed using buffered Purple broth (to avoid any pH change due sugar utilization).

Briefly, the growth of *Salmonella* strains χ12341 (pYA4763) and χ3761 was assessed during a 24 h period in growth media with varying sugar concentrations. Briefly, an overnight culture of each strain was grown in buffered purple broth+0.05% arabinose+0.1% rhamnose+0.1% mannose. A subculture was made by diluting at 1:100 (FIGS. 6A, 6B, 6G, 6H, 6M, and 6N), 1:1,000 (FIGS. 6C, 6D, 6I, 6J, 6O, and 16P), or 1:10,000 (FIGS. 6E, 6F, 6K, 6L, 6Q, and 6R) into pre-warmed buffered purple broth with varying concentrations of arabinose, rhamnose, and mannose. 200 μL of each culture was added to an individual well in a 100-well plate in duplicate for each strain and sugar condition. The plate was inserted into the Bioscreen C Automated Microbiology Growth Curve Analysis System set at 37° C. and was left to incubate, with shaking, for 24 h. Optical densities were measured every 30 min. and compared to a blank to confirm purity. The figures present the data with all conditions (FIGS. 6A-6F), comparing the conditions that had 1% of one of the three sugars (FIGS. 6G-6L) and comparing various concentrations of arabinose (FIGS. 6M-6R).

As shown in FIGS. 6A-6R, the χ12341(pYA4763) bacterial strain grows as well as wild-type S. Typhimurium UK-1 strain independent of the presence of any one sugar at a 1.0% concentration and the other two sugars at 0.1% or lower concentrations. It should be noted that Purple broth is devoid of all sugars such that there can be no interference in results due to trace amounts of arabinose, mannose or rhamnose. These results demonstrate that high concentrations of rhamnose or mannose do not inhibit the ability of low concentrations of arabinose to cause expression of the murA gene since no cell death was observed.

Western blot analysis can be performed to analyze the expression of genes encoding products regulated by one of the sugar-regulatable promoters in the χ12341(pYA4763) strain.

REFERENCES

1. Lozano R, Naghavi M, Foreman K, Lim S, Shibuya K, Aboyans V, Abraham J, Adair T, Aggarwal R, Ahn S Y, Alvarado M, Anderson H R, Anderson L M, Andrews K G, Atkinson C, Baddour L M, Barker-Collo S, Bartels D H, Bell M L, Benjamin E J, Bennett D, Bhalla K, Bikbov B, Bin Abdulhak A, Birbeck G, Blyth F, Bolliger I, Boufous S, Bucello C, Burch M, Burney P, Carapetis J, Chen H, Chou D, Chugh S S, Coffeng L E, Colan S D, Colquhoun S, Colson K E, Condon J, Connor M D, Cooper L T, Corriere M, Cortinovis M, de Vaccaro K C, Couser W, Cowie B C, Criqui M H, Cross M, Dabhadkar K C, et al. 2012. Global and regional mortality from 235 causes of death for 20 age groups in 1990 and 2010: a systematic analysis for the Global Burden of Disease Study 2010. Lancet 380:2095-2128.
2. Tennant S M, Levine M M. 2015. Live attenuated vaccines for invasive Salmonella infections. Vaccine 33 Suppl 3:C36-C41.
3. Wain J, Hendriksen R S, Mikoleit M L, Keddy K H, Ochiai R L. 2015. Typhoid fever. Lancet 385:1136-1145.
4. Sahastrabuddhe S, Carbis R, Wierzba T F, Ochiai R L. 2013. Increasing rates of Salmonella Paratyphi A and the current status of its vaccine development. Expert Rev Vaccines 12:1021-1031.
5. Mogasale V, Maskery B, Ochiai R L, Lee J S, Mogasale V V, Ramani E, Kim Y E, Park J K, Wierzba T F. 2014. Burden of typhoid fever in low-income and middle-income countries: a systematic, literature-based update with risk-factor adjustment. Lancet Glob Health 2:e570-580.
6. Crump J A, Luby S P, Mintz E D. 2004. The global burden of typhoid fever. Bull World Health Organ 82:346-353.
7. Murray C J, Vos T, Lozano R, Naghavi M, Flaxman A D, Michaud C, Ezzati M, Shibuya K, Salomon J A, Abdalla S, Aboyans V, Abraham J, Ackerman I, Aggarwal R, Ahn S Y, Ali M K, Alvarado M, Anderson H R, Anderson L M, Andrews K G, Atkinson C, Baddour L M, Bahalim A N, Barker-Collo S, Barrero L H, Bartels D H, Basanez M G, Baxter A, Bell M L, Benjamin E J, Bennett D, Bernabe E, Bhalla K, Bhandari B, Bikbov B, Bin Abdulhak A, Birbeck G, Black J A, Blencowe H, Blore J D, Blyth F, Bolliger I, Bonaventure A, Boufous S, Bourne R, Boussinesq M, Braithwaite T, Brayne C, Bridgett L, Brooker S, et al. 2012. Disability-adjusted life years (DALYs) for 291 diseases and injuries in 21 regions, 1990-2010: a systematic analysis for the Global Burden of Disease Study 2010. Lancet 380:2197-2223.
8. Feasey N A, Dougan G, Kingsley R A, Heyderman R S, Gordon M A. 2012. Invasive non-typhoidal Salmonella disease: an emerging and neglected tropical disease in Africa. Lancet 379:2489-2499.
9. Chiu C H, Su L H, Chu C. 2004. Salmonella enterica serotype Choleraesuis: epidemiology, pathogenesis, clinical disease, and treatment. Clin Microbiol Rev 17:311-322.
10. Ao T T, Feasey N A, Gordon M A, Keddy K H, Angulo F J, Crump J A. 2015. Global burden of invasive nontyphoidal Salmonella disease, 2010(1). Emerg Infect Dis 21.
11. Majowicz S E, Musto J, Scallan E, Angulo F J, Kirk M, O'Brien S J, Jones T F, Fazil A, Hoekstra R M, International Collaboration on Enteric Disease 'Burden of Illness S. 2010. The global burden of nontyphoidal Salmonella gastroenteritis. Clin Infect Dis 50:882-889.
12. Scallan E, Hoekstra R M, Mahon B E, Jones T F, Griffin P M. 2015. An assessment of the human health impact of seven leading foodborne pathogens in the United States using disability adjusted life years. Epidemiol Infect 143:2795-2804.
13. Scallan E, Hoekstra R M, Angulo F J, Tauxe R V, Widdowson M A, Roy S L, Jones J L, Griffin P M. 2011. Foodborne illness acquired in the United States—major pathogens. Emerg Infect Dis 17:7-15.
14. Hoffmann S, Batz M B, Morris J G, Jr. 2012. Annual cost of illness and quality-adjusted life year losses in the United States due to 14 foodborne pathogens. J Food Prot 75:1292-1302.
15. Scallan E, Mahon B E, Hoekstra R M, Griffin P M. 2013. Estimates of illnesses, hospitalizations and deaths caused by major bacterial enteric pathogens in young children in the United States. Pediatr Infect Dis J 32:217-221.
16. Olsen S J, Bishop R, Brenner F W, Roels T H, Bean N, Tauxe R V, Slutsker L. 2001. The changing epidemiology of Salmonella: trends in serotypes isolated from humans in the United States, 1987-1997. J Infect Dis 183:753-761.
17. Jackson B R, Griffin P M, Cole D, Walsh K A, Chai S J. 2013. Outbreak-associated Salmonella enterica serotypes and food Commodities, United States, 1998-2008. Emerg Infect Dis 19:1239-1244.
18. Gordon M A. 2008. Salmonella infections in immunocompromised adults. J Infect 56:413-422.
19. Preziosi M J, Kandel S M, Guiney D G, Browne S H. 2012. Microbiological analysis of nontyphoidal Salmonella strains causing distinct syndromes of bacteremia or enteritis in HIV/AIDS patients in San Diego, Calif. J Clin Microbiol 50:3598-3603.
20. MacLennan C A, Levine M M. 2013. Invasive nontyphoidal Salmonella disease in Africa: current status. Expert Rev Anti Infect Ther 11:443-446.
21. Graham S M, Molyneux E M, Walsh A L, Cheesbrough J S, Molyneux M E, Hart C A. 2000. Nontyphoidal Salmonella infections of children in tropical Africa. Pediatr Infect Dis J 19:1189-1196.
22. Crump J A, Medalla F M, Joyce K W, Krueger A L, Hoekstra R M, Whichard J M, Barzilay E J, Emerging Infections Program NWG. 2011. Antimicrobial resistance among invasive nontyphoidal Salmonella enterica iso- 23. Bhutta Z A, Threlfall J. 2009. Addressing the global disease burden of typhoid fever. JAMA 302:898-899.
24. Jean S S, Hsueh P R. 2011. High burden of antimicrobial resistance in Asia. Int J Antimicrob Agents 37:291-295.
25. Crump J A, Mintz E D. 2010. Global trends in typhoid and paratyphoid Fever. Clin Infect Dis 50:241-246.
26. Martin L B. 2012. Vaccines for typhoid fever and other salmonelloses. Curr Opin Infect Dis 25:489-499.
27. MacLennan C A, Martin L B, Micoli F. 2014. Vaccines against invasive Salmonella disease: current status and future directions. Hum Vaccin Immunother 10:1478-1493.
28. Engels E A, Falagas M E, Lau J, Bennish M L. 1998. Typhoid fever vaccines: a meta-analysis of studies on efficacy and toxicity. BMJ 316:110-116.
29. Anwar E, Goldberg E, Fraser A, Acosta C J, Paul M, Leibovici L. 2014. Vaccines for preventing typhoid fever. Cochrane Database Syst Rev 1:CD001261.
30. Germanier R, Fuer E. 1975. Isolation and characterization of Gal E mutant Ty 21a of Salmonella typhi: a candidate strain for a live, oral typhoid vaccine. J Infect Dis 131:553-558.
31. Tacket C O, Ferreccio C, Robbins J B, Tsai C M, Schulz D, Cadoz M, Goudeau A, Levine M M. 1986. Safety and immunogenicity of two Salmonella typhi Vi capsular polysaccharide vaccines. J Infect Dis 154:342-345.
32. Desin T S, Koster W, Potter A A. 2013. Salmonella vaccines in poultry: past, present and future. Expert Rev Vaccines 12:87-96.
33. Gal-Mor O, Boyle E C, Grassi G A. 2014. Same species, different diseases: how and why typhoidal and non-typhoidal Salmonella enterica serovars differ. Front Microbiol 5:391.
34. Bhavsar A P, Zhao X, Brown E D. 2001. Development and characterization of a xylose-dependent system for expression of cloned genes in Bacillus subtilis: conditional complementation of a teichoic acid mutant. Appl Environ Microbiol 67:403-410.
35. Walder R Y, Walder J A. 1986. Oligodeoxynucleotide-directed mutagenesis using the yeast transformation system. Gene 42:133-139.
36. Bauer C E, Hesse S D, Waechter-Brulla D A, Lynn S P, Gumport R I, Gardner J F. 1985. A genetic enrichment for mutations constructed by oligodeoxynucleotide-directed mutagenesis. Gene 37:73-81.
37. Craik C S. 1985. Use Of Oligonucleotides For Site-specific Mutagenesis BIOTECHNIQUES 3:12-19.
38. Smith M, Gillam S. 1981. Constructed Mutants Using Synthetic Oligodeoxyribonucleotides as Site-Specific Mutagens, p 1-32. In Setlow J K, Hollaender A (ed), Genetic Engineering: Principles and Methods Volume 3 doi:10.1007/978-1-4615-7075-2_1. Springer US, Boston, Mass.
39. Giacalone M J, Gentile A M, Lovitt B T, Berkley N L, Gunderson C W, Surber M W. 2006. Toxic protein expression in Escherichia coli using a rhamnose-based tightly regulated and tunable promoter system. Biotechniques 40:355-364.
40. Elhenawy W, Bording-Jorgensen M, Valguarnera E, Haurat M F, Wine E, Feldman M F. 2016. LPS Remodeling Triggers Formation of Outer Membrane Vesicles in Salmonella. MBio 7:e00940-00916.
41. Man S M, Hopkins L J, Nugent E, Cox S, Gluck I M, Tourlomousis P, Wright J A, Cicuta P, Monie T P, Bryant C E. 2014. Inflammasome activation causes dual recruitment of NLRC4 and NLRP3 to the same macromolecular complex. Proc Natl Acad Sci USA 111:7403-7408.
42. Collins L V, Attridge S, Hackett J. 1991. Mutations at rfc or pmi attenuate Salmonella typhimurium virulence for mice. Infect Immun 59:1079-1085.
43. Curtiss R, Ill., Zhang X, Wanda S Y, Kang H Y, Konjufca V, Li Y, Gunn B, Wang S, Scarpellini G, Lee I S. 2007. Induction of host immune responses using Salmonella-vectored vaccines, p 297-313. In Brogden K A, Minion F C, Cornick N, Stanton T B, Zhang Q, Nolan L K, Wannemuehler M J (ed), Virulence mechanisms of bacterial pathogens, 4th ed. ASM Press, Washington D.C.
44. Raetz C R, Whitfield C. 2002. Lipopolysaccharide endotoxins. Annu Rev Biochem 71:635-700.
45. Frey P A. 1996. The Leloir pathway: a mechanistic imperative for three enzymes to change the stereochemical configuration of a single carbon in galactose. FASEB J 10:461-470.
46. Leloir L F. 1951. The enzymatic transformation of uridine diphosphate glucose into a galactose derivative. Arch Biochem Biophys 33:186-190.
47. Germanier R, Furer E. 1971. Immunity in experimental salmonellosis. II. Basis for the avirulence and protective capacity of galE mutants of Salmonella typhimurium. Infect Immun 4:663-673.
48. Fukasawa T, Nikaido H. 1959. Galactose-sensitive mutants of Salmonella. Nature 184(Suppl 15):1168-1169.
49. Lee S J, Trostel A, Le P, Harinarayanan R, Fitzgerald P C, Adhya S. 2009. Cellular stress created by intermediary metabolite imbalances. Proc Natl Acad Sci USA 106:19515-19520.
50. Hone D, Morona R, Attridge S, Hackett J. 1987. Construction of defined galE mutants of Salmonella for use as vaccines. J Infect Dis 156:167-174.
51. Cascales E, Buchanan S K, Duche D, Kleanthous C, Lloubes R, Postle K, Riley M, Slatin S, Cavard D. 2007. Colicin biology. Microbiol Mol Biol Rev 71:158-229.
52. Mastroeni P, Simmons C, Fowler R, Hormaeche C E, Dougan G. 2000. Igh-6$^{-/-}$ (B-cell-deficient) mice fail to mount solid acquired resistance to oral challenge with virulent Salmonella enterica serovar typhimurium and show impaired Th1 T-cell responses to Salmonella antigens. Infect Immun 68:46-53.
53. Ugrinovic S, Menager N, Goh N, Mastroeni P. 2003. Characterization and development of T-Cell immune responses in B-cell-deficient (Igh-6$^{-/-}$) mice with Salmonella enterica serovar Typhimurium infection. Infect Immun 71:6808-6819.
54. Mittrucker H W, Raupach B, Kohler A, Kaufmann S H. 2000. Cutting edge: role of B lymphocytes in protective immunity against Salmonella typhimurium infection. J Immunol 164:1648-1652.
55. Mastroeni P, Menager N. 2003. Development of acquired immunity to Salmonella. J Med Microbiol 52:453-459.
56. Pham O H, McSorley S J. 2015. Protective host immune responses to Salmonella infection. Future Microbiol 10:101-110.
57. Cunningham A F, Gaspal F, Serre K, Mohr E, Henderson I R, Scott-Tucker A, Kenny S M, Khan M, Toellner K M, Lane P J, MacLennan I C. 2007. Salmonella induces a switched antibody response without germinal centers that impedes the extracellular spread of infection. J Immunol 178:6200-6207.
58. MacLennan C A, Gondwe E N, Msefula C L, Kingsley R A, Thomson N R, White S A, Goodall M, Pickard D J, 58. Graham S M, Dougan G, Hart C A, Molyneux M E, Drayson M T. 2008. The neglected role of antibody in protection against bacteremia caused by nontyphoidal strains of *Salmonella* in African children. J Clin Invest 118:1553-1562.
59. Guzman C A, Borsutzky S, Griot-Wenk M, Metcalfe I C, Pearman J, Collioud A, Favre D, Dietrich G. 2006. Vaccines against typhoid fever. Vaccine 24:3804-3811.
60. MacLennan C A. 2014. Antibodies and protection against invasive *Salmonella* disease. Front Immunol 5:635.
61. Isibasi A, Ortiz V, Vargas M, Paniagua J, Gonzalez C, Moreno J, Kumate J. 1988. Protection against *Salmonella* typhi infection in mice after immunization with outer membrane proteins isolated from *Salmonella* typhi 9, 12,d, Vi. Infect Immun 56:2953-2959.
62. Klugman K P, Gilbertson I T, Koornhof H J, Robbins J B, Schneerson R, Schulz D, Cadoz M, Armand J. 1987. Protective activity of Vi capsular polysaccharide vaccine against typhoid fever. Lancet 2:1165-1169.
63. Acharya I L, Lowe C U, Thapa R, Gurubacharya V L, Shrestha M B, Cadoz M, Schulz D, Armand J, Bryla D A, Trollfors B, et al. 1987. Prevention of typhoid fever in Nepal with the Vi capsular polysaccharide of *Salmonella* typhi. A preliminary report. N Engl J Med 317:1101-1104.
64. Szu S C. 2013. Development of Vi conjugate—a new generation of typhoid vaccine. Expert Rev Vaccines 12:1273-1286.
65. Jansson P E, Lindberg A A, Lindberg B, Wollin R. 1981. Structural studies on the hexose region of the core in lipopolysaccharides from Enterobacteriaceae. Eur J Biochem 115:571-577.
66. Lüderitz O, Westphal O, Staub A M, Nikaido H. 1971. Isolation and Chemical and Immunological Characterization of Bacterial Lipopolysaccharides, p 145-223. In Weinbaum G, Kadis S, Ajl S J (ed), Bacterial Endotoxins, vol 4. in Microbial Toxins. Academic Press, Inc, New York.
67. Kaniuk N A, Monteiro M A, Parker C T, Whitfield C. 2002. Molecular diversity of the genetic loci responsible for lipopolysaccharide core oligosaccharide assembly within the genus *Salmonella*. Mol Microbiol 46:1305-1318.
68. Olsthoorn M M, Petersen B O, Schlecht S, Haverkamp J, Bock K, Thomas-Oates J E, Holst O. 1998. Identification of a novel core type in *Salmonella* lipopolysaccharide. Complete structural analysis of the core region of the lipopolysaccharide from *Salmonella enterica* sv. Arizonae 062. J Biol Chem 273:3817-3829.
69. Malik M, Butchaiah G, Bansal M P, Siddiqui M Z, Bakshi C S, Singh R K. 2002. Antigenic relationships within the genus *Salmonella* as revealed by anti-*Salmonella enteritidis* monoclonal antibodies. Vet Res Commun 26:179-188.
70. Earhart C F. 1996. Uptake and metabolism of iron and molybdenum., p 1075-1090. In Neidhardt F C, Curtiss III R, Ingraham J L, Lin E C C, Low K B, Magasanik B, Reznikoff W S, Riley M, Schaechter M, Umbarger H E (ed), *Escherichia coli* and *Salmonella* Cellular and Molecular Biology, 2nd ed, vol 1. ASM Press, Washington, D.C.
71. Collins L V, Attridge S, Hackett J. 1991. Mutations at rfc or pmi attenuate *Salmonella* typhimurium virulence for mice. Infect Immun 59:1079-1085.
72. Rosen S M, Zeleznick L D, Fraenkel D, Wiener I M, Osborn M J, Horecker B L. 1965. Characterization of the cell wall lipopolysaccharide of a mutant of *Salmonella* typhimurium lacking phosphomannose isomerase. Biochem Z 342:375-386.
73. Mäkelä P H, Stocker B A D. 1969. Genetics of Polysaccharide Biosynthesis. Annual Review of Genetics 3:291-322.
74. Stocker B A D, Makela P H. 1971. Genetic Aspects of Biosynthesis and Structure of *Salmonella* Lipopolysaccharide, p 369-438. In Weinbaum G, Kadis S, Ajl S J (ed), Bacterial Endotoxins, vol 4. in Microbial Toxins. Academic Press, Inc, New York.
75. Curtiss R, III, Wanda S Y, Gunn B M, Zhang X, Tinge S A, Ananthnarayan V, Mo H, Wang S, Kong W. 2009. *Salmonella enterica* serovar Typhimurium strains with regulated delayed attenuation in vivo. Infect Immun 77:1071-1082.
76. Curtiss R, III, Zhang X, Wanda S Y, Kang H Y, Konjufca V, Li H, Gunn B, Wang S, Scarpellini G, S. L I. 2007. Induction of host immune responses using *Salmonella*-vectored vaccines, p 297-313. In Brogden K A, Minion F C, Stanton T B, Zhang Q, Nolan L K, Wannemuehler M J (ed), Virulence Mechanisms of Bacterial Pathogens, 4th ed. ASM Press, Washington D.C.
77. Chamnongpol S, Dodson W, Cromie M J, Harris Z L, Groisman E A. 2002. Fe(III)-mediated cellular toxicity. Mol Microbiol 45:711-719.
78. Nnalue N A. 1999. All accessible epitopes in the *Salmonella* lipopolysaccharide core are associated with branch residues. Infect Immun 67:998-1003.
79. Stanislavsky E S, Makarenko T A, Kholodkova E V, Lugowski C. 1997. R-form lipopolysaccharides (LPS) of Gram-negative bacteria as possible vaccine antigens. FEMS Immunol Med Microbiol 18:139-145.
80. Muralinath M, Kuehn M J, Roland K L, Curtiss R, III. 2011. Immunization with *Salmonella enterica* serovar Typhimurium-derived outer membrane vesicles delivering the pneumococcal protein PspA confers protection against challenge with *Streptococcus pneumoniae*. Infect Immun 79:887-894.
81. Englesberg E, Irr J, Power J, Lee N. 1965. Positive control of enzyme synthesis by gene C in the L-arabinose system. J Bacteriol 90:946-957.
82. Guzman L M, Belin D, Carson M J, Beckwith J. 1995. Tight regulation, modulation, and high-level expression by vectors containing the arabinose $P_{BAD}$ promoter. J Bacteriol 177:4121-4130.
83. Bolin C A, Jensen A E. 1987. Passive immunization with antibodies against iron-regulated outer membrane proteins protects turkeys from *Escherichia coli* septicemia. Infect Immun 55:1239-1242.
84. Lin J, Hogan J S, Smith K L. 1999. Antigenic homology of the inducible ferric citrate receptor (FecA) of coliform bacteria isolated from herds with naturally occurring bovine intramammary infections. Clin Diagn Lab Immunol 6:966-969.
85. Clifton-Hadley F A, Breslin M, Venables L M, Sprigings K A, Cooles S W, Houghton S, Woodward M J. 2002. A laboratory study of an inactivated bivalent iron restricted *Salmonella enterica* serovars Enteritidis and Typhimurium dual vaccine against Typhimurium challenge in chickens. Vet Microbiol 89:167-179.
86. Woodward M J, Gettinby G, Breslin M F, Corkish J D, Houghton S. 2002. The efficacy of Salenvac, a *Salmonella enterica* subsp. *Enterica* serotype Enteritidis iron-restricted bacterin vaccine, in laying chickens. Avian Pathol 31:383-392.

87. Berlanda Scorza F, Colucci A M, Maggiore L, Sanzone S, Rossi O, Ferlenghi I, Pesce I, Caboni M, Norais N, Di Cioccio V, Saul A, Gerke C. 2012. High yield production process for *Shigella* outer membrane particles. PLoS One 7:e35616.
88. Clementz T, Bednarski J J, Raetz C R. 1996. Function of the htrB high temperature requirement gene of *Escherichia coli* in the acylation of lipid A: HtrB catalyzed incorporation of laurate. J Biol Chem 271:12095-12102.
89. Kulp A, Kuehn M J. 2010. Biological functions and biogenesis of secreted bacterial outer membrane vesicles. Annu Rev Microbiol 64:163-184.
90. Dowling J K, Mansell A. 2016. Toll-like receptors: the swiss army knife of immunity and vaccine development. Clin Transl Immunology 5:e85.
91. Duthie M S, Windish H P, Fox C B, Reed S G. 2011. Use of defined TLR ligands as adjuvants within human vaccines. Immunol Rev 239:178-196.
92. Steinhagen F, Kinjo T, Bode C, Klinman D M. 2011. TLR-based immune adjuvants. Vaccine 29:3341-3355.
93. Lahiri A, Das P, Chakravortty D. 2008. Engagement of TLR signaling as adjuvant: towards smarter vaccine and beyond. Vaccine 26:6777-6783.
94. Ishii K J, Akira S. 2007. Toll or toll-free adjuvant path toward the optimal vaccine development. J Clin Immunol 27:363-371.
95. Toussi D N, Massari P. 2014. Immune Adjuvant Effect of Molecularly-defined Toll-Like Receptor Ligands. Vaccines (Basel) 2:323-353.
96. Koeberling O, Delany I, Granoff D M. 2011. A critical threshold of meningococcal factor H binding protein expression is required for increased breadth of protective antibodies elicited by native outer membrane vesicle vaccines. Clin Vaccine Immunol 18:736-742.
97. Koeberling O, Seubert A, Granoff D M. 2008. Bactericidal antibody responses elicited by a meningococcal outer membrane vesicle vaccine with overexpressed factor H-binding protein and genetically attenuated endotoxin. J Infect Dis 198:262-270.
98. Pajon R, Fergus A M, Koeberling O, Caugant D A, Granoff D M. 2011. Meningococcal factor H binding proteins in epidemic strains from Africa: implications for vaccine development. PLoS Negl Trop Dis 5:e1302.
99. Zollinger W D, Babcock J G, Moran E E, Brandt B L, Matyas G R, Wassef N M, Alving C R. 2012. Phase I study of a *Neisseria meningitidis* liposomal vaccine containing purified outer membrane proteins and detoxified lipooligosaccharide. Vaccine 30:712-721.
100. Bernadac A, Gavioli M, Lazzaroni J C, Raina S, Lloubes R. 1998. *Escherichia coli* tol-pal mutants form outer membrane vesicles. J Bacteriol 180:4872-4878.
101. Henry T, Pommier S, Journet L, Bernadac A, Gorvel J P, Lloubes R. 2004. Improved methods for producing outer membrane vesicles in Gram-negative bacteria. Res Microbiol 155:437-446.
102. Berlanda Scorza F, Doro F, Rodriguez-Ortega M J, Stella M, Liberatori S, Taddei A R, Serino L, Gomes Moriel D, Nesta B, Fontana M R, Spagnuolo A, Pizza M, Norais N, Grandi G. 2008. Proteomics characterization of outer membrane vesicles from the extraintestinal pathogenic *Escherichia coli* ΔtolR IHE3034 mutant. Mol Cell Proteomics 7:473-485.
103. Clementz T, Zhou Z, Raetz C R. 1997. Function of the *Escherichia coli* msbB gene, a multicopy suppressor of htrB knockouts, in the acylation of lipid A. Acylation by MsbB follows laurate incorporation by HtrB. J Biol Chem 272:10353-10360.
104. Meloni E, Colucci A M, Micoli F, Sollai L, Gavini M, Saul A, Di Cioccio V, MacLennan C A. 2015. Simplified low-cost production of O-antigen from *Salmonella Typhimurium* Generalized Modules for Membrane Antigens (GMMA). J Biotechnol 198:46-52.
105. Gerke C, Colucci A M, Giannelli C, Sanzone S, Vitali C G, Sollai L, Rossi O, Martin L B, Auerbach J, Di Cioccio V, Saul A. 2015. Production of a *Shigella sonnei* Vaccine Based on Generalized Modules for Membrane Antigens (GMMA), 1790GAHB. PLoS One 10:e0134478.
106. Barat S, Willer Y, Rizos K, Claudi B, Maze A, Schemmer A K, Kirchhoff D, Schmidt A, Burton N, Bumann D. 2012. Immunity to intracellular *Salmonella* depends on surface-associated antigens. PLoS Pathog 8:e1002966.
107. Kurtz J R, Petersen H E, Frederick D R, Morici L A, McLachlan J B. 2014. Vaccination with a single CD4 T cell peptide epitope from a *Salmonella* type III-secreted effector protein provides protection against lethal infection. Infect Immun 82:2424-2433.
108. Rollenhagen C, Sorensen M, Rizos K, Hurvitz R, Bumann D. 2004. Antigen selection based on expression levels during infection facilitates vaccine development for an intracellular pathogen. Proc Natl Acad Sci USA 101:8739-8744.
109. Lee S J, McLachlan J B, Kurtz J R, Fan D, Winter S E, Baumler A J, Jenkins M K, McSorley S J. 2012. Temporal expression of bacterial proteins instructs host CD4 T cell expansion and Th17 development. PLoS Pathog 8:e1002499.
110. McSorley S J, Cookson B T, Jenkins M K. 2000. Characterization of CD4+ T cell responses during natural infection with *Salmonella* typhimurium. J Immunol 164:986-993.
111. Gil-Cruz C, Bobat S, Marshall J L, Kingsley R A, Ross E A, Henderson I R, Leyton D L, Coughlan R E, Khan M, Jensen K T, Buckley C D, Dougan G, MacLennan I C, Lopez-Macias C, Cunningham A F. 2009. The porin OmpD from nontyphoidal *Salmonella* is a key target for a protective B1 b cell antibody response. Proc Natl Acad Sci USA 106:9803-9808.
112. Yang Y, Wan C, Xu H, Aguilar Z P, Tan Q, Xu F, Lai W, Xiong Y, Wei H. 2013. Identification of an outer membrane protein of *Salmonella enterica* serovar Typhimurium as a potential vaccine candidate for Salmonellosis in mice. Microbes Infect 15:388-398.
113. Goh Y S, Armour K L, Clark M R, Grant A J, Mastroeni P. 2016. Igg Subclasses Targeting the Flagella of *Salmonella enterica* Serovar Typhimurium Can Mediate Phagocytosis and Bacterial Killing. J Vaccines Vaccin 7.
114. Cummings L A, Wilkerson W D, Bergsbaken T, Cookson B T. 2006. In vivo, fliC expression by *Salmonella enterica* serovar Typhimurium is heterogeneous, regulated by ClpX, and anatomically restricted. Mol Microbiol 61:795-809.
115. Winter S E, Winter M G, Godinez I, Yang H J, Russmann H, Andrews-Polymenis H L, Baumler A J. 2010. A rapid change in virulence gene expression during the transition from the intestinal lumen into tissue promotes systemic dissemination of *Salmonella*. PLoS Pathog 6:e1001060.
116. Cummings L A, Barrett S L, Wilkerson W D, Fellnerova I, Cookson B T. 2005. FliC-specific CD4+ T cell responses are restricted by bacterial regulation of antigen expression. J Immunol 174:7929-7938.
117. Simon R, Tennant S M, Wang J Y, Schmidlein P J, Lees A, Ernst R K, Pasetti M F, Galen J E, Levine M M. 2011.

Salmonella enterica serovar enteritidis core O polysaccharide conjugated to H:g,m flagellin as a candidate vaccine for protection against invasive infection with S. Enteritidis. Infect Immun 79:4240-4249.

118. Simon R, Wang J Y, Boyd M A, Tulapurkar M E, Ramachandran G, Tennant S M, Pasetti M, Galen J E, Levine M M. 2013. Sustained protection in mice immunized with fractional doses of *Salmonella Enteritidis* core and O polysaccharide-flagellin glycoconjugates. PLoS One 8:e64680.

119. Singh S P, Williams Y U, Benjamin W H, Klebba P E, Boyd D. 1996. Immunoprotection by monoclonal antibodies to the porins and lipopolysaccharide of *Salmonella* typhimurium. Microb Pathog 21:249-263.

120. Lee S J, Liang L, Juarez S, Nanton M R, Gondwe E N, Msefula C L, Kayala M A, Necchi F, Heath J N, Hart P, Tsolis R M, Heyderman R S, MacLennan C A, Feigner P L, Davies D H, McSorley S J. 2012. Identification of a common immune signature in murine and human systemic Salmonellosis. Proc Natl Acad Sci USA 109:4998-5003.

121. Secundino I, Lopez-Macias C, Cervantes-Barragan L, Gil-Cruz C, Rios-Sarabia N, Pastelin-Palacios R, Villasis-Keever M A, Becker I, Puente J L, Calva E, Isibasi A. 2006. *Salmonella* porins induce a sustained, lifelong specific bactericidal antibody memory response. Immunology 117:59-70.

122. Salazar-Gonzalez R M, Maldonado-Bernal C, Ramirez-Cruz N E, Rios-Sarabia N, Beltran-Nava J, Castanon-Gonzalez J, Castillo-Torres N, Palma-Aguirre J A, Carrera-Camargo M, Lopez-Macias C, Isibasi A. 2004. Induction of cellular immune response and anti-*Salmonella enterica* serovar Typhi bactericidal antibodies in healthy volunteers by immunization with a vaccine candidate against typhoid fever. Immunol Lett 93:115-122.

123. Santiviago C A, Toro C S, Bucarey S A, Mora G C. 2001. A chromosomal region surrounding the ompD porin gene marks a genetic difference between *Salmonella* typhi and the majority of *Salmonella* serovars. Microbiology 147:1897-1907.

124. Santiviago C A, Fuentes J A, Bueno S M, Trombert A N, Hildago A A, Socias L T, Youderian P, Mora G C. 2002. The *Salmonella enterica* sv. Typhimurium smvA, yddG and ompD (porin) genes are required for the efficient efflux of methyl viologen. Mol Microbiol 46:687-698.

125. Chakraborty S, Mizusaki H, Kenney L J. 2015. A FRET-based DNA biosensor tracks OmpR-dependent acidification of *Salmonella* during macrophage infection. PLoS Biol 13:e1002116.

126. Reynolds C J, Jones C, Blohmke C J, Darton T C, Goudet A, Sergeant R, Maillere B, Pollard A J, Altmann D M, Boyton R J. 2014. The serodominant secreted effector protein of *Salmonella*, SseB, is a strong CD4 antigen containing an immunodominant epitope presented by diverse HLA class II alleles. Immunology 143:438-446.

127. McLaughlin L M, Govoni G R, Gerke C, Gopinath S, Peng K, Laidlaw G, Chien Y H, Jeong H W, Li Z, Brown M D, Sacks D B, Monack D. 2009. The *Salmonella* SPI2 effector SseI mediates long-term systemic infection by modulating host cell migration. PLoS Pathog 5:e1000671.

128. Worley M J, Nieman G S, Geddes K, Heffron F. 2006. *Salmonella* typhimurium disseminates within its host by manipulating the motility of infected cells. Proc Natl Acad Sci USA 103:17915-17920.

129. McLaughlin L M, Xu H, Carden S E, Fisher S, Reyes M, Heilshorn S C, Monack D M. 2014. A microfluidic-based genetic screen to identify microbial virulence factors that inhibit dendritic cell migration. Integr Biol (Camb) 6:438-449.

130. Lawley T D, Chan K, Thompson L J, Kim C C, Govoni G R, Monack D M. 2006. Genome-wide screen for *Salmonella* genes required for long-term systemic infection of the mouse. PLoS Pathog 2:e11.

131. Thornbrough J M, Worley M J. 2012. A naturally occurring single nucleotide polymorphism in the *Salmonella* SPI-2 type III effector srfH/sseI controls early extraintestinal dissemination. PLoS One 7:e45245.

132. Toobak H, Rasooli I, Talei D, Jahangiri A, Owlia P, Darvish Alipour Astaneh S. 2013. Immune response variations to *Salmonella enterica* serovar Typhi recombinant porin proteins in mice. Biologicals 41:224-230.

133. Pascual D W, Suo Z, Cao L, Avci R, Yang X. 2013. Attenuating gene expression (AGE) for vaccine development. Virulence 4:384-390.

134. Yang X, Suo Z, Thornburg T, Holderness K, Cao L, Lim T, Walters N, Kellerman L, Loetterle L, Avci R, Pascual D W. 2012. Expression of *Escherichia coli* virulence usher protein attenuates wild-type *Salmonella*. Virulence 3:29-42.

135. Yang X, Thornburg T, Suo Z, Jun S, Robison A, Li J, Lim T, Cao L, Hoyt T, Avci R, Pascual D W. 2012. Flagella overexpression attenuates *Salmonella* pathogenesis. PLoS One 7:e46828.

136. Kong Q, Liu Q, Roland K L, Curtiss R, III. 2009. Regulated delayed expression of rfaH in an attenuated *Salmonella enterica* serovar Typhimurium vaccine enhances immunogenicity of outer membrane proteins and a heterologous antigen. Infect Immun 77:5572-5582.

137. Curtiss R, Ill., Munson M. 1998. Cross-protective *Salmonella* vaccines.

138. Kelly S M, Bosecker B A, Curtiss R, III. 1992. Characterization and protective properties of attenuated mutants of *Salmonella* choleraesuis. Infect Immun 60:4881-4890.

139. Hassan J O, Curtiss R, III. 1994. Development and evaluation of an experimental vaccination program using a live avirulent *Salmonella* typhimurium strain to protect immunized chickens against challenge with homologous and heterologous *Salmonella* serotypes. Infect Immun 62:5519-5527.

140. Richardson E J, Limaye B, Inamdar H, Datta A, Manjari K S, Pullinger G D, Thomson N R, Joshi R R, Watson M, Stevens M P. 2011. Genome sequences of *Salmonella enterica* serovar Typhimurium, Choleraesuis, Dublin, and Gallinarum strains of well-defined virulence in food-producing animals. J Bacteriol 193:3162-3163.

141. Kong Q, Liu Q, Jansen A, Curtiss R, III. 2010. Regulated delayed expression of rfc enhances the immunogenicity and protective efficacy of a heterologous antigen delivered by live attenuated *Salmonella enterica* vaccines. Vaccine 28:6094-6103.

142. Bertani G. 1951. Studies on lysogenesis. I. The mode of phage liberation by lysogenic *Escherichia coli*. J Bacteriol 62:293-300.

143. Sambrook J, Russel D W. 2001. Molecular cloning: a laboratory manual, 3rd ed. Cold Spring Harbor Laboratory Press, Cold Spring Harbor, N.Y.

144. Edwards R A, Keller L H, Schifferli D M. 1998. Improved allelic exchange vectors and their use to analyze 987P fimbria gene expression. Gene 207:149-157.

145. Schmieger H, Backhaus H. 1976. Altered cotransduction frequencies exhibited by H T-mutants of *Salmonella*-phage P22. Mol Gen Genet 143:307-309.

146. Kang H Y, Dozois C M, Tinge S A, Lee T H, Curtiss R, III. 2002. Transduction-mediated transfer of unmarked deletion and point mutations through use of counterselectable suicide vectors. J Bacteriol 184:307-312.

147. Kang H Y, Srinivasan J, Curtiss R, III. 2002. Immune responses to recombinant pneumococcal PspA antigen delivered by live attenuated *Salmonella enterica* serovar Typhimurium vaccine. Infect Immun 70:1739-1749.

148. Hitchcock P J, Brown T M. 1983. Morphological heterogeneity among *Salmonella* lipopolysaccharide chemotypes in silver-stained polyacrylamide gels. J Bacteriol 154:269-277.

149. Chibber S, Bhardwaj S B. 2004. Protection in a mouse peritonitis model mediated by iron-regulated outer-membrane protein of *Salmonella* typhi coupled to its Vi antigen. J Med Microbiol 53:705-709.

150. Schertzer J W, Whiteley M. 2013. Bacterial outer membrane vesicles in trafficking, communication and the host-pathogen interaction. J Mol Microbiol Biotechnol 23:118-130.

151. Kuehn M J, Kesty N C. 2005. Bacterial outer membrane vesicles and the host-pathogen interaction. Genes Dev 19:2645-2655.

152. Ho D K, Jarva H, Meri S. 2010. Human complement factor H binds to outer membrane protein Rck of *Salmonella*. Journal of Immunology 185:1763-1769.

153. Gahring L C, Heffron F, Finlay B B, Falkow S. 1990. Invasion and replication of *Salmonella* typhimurium in animal cells. Infection and Immunity 58:443-448.

154. Galan J E, Curtiss R, III. 1989. Cloning and molecular characterization of genes whose products allow *Salmonella* typhimurium to penetrate tissue culture cells. Proc Natl Acad Sci USA 86:6383-6387.

155. Moser I, Hohmann A, Schmidt G, Rowley D. 1980. Salmonellosis in mice: studies on oral immunization with live avirulent vaccines. Med Microbiol Immunol 168:119-128.

156. Nnalue N A, Stocker B A. 1987. Test of the virulence and live-vaccine efficacy of auxotrophic and galE derivatives of *Salmonella* choleraesuis. Infect Immun 55:955-962.

157. Germanier R. 1970. Immunity in Experimental Salmonellosis I. Protection Induced by Rough Mutants of *Salmonella* typhimurium. Infect Immun 2:309-315.

158. Kopecko D J, Sieber H, Ures J A, Furer A, Schlup J, Knof U, Collioud A, Xu D, Colburn K, Dietrich G. 2009. Genetic stability of vaccine strain *Salmonella Typhi* Ty21a over 25 years. Int J Med Microbiol 299:233-246.

159. Germanier R, Furer E. 1983. Characteristics of the attenuated oral vaccine strain "S. typhi" Ty 21a. Dev Biol Stand 53:3-7.

160. Edelman R, Levine M M. 1986. Summary of an international workshop on typhoid fever. Rev Infect Dis 8:329-349.

161. Wahdan M H, Serie C, Cerisier Y, Sallam S, Germanier R. 1982. A controlled field trial of live *Salmonella* typhi strain Ty 21a oral vaccine against typhoid: three-year results. J Infect Dis 145:292-295.

162. Wahdan M H, Serie C, Germanier R, Lackany A, Cerisier Y, Guerin N, Sallam S, Geoffroy P, el Tantawi A S, Guesry P. 1980. A controlled field trial of liver oral typhoid vaccine Ty21a. Bull World Health Organ 58:469-474.

163. Hone D M, Attridge S R, Forrest B, Morona R, Daniels D, LaBrooy J T, Bartholomeusz R C, Shearman D J, Hackett J. 1988. A galE via (Vi antigen-negative) mutant of *Salmonella* typhi Ty2 retains virulence in humans. Infect Immun 56:1326-1333.

164. Woodward T E, Woodward W E. 1982. A new oral vaccine against typhoid fever. J Infect Dis 145:289-291.

165. Nnalue N A, Stocker B A. 1986. Some galE mutants of *Salmonella* choleraesuis retain virulence. Infect Immun 54:635-640.

166. Fukasawa T, Nikaido H. 1961. Galactose-sensitive mutants of *Salmonella*. II. Bacteriolysis induced by galactose. Biochim Biophys Acta 48:470-483.

167. Nikaido H. 1961. Galactose-sensitive mutants of *Salmonella*. I. Metabolism of galactose. Biochim Biophys Acta 48:460-469.

168. Postma P W. 1977. Galactose transport in *Salmonella* typhimurium. J Bacteriol 129:630-639.

169. Müller N, Heine H G, Boos W. 1982. Cloning of mgiB, the structural gene for the galactose-binding protein of *Salmonella* typhimurium and *Escherichia coli*. Mol Gen Genet 185:473-480.

170. Clarke R C, Gyles C L. 1986. Galactose epimeraseless mutants of *Salmonella* typhimurium as live vaccines for calves. Can J Vet Res 50:165-173.

171. Shuster C W, Rundell K. 1969. Resistance of *Salmonella* typhimurium mutants to galactose death. J Bacteriol 100:103-109.

172. Mulford C A, Osborn M J. 1983. An intermediate step in translocation of lipopolysaccharide to the outer membrane of *Salmonella* typhimurium. Proc Natl Acad Sci USA 80:1159-1163.

173. Nagy G, Palkovics T, Otto A, Kusch H, Kocsis B, Dobrindt U, Engelmann S, Hecker M, Emody L, Pal T, Hacker J. 2008. "Gently rough": the vaccine potential of a *Salmonella enterica* regulatory lipopolysaccharide mutant. J Infect Dis 198:1699-1706.

174. Merighi M, Ellermeier C D, Slauch J M, Gunn J S. 2005. Resolvase—in vivo expression technology analysis of the *Salmonella enterica* serovar Typhimurium PhoP and PmrA regulons in BALB/c mice. J Bacteriol 187:7407-7416.

175. Brenneman K E, Willingham C, Kong W, Curtiss R, Ill, Roland K L. 2013. Low-pH rescue of acid-sensitive *Salmonella enterica* serovar Typhi strains by a Rhamnose-regulated arginine decarboxylase system. J Bacteriol 195:3062-3072.

176. Singh S P, Williams Y U, Klebba P E, Macchia P, Miller S. 2000. Immune recognition of porin and lipopolysaccharide epitopes of *Salmonella* typhimurium in mice. Microb Pathog 28:157-167.

177. Bentley A T, Klebba P E. 1988. Effect of lipopolysaccharide structure on reactivity of antiporin monoclonal antibodies with the bacterial cell surface. J Bacteriol 170:1063-1068.

178. Stevenson G, Andrianopoulos K, Hobbs M, Reeves P R. 1996. Organization of the *Escherichia coli* K-12 gene cluster responsible for production of the extracellular polysaccharide colanic acid. J Bacteriol 178:4885-4893.

179. Whitfield C. 2006. Biosynthesis and assembly of capsular polysaccharides in *Escherichia coli*. Annu Rev Biochem 75:39-68.

180. Wang S, Li Y, Scarpellini G, Kong W, Shi H, Baek C H, Gunn B, Wanda S Y, Roland K L, Zhang X, Senechal-Willis P, Curtiss R, III. 2010. *Salmonella* vaccine vectors displaying delayed antigen synthesis in vivo to enhance immunogenicity. Infect Immun 78:3969-3980.

181. Sun W, Wang S, Curtiss R, III. 2008. Highly efficient method for introducing successive multiple scarless gene 181. deletions and markerless gene insertions into the *Yersinia pestis* chromosome. Applied and Environmental Microbiology 74:4241-4245.
182. Baek C H, Wang S, Roland K L, Curtiss R, III. 2009. Leucine-responsive regulatory protein (Lrp) acts as a virulence repressor in *Salmonella enterica* serovar Typhimurium. J Bacteriol 191:1278-1292.

183. Juarez-Rodriguez M D, Arteaga-Cortes L T, Kader R, Curtiss R, Ill, Clark-Curtiss J E. 2012. Live attenuated *Salmonella* vaccines against *Mycobacterium tuberculosis* with antigen delivery via the type III secretion system. Infect Immun 80:798-814.

184. Smith K D, Andersen-Nissen E, Hayashi F, Strobe K, Bergman M A, Barrett S L, Cookson B T, Aderem A. 2003. Toll-like receptor 5 recognizes a conserved site on flagellin required for protofilament formation and bacterial motility. Nat Immunol 4:1247-1253.

185. Murthy K G, Deb A, Goonesekera S, Szabo C, Salzman A L. 2004. Identification of conserved domains in *Salmonella muenchen* flagellin that are essential for its ability to activate TLR5 and to induce an inflammatory response in vitro. J Biol Chem 279:5667-5675.

186. Cookson B T, Bevan M J. 1997. Identification of a natural T cell epitope presented by *Salmonella*-infected macrophages and recognized by T cells from orally immunized mice. J Immunol 158:4310-4319.

187. Juarez-Rodriguez M D, Yang J, Kader R, Alamuri P, Curtiss R, Ill., Clark-Curtiss J E. 2012. Live attenuated *Salmonella* vaccines displaying regulated delayed lysis and delayed antigen synthesis to confer protection against *Mycobacterium tuberculosis*. Infect Immun 80:815-831.

188. Jiang Y, Mo H, Willingham C, Wang S, Park J Y, Kong W, Roland K L, Curtiss R, III. 2015. Protection Against Necrotic Enteritis in Broiler Chickens by Regulated Delayed Lysis *Salmonella* Vaccines. Avian Dis 59:475-485.

189. Xin W, Wanda S Y, Zhang X, Santander J, Scarpellini G, Ellis K, Alamuri P, Curtiss R, III. 2012. The $Asd^+$-$DadB^+$ dual-plasmid system offers a novel means to deliver multiple protective antigens by a recombinant attenuated *Salmonella* vaccine. Infect Immun 80:3621-3633.

190. Zhang X, Kong W, Ashraf S, Curtiss R, III. 2009. A one-plasmid system to generate influenza virus in cultured chicken cells for potential use in influenza vaccine. J Virol 83:9296-9303.

191. Zhang X, Curtiss R, III. 2015. Efficient generation of influenza virus with a mouse RNA polymerase I-driven all-in-one plasmid. Virol J 12:95.

192. Zhang X, Kong W, Wanda S Y, Xin W, Alamuri P, Curtiss R, III. 2015. Generation of influenza virus from avian cells infected by *Salmonella* carrying the viral genome. PLoS One 10:e0119041.

193. Sanapala S, Rahav H, Patel H, Sun W, Curtiss R, III. 2016. Multiple antigens of *Yersinia pestis* delivered by live recombinant attenuated *Salmonella* vaccine strains elicit protective immunity against plague. Vaccine 34:2410-2416.

194. Zhang X, Wanda S Y, Brenneman K, Kong W, Roland K, Curtiss R, Ill. 2011. Improving *Salmonella* vector with rec mutation to stabilize the DNA cargoes. BMC Microbiol 11:31.

195. Marvin H J, ter Beest M B, Witholt B. 1989. Release of outer membrane fragments from wild-type *Escherichia coli* and from several *E. coli* lipopolysaccharide mutants by EDTA and heat shock treatments. J Bacteriol 171:5262-5267.

196. Witholt B, Boekhout M, Brock M, Kingma J, Heerikhuizen H V, Leij L D. 1976. An efficient and reproducible procedure for the formation of spheroplasts from variously grown *Escherichia coli*. Anal Biochem 74:160-170.

197. Juarez-Rodriguez M D, Arteaga-Cortes L T, Kader R, Curtiss R, Ill., Clark-Curtiss J E. 2012. Live attenuated *Salmonella* vaccines against *Mycobacterium tuberculosis* with antigen delivery via the type III secretion system. Infect Immun 80:798-814.

198. Konjufca V, Wanda S Y, Jenkins M C, Curtiss R, III. 2006. A recombinant attenuated *Salmonella enterica* serovar Typhimurium vaccine encoding *Eimeria acervulina* antigen offers protection against *E. acervulina* challenge. Infect Immun 74:6785-6796.

199. Konjufca V, Jenkins M, Wang S, Juarez-Rodriguez M D, Curtiss R, Ill. 2008. Immunogenicity of recombinant attenuated *Salmonella enterica* serovar Typhimurium vaccine strains carrying a gene that encodes *Eimeria tenella* antigen SO7. Infect Immun 76:5745-5753.

200. Shi H, Santander J, Brenneman K E, Wanda S Y, Wang S, Senechal P, Sun W, Roland K L, Curtiss R, III. 2010. Live recombinant *Salmonella* Typhi vaccines constructed to investigate the role of rpoS in eliciting immunity to a heterologous antigen. PLoS One 5:e11142.

201. Czerkinsky C C, L. A. Nilsson, H. Nygren, O. Ouchterlony, and A. Tarkowski. 1983. A solid-phase enzyme-linked immunospot (ELISPOT) assay for enumeration of specific antibody-secreting cells. J Immunol Methods 65:109-121.

202. Li Y, Wang S, Scarpellini G, Gunn B, Xin W, Wanda S Y, Roland K L, Curtiss R, III. 2009. Evaluation of new generation *Salmonella enterica* serovar Typhimurium vaccines with regulated delayed attenuation to induce immune responses against PspA. Proc Natl Acad Sci USA 106:593-598.

203. Bonato V L D, V. M. F. Lima, R. E. Tascon, D. B. Lowrie, and C. L. Silva. 1998. Identification and characterization of protective T cells in hsp65 DNA-vaccinated and *Mycobacterium tuberculosis*-infected mice. Infect Immun 66:169-175.

204. Okamoto Y, H. Murakami, and M. Nishida. 1997. Detection of interleukin 6-producing cells among various organs in normal mice with an improved enzyme-linked immunospot (ELISPOT) assay. Endocr J 44:349-355.

205. Broz P, Newton K, Lamkanfi M, Mariathasan S, Dixit V M, Monack D M. 2010. Redundant roles for inflammasome receptors NLRP3 and NLRC4 in host defense against *Salmonella*. J Exp Med 207:1745-1755.

206. Rathinam V A, Vanaja S K, Waggoner L, Sokolovska A, Becker C, Stuart L M, Leong J M, Fitzgerald K A. 2012. TRIF licenses caspase-11-dependent NLRP3 inflammasome activation by gram-negative bacteria. Cell 150:606-619.

207. Riedemann N C, Guo R F, Sarma V J, Laudes I J, Huber-Lang M, Warner R L, Albrecht E A, Speyer C L, Ward P A. 2002. Expression and function of the C5a receptor in rat alveolar epithelial cells. J Immunol 168:1919-1925.

208. Montz H, Koch K C, Zierz R, Gotze O. 1991. The role of C5a in interleukin-6 production induced by lipopolysaccharide or interleukin-1. Immunology 74:373-379.

209. Buckner C M, Kardava L, Moir S. 2013. Evaluation of B cell function in patients with HIV. Curr Protoc Immunol Chapter 12:Unit 12 13.

210. Flores-Langarica A, Bobat S, Marshall J L, Yam-Puc J C, Cook C N, Serre K, Kingsley R A, Flores-Romo L, Uematsu S, Akira S, Henderson I R, Toellner K M, Cunningham A F. 2015. Soluble flagellin coimmunization attenuates Th1 priming to *Salmonella* and clearance by modulating dendritic cell activation and cytokine production. Eur J Immunol 45:2299-2311.

211. Quah B J, Wijesundara D K, Ranasinghe C, Parish C R. 2014. The use of fluorescent target arrays for assessment of T cell responses in vivo. J Vis Exp doi:10.3791/51627: e51627.

212. Quah B J, Wijesundara D K, Ranasinghe C, Parish C R. 2013. Fluorescent target array T helper assay: a multiplex flow cytometry assay to measure antigen-specific CD4+ T cell-mediated B cell help in vivo. J Immunol Methods 387:181-190.

213. Cretel E, Touchard D, Bongrand P, Pierres A. 2011. A new method for rapid detection of T lymphocyte decision to proliferate after encountering activating surfaces. J Immunol Methods 364:33-39.

214. Quah B J, Parish C R. 2010. The use of carboxyfluorescein diacetate succinimidyl ester (CFSE) to monitor lymphocyte proliferation. J Vis Exp doi:10.3791/2259.

215. Parish C R, Glidden M H, Quah B J, Warren H S. 2009. Use of the intracellular fluorescent dye CFSE to monitor lymphocyte migration and proliferation. Curr Protoc Immunol Chapter 4:Unit4 9.

216. Wallace P K, Tario J D, Jr., Fisher J L, Wallace S S, Ernstoff M S, Muirhead K A. 2008. Tracking antigen-driven responses by flow cytometry: monitoring proliferation by dye dilution. Cytometry A 73:1019-1034.

217. Hawkins E D, Hommel M, Turner M L, Battye F L, Markham J F, Hodgkin P D. 2007. Measuring lymphocyte proliferation, survival and differentiation using CFSE time-series data. Nat Protoc 2:2057-2067.

218. Brenchley J M, Douek D C. 2004. Flow cytometric analysis of human antigen-specific T-cell proliferation. Methods Cell Biol 75:481-496.

219. Tennant S M, Schmidlein P, Simon R, Pasetti M F, Galen J E, Levine M M. 2015. Refined live attenuated *Salmonella enterica* serovar Typhimurium and Enteritidis vaccines mediate homologous and heterologous serogroup protection in mice. Infect Immun 83:4504-4512.

220. Kong Q, Six D A, Roland K L, Liu Q, Gu L, Reynolds C M, Wang X, Raetz C R, Curtiss R, III. 2011. *Salmonella* synthesizing 1-dephosphorylated lipopolysaccharide exhibits low endotoxic activity while retaining its immunogenicity. J Immunol 187:412-423.

221. Kong Q, Six D A, Liu Q, Gu L, Wang S, Alamuri P, Raetz C R, Curtiss R, Ill. 2012. Phosphate groups of Lipid A are essential for *Salmonella enterica* serovar Typhimurium virulence and affect innate and adaptive immunity. Infect Immun 80:3215-3224.

What is claimed is:

1. A recombinant derivative of a pathogenic bacterium, wherein the bacterium is a *Salmonella enterica*, and wherein the bacterium comprises
 a murA gene operably linked to a first sugar-regulatable promoter, wherein the first sugar-regulatable promoter is an arabinose-regulatable promoter, a rhamnose-regulatable promoter, or a xylose regulatable-promoter;
 a deletion-insertion mutation that inactivates the expression of asdA gene and inserts a c2 gene;
 a deletion in a pmi gene;
 a deletion in a pagL gene;
 a waaL gene operably linked to a second sugar-regulatable promoter, wherein the second sugar-regulatable promoter is an arabinose-regulatable promoter, a rhamnose-regulatable promoter, or a xylose regulatable-promoter;
 a deletion in a wza-wcaM gene;
 a deletion-insertion mutation that inactivates the expression of a RelA gene and inserts a lacI gene;
 a deletion in a recF gene; and
 a deletion in a sifA gene.

2. The bacterium of claim 1, wherein the first sugar-regulatable promoter is selected from the group consisting of araC $P_{araBAD}$, rhaRS-$P_{rhaBAD}$ and xylR-$P_{xylA}$.

3. The bacterium of claim 2, wherein the second sugar-regulatable promoter is selected from the group consisting of araC $P_{araBAD}$, rhaRS-$P_{rhaBAD}$ and xylR-$P_{xylA}$.

4. The bacterium of claim 3, wherein
 the deletion-insertion mutation that inactivates the expression of the asdA gene and inserts the c2 gene is ΔasdA27::TT araC PBA D c2;
 the deletion in the pmi gene is Δpmi-2426;
 the deletion in the wza-wcaM gene is Δ(wza-wcaM)-8;
 the deletion-insertion mutation that inactivates the expression of the RelA gene and inserts the locI gene is ΔrelA197::araC PBA D locI TT;
 the deletion in the recF gene is ΔrecF126; and
 the deletion in the sifA gene is ΔsifA26.

5. The bacterium of claim 1, wherein the bacterium further comprises a gene encoding an antigen of interest operably linked to a third sugar-regulatable promoter.

6. The bacterium of claim 5, wherein the third sugar-regulatable promoter is a lactose-regulatable promoter.

7. The bacterium of claim 6, wherein the lactose-regulatable promoter is $P_{trc}$.

8. The bacterium of claim 5, wherein the antigen of interest is an antigen derived from an infectious agent or a cancer antigen.

9. The bacterium of claim 6, wherein the antigen is a *Clostridium perfringens* antigen.

10. The bacterium of claim 9, wherein the *Clostridium perfringens* antigen is a NetB antigen or antigenic fragment thereof, a PlcC antigen or antigenic fragment thereof, or a fusion protein comprising the NetB antigen or antigenic fragment thereof and the PlcC antigen or antigenic fragment thereof.

11. The recombinant bacterium of claim 10, wherein the bacterium comprises the plasmid pYA5112.

12. A pharmaceutical composition comprising the recombinant bacterium of claim 1, and a pharmaceutically acceptable carrier.

13. A method for eliciting an immune response against an antigen of interest in a subject, the method comprising administering to the subject an effective amount of a pharmaceutical composition of claim 12.

14. The method of claim 13, wherein the subject has necrotic enteritis.

15. The method of claim 13, wherein the subject is a chicken.

16. The method of claim 13, wherein the pharmaceutical composition is administered to the subject by spray or oral immunization.

* * * * *